US010648966B2

(12) United States Patent
Guo et al.

(10) Patent No.: US 10,648,966 B2
(45) Date of Patent: May 12, 2020

(54) LIPID BILAYER-INTEGRATED SPP1 CONNECTOR PROTEIN NANOPORE AND SPP1 CONNECTOR PROTEIN VARIANTS FOR USE AS LIPID BILAYER-INTEGRATED NANOPORE

(71) Applicant: UNIVERSITY OF KENTUCKY RESEARCH FOUNDATION, Lexington, KY (US)

(72) Inventors: Peixuan Guo, Lexington, KY (US); Shaoying Wang, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 207 days.

(21) Appl. No.: 15/543,821

(22) PCT Filed: Jan. 15, 2016

(86) PCT No.: PCT/US2016/013702
§ 371 (c)(1),
(2) Date: Jul. 14, 2017

(87) PCT Pub. No.: WO2016/115522
PCT Pub. Date: Jul. 21, 2016

(65) Prior Publication Data
US 2017/0343530 A1   Nov. 30, 2017

Related U.S. Application Data

(60) Provisional application No. 62/104,375, filed on Jan. 16, 2015.

(51) Int. Cl.
*C07K 14/005* (2006.01)
*G01N 33/487* (2006.01)
(Continued)

(52) U.S. Cl.
CPC ..... *G01N 33/48721* (2013.01); *C07K 14/005* (2013.01); *C12Q 1/6869* (2013.01);
(Continued)

(58) Field of Classification Search
None
See application file for complete search history.

(56) References Cited

U.S. PATENT DOCUMENTS

| 8,945,577 | B2 * | 2/2015 | Blais ................ A61K 39/102 |
| | | | 424/185.1 |
| 9,234,238 | B2 * | 1/2016 | Guo ................... B82Y 15/00 |
| 2014/0174927 | A1 | 6/2014 | Bashir et al. |

FOREIGN PATENT DOCUMENTS

WO   2010/062697   6/2010

OTHER PUBLICATIONS

NCBI Reference Sequence: NP_690661.1 for Bacillus phage SPP1 (Year: 2018).*

(Continued)

*Primary Examiner* — Michelle S Horning
(74) *Attorney, Agent, or Firm* — Baker Donelson

(57) ABSTRACT

A conductive channel-containing membrane includes a membrane layer, and a SPP1 connector polypeptide variant that is incorporated into the membrane layer to form an aperture through which conductance can occur when an electrical potential is applied across the membrane. A method of sensing a molecule, such as a polypeptide or nucleic acid molecule, makes use of the conductive channel-containing membrane. A method of DNA sequence makes use of the conductive channel-containing membrane.

14 Claims, 10 Drawing Sheets

Specification includes a Sequence Listing.

(51) Int. Cl.
*C12Q 1/6869* (2018.01)
*G01N 27/447* (2006.01)

(52) U.S. Cl.
CPC ............ *G01N 27/44791* (2013.01); *C12N 2795/10322* (2013.01); *G01N 2333/01* (2013.01)

(56) References Cited

OTHER PUBLICATIONS

Bornhorst and Falke. Purification of proteins using polyhistidine affinity tags. Methods Enzymol. 2000;326:245-54. (Year: 2000).*
Sharp and Li. Codon usage in regulatory genes in *Escherichia coli* does not reflect selection for 'rare' codons. Nucleic Acids Res. Oct. 10, 1986;14(19):7737-49. (Year: 1986).*
Camacho et al. "Bacillus subtilis Bacteriophage SPP1 DNA Packaging Motor Requires Terminase and Portal Proteins" The Journal of Biological Chemistry; vol. 278, No. 26, Issue of Jun. 27, pp. 23251-23259, 2003.
Ding et al. "Structure and assembly of the essential RNA ring component of a viral DNA packaging motor" PNAS, May 3, 2011; vol. 108; No. 18 pp. 7357-7362.
Geng et al. "Channel Size Conversion of Phi29 DNA-Packaging Nanomotor for Discrimination of Single- and Double-Stranded Nucleic Acids" ACS Nano. Apr. 23, 2013; 7(4): 3315-3323. doi:10.1021/nn400020z.
Geng et al. "Three reversible and controllable discrete steps of channel gating of a viral DNA packaging motor" Biomaterials. Nov. 2011; 32(32): 8234-8242. doi:10.1016/j.biomaterials.2011.07.034.
Lhuillier et al. "Structure of bacteriophage SPP1 head-to-tail connection reveals mechanism for viral DNA gating" PNAS; May 26, 2009 vol. 106 No. 21 8507-8512.
Wendell et al. "Translocation of double stranded DNA through membrane adapted phi29 motor protein nanopore" Nat Nanotechnol. Nov. 2009; 4(11): 765-772. doi:10.1038/nnano.2009.259.
Hinnah, S. C. et al. The chloroplast protein import channel Toc75: Pore properties and interaction with transit peptides. Biophys. J. 83, 899-911 (2002).
Howorka, Stefan, Stephen Cheley, and Hagan Bayley. "Sequence-specific detection of individual DNA strands using engineered nanopores." Nature biotechnology 19.7 (2001): 636.
Hu , B . , Margolin , W . , Molineux , I . J . & Liu , J . , Structural remodeling of bacteriophage T4 and host membranes during infection initiation . Proc . Natl . Acad . Sci . U . SA 112 , E4919-E4928 ( 2015 ).
Hwang, Y., Catalano, C. E. & Feiss, M. Kinetic and mutational dissection of the two ATPase activities of terminase, the DNA packaging enzyme of bacteriophage lambda. Biochemistry 35, 2796-2803 (1996).
Ionel, A.; Velazquez-Muriel, J. A.; Luque, D.; Cuervo, A.; Caston, J. R.; Valpuesta, J. M.; Martin-Benito, J.; Carrascosa, J. L. Molecular Rearrangements Involved in the Capsid Shell Maturation of Bacteriophage T7. J. Biol. Chem. 2011, 286, 234-242.
Iqbal, Samir M.; Demir Akin, and Rashid Bashir. "Solid-state nanopore channels with DNA selectivity." Nature nanotechnology 2.4 (2007): 243.
Jetha, Nahid N., et al. "Nanopore analysis of wild-type and mutant prion protein (PrPC): single molecule discrimination and PrPC kinetics." PLoS One 8.2 (2013): e54982.
Jing, P. et al., One-Way Traffic of a Viral Motor Channel for Double-Stranded DNA Translocation. Nano Lett. 10, 3620-3627 (2010).
Jing, P.; Hague, F.; Vonderheide, A.; Montemagno, C.; Guo, P. Robust Properties of Membrane-Embedded Connector Channel of Bacterial Virus Phi29 DNA Packaging Motor. Mol. BioSyst. 2010, 6, 1844-1852.
Kasianowicz, J. J., Brandin, E., Branton, D. & Deamer, D. W., Characterization of individual polynucleotide molecules using a membrane channel. Proc. Natl. Acad. Sci. U.SA 93, 13770-13773 (1996).
Kemp, P.; Garcia, L. R.; Molineux, I. J. Changes in Bacteriophage T7 Virion Structure at the Initiation of Infection. Virology 2005, 340, 307-317.
Kemp, P.; Gupta, M.; Molineux, I. J. Bacteriophage T7 DNA Ejection into Cells is Initiated by an Enzyme-Like Mechanism. Mol. Microbiol. 2004, 53, 1251-1265.
Khan, S. A.; Hayes, S. J.; Wright, E. T.; Watson, R. H.; Serwer, P. Specific Single-Stranded Breaks in Mature Bacteriophage T7 DNA. Virology 1995, 211, 329-331.
Kim , J . W . , Kim , J . H . & Deaton , R . , DNA Linked Nanoparticle Building Blocks for Programmable Matter . Angewandte Chemie—International Edition 50 , 9185-9190 ( 2011 ).
Kinouchi, N. et al., Atelocollagen-mediated local and systemic applications of myostatin-targeting siRNA increase skeletal muscle mass. Gene Ther., (2008).
Kittigul, Leera, et al. "Dengue hemorrhagic fever: knowledge, attitude and practice in Ang Thong Province, Thailand." Southeast Asian journal of tropical medicine and public health34.2 (2003): 385-392.Cordiano et al., J Immunol Methods. Jan. 13, 1995; 178(1):121-30.
Kowalczyk, S. W.; Tuijtel, M. W.; Donkers, S. P.; Dekker, C. Unraveling Single-Stranded DNA in a Solid-State Nanopore. Nano Lett. 2010, 10, 1414-1420.
Kukwikila, M. & Howorka, S., Nanopore-Based Electrical and Label-Free Sensing of Enzyme Activity in Blood Serum. Anal. Chem. 87, 9149-9154 (2015).
Lebedev, A. A. et al., Structural framework for DNA translocation via the viral portal protein. EMBO J. 26, 1984-1994 (2007).
Li , H. et al. , RNA as a stable polymer to build controllable and defined nanostructures for material and biomedical applications . Nano Today in press . ( 2015 ).
Lowe, J.; Ellonen, A.; Allen, M. D.; Atkinson, C.; Sherratt, D. J.; Grainge, I. Molecular Mechanism of Sequence-Directed DNA Loading and Translocation by FtsK. Mol. Cell 2008, 31, 498-509.
Maglia, G.; Heron, A. J.; Hwang, W. L.; Holden, M. A.; Mikhailova, E.; Li, Q.; Cheley, S.; Bayley, H. Droplet Networks with Incorporated Protein Diodes Show Collective Properties. Nat. Nanotechnol. 2009, 4, 437-440.
Majd, S. et al., Applications of biological pores in nanomedicine, sensing, and nanoelectronics. Current Opinion in Biotechnology 21, 439-476 (2010).
Maluf, N. K.; Gaussier, H.; Bogner, E.; Feiss, M.; Catalano, C. E. Assembly of Bacteriophage Lambda Terminase into a Viral DNA Maturation and Packaging Machine. Biochemistry. 2006, 45, 15259-15268.
Manrao, E. A. et al., Reading DNA at single-nucleotide resolution with a mutant MspA nanopore and phi29 DNA polymerase. Nat Biotechnol. 30, 349-353 (2012).
Mathe, J.; Aksimentiev, A.; Nelson, D. R.; Schulten, K.; Meller, A. Orientation Discrimination of Single-Stranded DNA Inside the Alpha-Hemolysin Membrane Channel. Proc. Natl. Acad. Sci. U.S.A 2005, 102, 12377-12382.
Matias, P. M.; Gorynia, S.; Donner, P.; Carrondo, M. A. Crystal Structure of the Human AAA+ Protein RuvBL1. J. Biol. Chem. 2006, 281, 38918-38929.
Maupetit, J., Derreumaux, P. & Tuffery, P., PEP-FOLD: an online resource for de novo peptide structure prediction. Nucleic Acids Res 37, W498-W503 (2009).
McGeoch, A. T.; Trakselis, M. A.; Laskey, R. A.; Bell, S. D. Organization of the Archaeal MCM Complex on DNA and Implications for the Helicase Mechanism. Nat. Struct. Mol. Biol. 2005, 12, 756-762.
Mereuta, L. et al., Slowing down single-molecule trafficking through a protein nanopore reveals intermediates for peptide translocation. Sci. Rep. 4, 3885 (2014).
Miedema, H.; Vrouenraets, M.; Wierenga, J.; Meijberg, W.; Robillard, G.; Eisenberg, B. A Biological Porin Engineered into a Molecular, Nanofluidic Diode. Nano Lett. 2007, 7, 2886-2891.

(56) References Cited

OTHER PUBLICATIONS

Moffitt, J. R.; Chemla, Y. R.; Aathavan, K.; Grimes, S.; Jardine, P. J.; Anderson, D. L.; Bustamante, C. Intersubunit Coordination in a Homomeric Ring ATPase. Nature 2009, 457, 446-450.
Mohammad, Mohammad M., and Liviu Movileanu. "Protein sensing with engineered protein nanopores." Nanopore-Based Technology. Humana Press, 2012. 21-37.
Movileanu, L., Howorka, S., Braha, O. & Bayley, H. Detecting protein analytes that modulate transmembrane movement of a polymer chain within a single protein pore. Nature Biotechnol. 18, 1091-1095 (2000).
Movileanu, L., Squeezing a single polypeptide through a nanopore. Soft Matter 4, 925-931 (2008).
Movileanu, Liviu. "Watching single proteins using engineered nanopores." Protein and peptide letters 21.3 (2014): 235-246.
Nerurkar, Lata S., et al. "Rapid detection of herpes simplex virus in clinical specimens by use of a capture biotin-streptavidin enzyme-linked immunosorbent assay." Journal of clinical microbiology 20.1 (1984): 109-114.
Olia, A. S.; Prevelige, P. E.; Johnson, J. E.; Cingolani, G. Three-Dimensional Structure of a Viral Genome-Delivery Portal Vertex. Nat Struct Mol Biol 2011, 18, 597-603.
Oliveira, L.; Henriques, A. 0.; Tavares, P. Modulation of the Viral ATPase Activity by the Portal Protein Correlates With DNA Packaging Efficiency. J Biol Chem 2006, 281, 21914-21923.
Oram, M.; Sabanayagam, C.; Black, L. W. Modulation of the Packaging Reaction of Bacteriophage T4 Terminase by DNA Structure. J Mol Biol 2008, 381, 61-72.
Orlova , E . V . et al ., Structure of a viral DNA gatekeeper at 10 A resolution by cryo—electron microscopy . EMBO J . 22 , 1255-1262 ( 2003 ).
Peterson, Robert R., Barbara J. Deeb, and Ronald F. DiGiacomo. "Detection of Antibodies to Pasteurella multocida by capture enzyme immunoassay using a monoclonal antibody against P37 antigen." Journal of clinical microbiology35.1 (1997): 208-212.
Pi , F . et al ., Discovery of a new method for potent drug development using power function of stoichiometry of homomeric biocomplexes or biological nanomotors . Expert Opin . Drug Deliv . 1-14 (2015).
Ray, K.; Oram, M.; Ma, J.; Black, L. W. Portal Control of Viral Prohead Expansion and DNA Packaging. Virology 2009, 391, 44-50.
Reiner, J. E. et al., Disease detection and management via single nanopore-based sensors. Chem. Rev. 112, 6431-6451 (2012).
Robinson, M. A. et al., Affinity of molecular interactions in the bacteriophage phi29 DNA packaging motor. Nucleic Acids Res. 34, 2698-2709 (2006).
Rosen, Christian B., David Rodriguez-Larrea, and Hagan Bayley. "Single-molecule site-specific detection of protein phosphorylation with a nanopore." Nature biotechnology 32.2 (2014): 179.
Roy, Roopali, et al. "Tumor-specific urinary matrix metalloproteinase fingerprinting: identification of high molecular weight urinary matrix metalloproteinase species." Clinical Cancer Research 14.20 (2008): 6610-6617.
Sabanayagam, C. R., Oram, M., Lakowicz, J. R. & Black, L. W. Viral DNA packaging studied by fluorescence correlation spectroscopy. Biophys. J. 93, L17-L19 (2007).
Serwer, P.; Wright, E. T.; Hakala, K.; Weintraub, S. T.; Su, M.; Jiang, W. DNA Packaging-Associated Hyper-Capsid Expansion of Bacteriophage T3. J. Mol. Biol. 2010, 397, 361-374.
Lubenko, A., and J. Savage. "Antigen capture ELISA for platelet antibody detection: choice of conjugate influences assay result." Transfusion medicine (Oxford, England) 10.3 (2000): 213-218.
Chanteau, S., et al. "45/47 kilodalton (APA) antigen capture and antibody detection assays for the diagnosis of tuberculosis." The International Journal of Tuberculosis and Lung Disease 4.4 (2000): 377-383.
Wolff et al., Cancer Res. 53:2560-65 (1993).
Ali et al., J Agric Food Chem. 2009.
Leski et al., Appl Environ Microbiol. Sep. 18, 2009.
Pei et al., Zhongguo Zhong Yao Za Zhi. 2008 33(14):1662-8.
Zhao et al., Se Pu 2008 26(1):43-9.
Bayley et al., 2001 Nature 13:225-230.
Mobasheri, Hamid, and Edward J. Lea. "Biophysics of gating phenomena in voltage-dependent OmpC mutant porin channels (R74C and R37C) of *Escherichia coli* outer membranes." European Biophysics Journal 31.5 (2002): 389-399.
Biswas, S. et al., Click Addition of a DNA Thread to the N-Termini of Peptides for Their Translocation through Solid-State Nanopores. ACS Nano. 9, 9652-9664 (2015).
Geng, J. et al., Stochastic transport through carbon nanotubes in lipid bilayers and live cell membranes. Nature 514, 612-615 (2014).
Guo, P., Peterson, C. & Anderson, D. Prohead and DNA-gp3 dependent ATPase activity of the DNA packaging protein gp16 of bacteriophage f29. J. Mol. Biol. 197, 229-236 (1987).
Kasianowicz, J. J. et al., Nanoscopic porous sensors. Annu. Rev. Anal. Chem. (Palo. Alto. Calif.) 1, 737-766 (2008).
Meifer, W. J. J.; Horcajadas, J. A.; Salas, M. Phi29 Family of Phages. Microbiol. Mol. Biol Rev. 2001, 65(2), 261-287.
Serwer, P. The Source of Energy for Bacteriophage DNA Packaging: an Osmotic Pump Explains the Data. Biopolymers 1988, 27, 165-169.
Tang, J. H.; Olson, N.; Jardine, P. J.; Girimes, S.; Anderson, D. L.; Baker, T. S. DNA Poised for Release in Bacteriophage Phi29. Structure 2008, 16, 935-943.
Soong, R. K.; Bachand, G. D.; Neves, H. P.; Olkhovets, A. G.; Craighead, H. G.; Montemagno, C. D. Powering an Inorganic Nanodevice With a Biomolecular Motor. Science 2000, 290, 1555-1558.
Simpson A A, Leiman P G, Tao Y, He Y, Badasso M O, Jardine P J, Anderson D L, Rossmann M G (2001) Structure determination of the head-tail connector of bacteriophage phi29. Acta Crystallogr D57: 1260-1269.
Shi, Hai Ming, et al. "Identification of Cistanche species by chemical and inter-simple sequence repeat fingerprinting." Biological and Pharmaceutical Bulletin 32.1 (2009): 142-146.
Shu , D . et al ., Thermodynamically stable RNA three way junctions for constructing multifuntional nano particles for delivery of therapeutics . Nature Nanotechnology 6 , 658-667 ( 2011 ).
Shu, D.; Zhang, H.; Jin, J.; Guo, P. Counting of Six PRNAs of Phi29 DNA-Packaging Motor With Customized Single Molecule Dual-View System. EMBO J. 2007, 26, 527-537.
Skordalakes, E.; Berger, J. M. Structural Insights into RNA-Dependent Ring Closure and ATPase Activation by the Rho Termination Factor Cell 2006, 127, 553-564.
Smeets, Ralph MM, et al. "Salt dependence of ion transport and DNA translocation through solid-state nanopores." Nano letters 6.1 (2006): 89-95.
Sokabe, M.; Sachs, F.; Jing, Z. Q. Quantitative Video Microscopy of Patch Clamped Membranes Stress, Strain, Capacitance, and Stretch Channel Activation. Biophysical Journal 1991, 59, 722-728.
Steuerwald, D. et al., Nanoshuttles propelled by motor proteins sequentially assemble molecular cargo in a microfluidic device. Lab Chip 14, 3729-3738 (2014).
Stoddart, D. et al., Single-nucleotide discrimination in immobilized DNA oligonucleotides with a biological nanopore. Proc. Natl. Acad. Sci. U.S.A. 106, 7702-7707 (2009).
Sun, S. Y.; Kondabagil, K.; Gentz, P. M.; Rossmann, M. G.; Rao, V. B. The Structure of the ATPase That Powers DNA Packaging into Bacteriophage T4 Procapsids. Mol. Cell. 2007, 25, 943-949.
Tao, Y.; Olson, N. H.; Xu, W.; Anderson, D. L.; Rossmann, M. G.; Baker, T. S. Assembly of a Tailed Bacterial Virus and Its Genome Release Studied in Three Dimensions. Cell 1998, 95, 431-437.
Thieffry, M., Chich, J. F., Goldschmidt, D. & Henry, J. P. Incorporation in lipid bilayers of a large conductance cationic channel from mitochondrial membranes. EMBO J. 7, 1449-1454 (1988).
Trus B L, Cheng N, Newcomb W W, Homa F L, Brown J C, Steven A C (2004) Structure and polymorphism of the UL6 portal protein of herpes simplex virus type 1. J Virol 78: 12668-12671.
Uhlen, M. & Ponten, F., Antibody-based proteomics for human tissue profiling. Mol Cell Proteomics 4, 384-393 (2005).
Van Loon, A. M., et al. "Antibody-capture enzyme-linked immunosorbent assays that use enzyme-labelled antigen for detec-

(56) References Cited

OTHER PUBLICATIONS tion of virus-specific immunoglobulin M, A and G in patients with varicella or herpes zoster." Epidemiology & Infection 108.1 (1992): 165-174.
Venigalla B. Rao, A virus DNA gate: zipping and unzipping the packed viral genome. PNAS, 2009 106:8403-8404.
Venkatesan, B. M.; Bashir, R. Nanopore Sensors for Nucleic Acid Analysis. Nature Nanotechnology 2011, 6, 615-624.
Vercoutere, Wenonah A., et al. "Discrimination among individual Watson—Crick base pairs at the termini of single DNA hairpin molecules." Nucleic acids research 31.4 (2003): 1311-1318.
Vercoutere, Wenonah, et al. "Rapid discrimination among individual DNA hairpin molecules at single-nucleotide resolution using an ion channel." Nature biotechnology 19.3 (2001): 248.
Wang, H. Y. et al., Nanopore analysis of beta-amyloid peptide aggregation transition induced by small molecules. Anal. Chem. 83, 1746-1752 (2011).
Wang, Hui, and Daniel Branton. "Nanopores with a spark for single-molecule detection." (2001): 622.
Wang, L., Han, Y., Zhou, S. & Guan, X., Real-time label-free measurement of HIV-1 protease activity by nanopore analysis. Biosens. Bioelectron. 62, 158-162 (2014).
Wang, S. et al., Engineered Nanopore of Phi29 DNA-Packaging Motor for Real-Time Detection of Single Colon Cancer Specific Antibody in Serum. ACS Nano 7, 9814-9822 (2013).
Wang, Y. et al., Nanopore sensing of botulinum toxin type B by discriminating an enzymatically cleaved Peptide from a synaptic protein synaptobrevin 2 derivative. ACS Appl. Mater. Interfaces 7, 184-192 (2015).
Wen, S. et al., Highly sensitive and selective DNA-based detection of mercury(II) with alpha-hemolysin nanopore. J. Am. Chem. Soc. 133, 18312-18317 (2011).
Woo, Eileen M., et al. "Efficient identification of phosphorylation by mass spectrometric phosphopeptide fingerprinting." Analytical chemistry 80.7 (2008): 2419-2425.
Xiang, Y.; Morais, M. C.; Battisti, A. J.; Grimes, S.; Jardine, P. J.; Anderson, D. L.; Rossmann, M. G. Structural Changes of Bacteriophage Phi29 Upon DNA Packaging and Release. EMBO J. 2006, 25, 5229-5239.
Xiao, F.; Zhang, H.; Guo, P. Novel Mechanism of Hexamer Ring Assembly in Protein/RNA Interactions Revealed by Single Molecule Imaging. Nucleic Acids Res 2008, 36, 6620-6632.
Xu, Hua, et al. "Serotype 1-specific monoclonal antibody-based antigen capture immunoassay for detection of circulating nonstructural protein NS1: implications for early diagnosis and serotyping of dengue virus infections." Journal of clinical microbiology 44.8 (2006): 2872-2878.
Yan, R.; Liang, W.; Fan, R.; Yang, P. Nanofluidic Diodes Based on Nanotube Heterojunctions. Nano Left. 2009, 9, 3820-3825.
Yin, Bei, et al. "Identification of fungal rDNA associated with soil suppressiveness against Heterodera schachtii using oligonucleotide fingerprinting." Phytopathology 93.8 (2003): 1006-1013.
Yu, J.; Moffitt, J.; Hetherington, C. L.; Bustamante, C.; Oster, G. Mechanochemistry of a Viral DNA Packaging Motor. J. Mol. Biol. 2010, 400, 186-203.
Zhao, H.; Finch, C. J.; Sequeira, R. D.; Johnson, B. A.; Johnson, J. E.; Casjens, S. R.; Tang, L. Crystal Structure of the DNA-Recognition Component of the Bacterial Virus Sf6 Genome-Packaging Machine. Proc. Natl. Acad. Sci. U.S.A 2010, 107, 1971-1976.
Zhao, Z.; Khisamutdinov, E.; Schwartz, C.; Guo, P. Mechanism of One-Way Traffic of Hexameric Phi29 DNA Packaging Motor With Four Electropositive Relaying Layers Facilitating Anti-Parallel Revolution. ACS Nano 2013, 7, 4082-4092.
Zheng, H.; Olia, A. S.; Gonen, M.; Andrews, S.; Cingolani, G.; Gonen, T. A Conformational Switch in Bacteriophage P22 Portal Protein Primes Genome Injection. Mol. Cell. 2008, 29, 376-383.
Agnew, W. S.; Simon, R. L.; Brabson, J. S.; Raftery, M. A. Purification of the Tetrodotoxin-Binding Component Associated With the Voltage-Sensitive Sodium Channel From Electrophorus Electricus Electroplax Membranes. Proceedings of the National Academy of Sciences of the United States of America 1978, 75, 2606-2610.
Aguilella, V. M.; Alcaraz, A. Nanobiotechnology: A Fluid Approach to Simple Circuits. Nat. Nanotechnol. 2009, 4, 403-404.
Alcayaga, C., Venegas, R., Carrasco, A. & Wolff, D. Ion channels from the Bacillus subtilis plasma-membrane incorporated into planar lipid bilayers. FEBS Lett. 311, 246-250 (1992).
Archakov, A. I., Ivanov, Y. D., Lisitsa, A. V. & Zgoda, V. G., AFM fishing nanotechnology is the way to reverse the Avogadro number in proteomics. Proteomics 7, 4-9 (2007).
Asandei, A. et al., Probing of various physiologically relevant metals-amyloid-beta peptide interactions with a lipid membrane-immobilized protein nanopore [corrected]. J. Membr. Biol. 247, 523-530 (2014).
Astier, Y.; Braha, O.; Bayley, H. Toward Single Molecule DNA Sequencing: Direct Identification of Ribonucleoside and Deoxyribonucleoside 5'-Monophosphates by Using an Engineered Protein Nanopore Equipped With a Molecular Adapter. J. Am. Chem. Soc. 2006, 128, 1705-1710.
Astumian, R. D. Thermodynamics and Kinetics of a Brownian Motor. Science 1997, 276, 917-922.
Barnham, K. J. et al., Platinum-based inhibitors of amyloid-beta as therapeutic agents for Alzheimer's disease. Proc. Natl. Acad. Sci. U.SA 105, 6813-6818 (2008).
Benz, R., Schmid, A., Nakae, T. & Vosscherperkeuter, G. H. Pore formation by LamB of *Escherichia coli* in lipid bilayer membranes. J. Bacteriol. 165, 978-986 (1986).
Bertil Hille Ion Channels of Excitable Membranes; Sinauer Associates, Inc.: 2001.
Braha, O.; Walker, B.; Cheley, S.; Kasianowicz, J. J.; Song, L.; Gouaux, J. E.; Bayley, H. Designed Protein Pores as Components for Biosensors. Chemistry & Biology 4, 497-505. 7-1-1997. Ref Type: Abstract.
Branton, D. et al., The potential and challenges of nanopore sequencing. Nat. Biotechnol. 26, 1146-1153 (2008).
Brinker, James P., et al. "Detection of Norwalk virus and other genogroup 1 human caliciviruses by a monoclonal antibody, recombinantantigen-based immunoglobulin M capture enzyme immunoassay." Journal of clinical microbiology 36.4 (1998): 1064-1069.
Brown, T. M., et al. "Detection of eastern equine encephalitis virus in infected mosquitoes using a monoclonal antibody-based antigen-capture enzyme-linked immunosorbent assay." The American journal of tropical medicine and hygiene 65.3 (2001): 208-213.
Butler, T. Z.; Pavlenok, M.; Derrington, I. M.; Niederweis, M.; Gundlach, J. H. Single-Molecule DNA Detection With an Engineered MspA Protein Nanopore. Proc. Natl. Acad. Sci. U.S.A 2008, 105, 20647-20652.
Cal, Y.; Xiao, F.; Guo, P. The Effect of N- or C-Terminal Alterations of the Connector of Bacteriophage Phi29 DNA Packaging Motor on Procapsid Assembly, PRNA Binding, and DNA Packaging. Nanomedicine 2008, 4, 8-18.
Carneiro, Carlos MM, et al. "Probing the volume changes during voltage gating of Porin 31BM channel with nonelectrolyte polymers." Biochimica et Biophysica Acta (BBA)-Biomembranes 1612.2 (2003): 144-153.
Chang, H. et al., DNA counterion current and saturation examined by a MEMS-based solid state nanopore sensor. Biomed. Microdevices. 8, 263-269 (2006).
Che, Xiao-yan, et al. "Sensitive and specific monoclonal antibody-based capture enzyme immunoassay for detection of nucleocapsid antigen in sera from patients with severe acute respiratory syndrome." Journal of clinical microbiology 42.6 (2004): 2629-2635.
Chemla, Y. R. et al. Mechanism of force generation of a viral DNA packaging motor. Cell 122, 683-692 (2005).
Chen, C.; Guo, P. Sequential Action of Six Virus-Encoded DNA-Packaging RNAs During Phage Phi29 Genomic DNA Translocation. J. Virol. 1997, 71, 3864-3871.
Chen, C.; Sheng, S.; Shao, Z.; Guo, P. A Dimer as a Building Block in Assembling RNA: A Hexamer That Gears Bacterial Virus Phi29 DNA-Translocating Machinery. J Biol Chem 2000, 275(23), 17510-17516.

(56) References Cited

OTHER PUBLICATIONS

Chen, M., Khalid, S., Sansom, M. S. & Bayley, H., Outer membrane protein G: Engineering a quiet pore for biosensing. Proc. Natl. Acad. Sci. U.S.A 105, 6272-6277 (2008).
Cingolani, G.; Moore, S. D.; Prevelige, J.; Johnson, J. E. Preliminary Crystallographic Analysis of the Bacteriophage P22 Portal Protein. J Struct Biol 2002, 139, 46-54.
Clarke, J.; Wu, H. C.; Jayasinghe, L.; Patel, A.; Reid, S.; Bayley, H. Continuous Base Identification for Single-Molecule Nanopore DNA Sequencing. Nat. Nanotechnol. 2009, 4, 265-270.
Damodaran, Senthilkumar, et al. "Evaluating peptide mass fingerprinting-based protein identification." Genomics, proteomics & bioinformatics 5.3-4 (2007): 152-157.
David, C., Foley, S. & Enescu, M., Protein S-S bridge reduction: a Raman and computational study of lysozyme interaction with TCEP. Phys Chem. Chem. Phys 11, 2532-2542 (2009).
De-Donatis, G.; Zhao, Z.; Wang, S.; Huang, P. L.; Schwartz, C.; Tsodikov, V. O.; Zhang, H.; Hague, F.; Guo, P. Finding of Widespread Viral and Bacterial Revolution DsDNA Translocation Motors Distinct From Rotation Motors by Channel Chirality and Size. Cell Biosci 2014, 4, 30.
DeGuzman, Veronica S., et al. "Sequence-dependent gating of an ion channel by DNA hairpin molecules." Nucleic acids research 34.22 (2006): 6425-6437.
Dorogi, P. L; Neumann, E. Theoretical Implication of Liganding Reactions in Axonal Sodium Channel Gating. Neurochemistry International 1980, 2, 45-51.
Dryden, K.; Wang, G.; Yeager, M.; Nibert, M.; Coombs, K.; Furlong, D.; Fields, B.; Baker, T. Early Steps in Reovirus Infection Are Associated With Dramatic Changes in Supramolecular Structure and Protein Conformation: Analysis of Virions and Subviral Particles by Cryoelectron Microscopy and Image Reconstruction. J Cell Biol 1993, 122, 1023-1041.
Dube P, Tavares P, Lurz R, van Heel M (1993) The portal protein of bacteriophage SPP1: a DNA pump with 13-fold symmetry. EMBO J 12: 1303-1309.
Fan, J. et al., Nanopore film based enrichment and quantification of low abundance hepcidin from human bodily fluids. Nanomedicine. 10, 879-888 (2014).
Fang, H., Jing, P., Haque, F. & Guo, P., Role of channel Lysines and "Push Through a One-way Valve" Mechanism of Viral DNA packaging Motor. Biophysical Journal 102, 127-135 (2012).
Fang, Y.; Shu, D.; Xiao, F.; Guo, P.; Qin, P. Z. Modular Assembly of Chimeric Phi29 Packaging RNAs That Support DNA Packaging. Biochemical and Biophysical Research Communications 2008, 372, 589-594.
Fologea, D., Ledden, B., McNabb, D. S. & Li, J., Electrical characterization of protein molecules by a solid-state nanopore. Appl. Phys Lett. 91, 539011-539013 (2007).
Fujisawa, H.; Morita, M. Phage DNA Packaging. Genes Cells 1997, 2, 537-545.
Gracheva, M. E.; Vidal, J.; Leburton, J. P. P-n. Semiconductor Membrane for Electrically Tunable Ion Current Rectification and Filtering. Nano Lett. 2007, 7, 1717-1722.
Guasch, A.; Pous, J.; Ibarra, B.; Gomis-Ruth, F. X.; Valpuesta, J. M.; Sousa, N.; Carrascosa, J. L.; Coll, M. Detailed Architecture of a DNA Translocating Machine: the High-Resolution Structure of the Bacteriophage Phi29 Connector Particle. J. Mol. Biol. 2002, 315, 663-676.
Guo, P. et al., Common Mechanisms of DNA translocation motors in Bacteria and Viruses Using One way Revolution Mechanism without Rotation. Biotechnology Advances 32, 853-872 (2014).
Guo, P. X.; Lee, T. J. Viral Nanomotors for Packaging of DsDNA and DsRNA. Mol. Microbiol. 2007, 64, 886-903.
Guo, P.; Erickson, S.; Xu, W.; Olson, N.; Baker, T. S.; Anderson, D. Regulation of the Phage F29 Prohead Shape and Size by the Portal Vertex. Virology 1991, 183, 366-373.
Haque, F. et al., Real-Time Sensing and Discrimination of Single Chemicals Using the Channel of Phi29 DNA Packaging Nanomotor. ACS Nano 6, 3251-3261 (2012).
Haque, F. et al., Single pore translocation of folded, double-stranded, and tetra-stranded DNA through channel of bacteriophage Phi29 DNA packaging motor. Biomaterials 53, 744-752 (2015).
Haque, F. et al., Solid-state and biological nanopore for real-time sensing of single chemical and sequencing of DNA. Nano Today 8, 56-74 (2013).
Haque, F.; Geng, J.; Montemagno, C.; Guo, P. Incorporation of Viral DNA Packaging Motor Channel in Lipid Bilayers for Real-Time, Single-Molecule Sensing of Chemicals and Double-Stranded DNA. Nat. Protoc. 2013, 8, 373-392.
Harlow and Lane, Antibodies: A Laboratory Manual, Cold Spring Harbor Laboratory, 1988.
He, Qigai, et al. "Detection of H5 avian influenza viruses by antigen-capture enzyme-linked immunosorbent assay using H5-specific monoclonal antibody." Clin. Vaccine Immunol. 14.5 (2007): 617-623.
Hendrix, R. W. Symmetry Mismatch and DNA Packaging in Large Bacteriophages. Proc. Natl. Acad. Sci. USA 1978, 75, 4779-4783.
Hierholzer, J. C., et al. "Comparison of monoclonal antibody time-resolved fluoroimmunoassay with monoclonal antibody capture-biotinylated detector enzyme immunoassay for respiratory syncytial virus and parainfluenza virus antigen detection." Journal of clinical microbiology 27.6 (1989): 1243-1249.

* cited by examiner a. Oxidation-dimer b. Reduction-monomer c. Cy3 conjugate-monomer

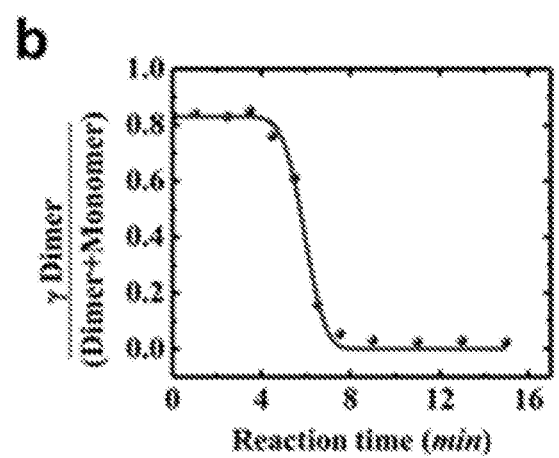
FIG. 6, Cont'd

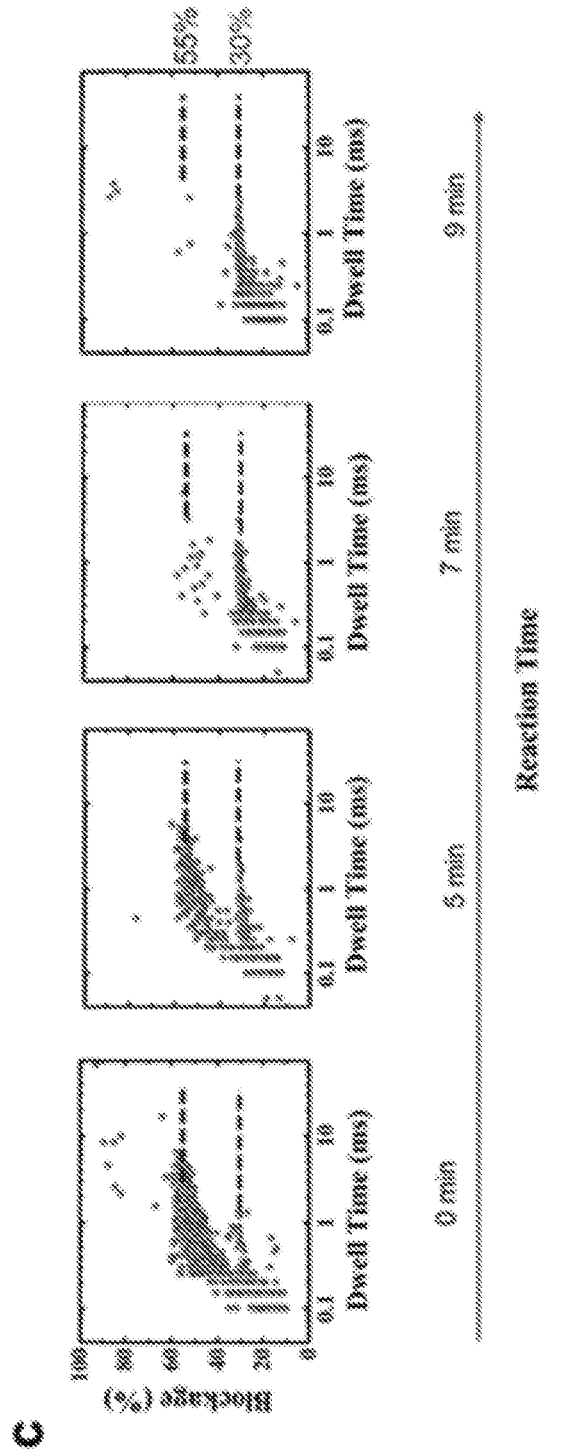
FIG. 6, Cont'd

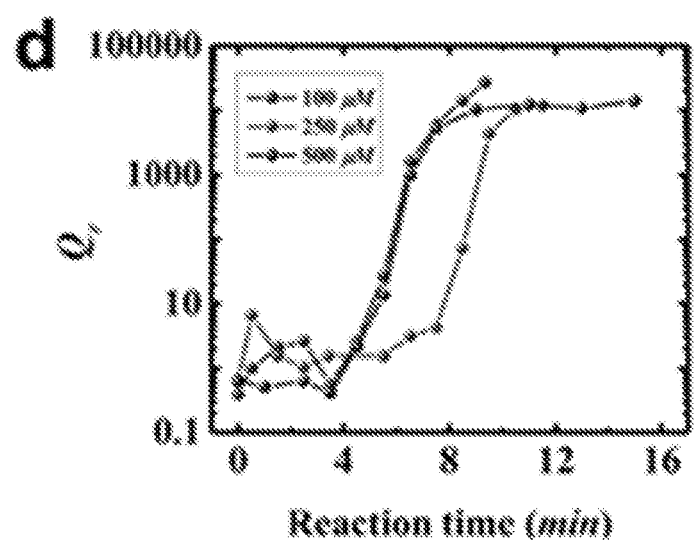
FIG. 6, Cont'd a. BSA (MW: 60 kD)

b. SPP1 connector (MW: 58 kD)

LIPID BILAYER-INTEGRATED SPP1 CONNECTOR PROTEIN NANOPORE AND SPP1 CONNECTOR PROTEIN VARIANTS FOR USE AS LIPID BILAYER-INTEGRATED NANOPORE

RELATED APPLICATIONS

This application is a § 371 National State Application of PCT/CN2016/013702 filed Jan. 15, 2016, which claims priority from U.S. Provisional Application Ser. No. 62/104,375 filed Jan. 16, 2015, the entire disclosure of which are incorporated herein by this reference.

GOVERNMENT INTEREST

This invention was made with government support under EB012135 and EB003730 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jul. 13, 2017, is named 2935720-3_SL.txt and is 34,432 bytes in size.

TECHNICAL FIELD

The presently-disclosed subject matter relates to an engineered SPP1 viral DNA-packaging motor connector protein that can be incorporated into a lipid membrane to form an electroconductive aperture.

BACKGROUND

Highly sensitive detection and characterization of minute quantities of chemicals and biochemicals represent desirable goals of modern analytical technologies. Robust molecular sensing devices would find uses in a wide range of biomedical, industrial, environmental, forensic, security and other contexts, for example, in the detection and identification of pathogens and chemicals at extremely low concentrations for disease diagnosis and environmental monitoring, in high throughput DNA sequencing and other genomics applications, and elsewhere.

Analytical methodologies have been described that employ intermolecular affinity binding interactions, typically non-covalent in nature, to detect binding or "capture" of an analyte of interest by a specific affinity ligand, for instance, including detection of bacterial, viral, parasitic or other microbial pathogens or pathogen-associated antigens, and detection of antibodies, cancer markers, and other analytes (e.g., Kittigul et al., Am J Trop Med Hyg. 1998 September; 59(3):352-6; Cordiano et al., J Immunol Methods. 1995 Jan. 13; 178(1):121-30; Olson et al., J Immunol Methods. 1990 Nov. 6; 134(1):71-9; Nerurkar et al., J Clin Microbiol. 1984 July; 20(1):109-14; Jia et al., J Virol Methods. 2009 October; 161(1):38-43; He et al., Clin Vaccine Immunol. 2007 May; 14(5):617-23; Xu et al., J Clin Microbiol. 2006 August; 44(8):2872-8; Che et al., J Clin Microbiol. 2004 June; 42(6):2629-35; Hunt et al., Brown et al., Am J Trop Med Hyg. 2001 September; 65(3):208-13; Loa et al., Avian Dis. 2000 July-September; 44(3):498-506; Lubenko et al., Transfus Med. 2000 September; 10(3):213-8; Chanteau et al., Int J Tuberc Lung Dis. 2000 April; 4(4):377-83; Brinker et al., J Clin Microbiol. 1998 April; 36(4):1064-9; Vyse et al., J Virol Methods. 1997 January; 63(1-2):93-101; Peterson et al., J Clin Microbiol. 1997 January; 35(1):208-12; Lairmore et al., AIDS Res Hum Retroviruses. 1993 June; 9(6):565-71; Heller et al., Vet Microbiol. 1993 October; 37(1-2):127-33; van Loon et al., Epidemiol Infect. 1992 February; 108(1):165-74; Wolf-Rogers et al., J Immunol Methods. 1990 Oct. 19; 133(2):191-8; Barsoum et al., Exp Parasitol. 1990 July; 71(1):107-13; Hierholzer et al., J Clin Microbiol. 1989 June; 27(6):1243-9; Hurley et al., J Immunoassay. 1986; 7(4):309-36; Wolff et al., Cancer Res. 53:2560-65 (1993); see generally, e.g., Harlow and Lane, Antibodies: A Laboratory Manual, Cold Spring Harbor Laboratory, 1988; Weir, D. M., Handbook of Experimental Immunology, 1986, Blackwell Scientific, Boston, Mass.).

Beyond detection of the presence of an analyte following its involvement in an affinity binding interaction, sophisticated technologies are emerging that permit characterization of the analyte, often by comparing a single- or multiparameter physicochemical profile of the analyte to type-characteristic profiles generated using one or more known reference standards, and hence referred to as "fingerprinting" techniques (e.g., Li et al., Rapid Commun Mass Spectrom. 2009 23(22):3533-3542; Ali et al., J Agric Food Chem. 2009; Leski et al., Appl Environ Microbiol. Sep. 18, 2009; Weinkopff et al., J Parasitol. Jun. 18, 2009; Song et al., Proteomics. 2009 9(11):3090-9; Ortea et al., J Agric Food Chem. 2009 57(13):5665-72; Amini, Pharmeur Sci Notes. 2009(1):11-6; Shi et al., Biol Pharm Bull. 2009 32(1):142-6; Sun et al., J Chromatogr A. 2009 1216(5):830-6; Yin et al., Phytopathology. 2003 93(8):1006-13; Roy et al., Clin Cancer Res. 2008 14(20):6610-7; Pei et al., Zhongguo Zhong Yao Za Zhi. 2008 33(14):1662-8; Arthur, Methods Mol Med. 2008, 141:257-70; Zhao et al., Se Pu 2008 26(1):43-9; Woo et al., Anal Chem. 2008 80(7):2419-25; Damodaran et al., Genomics Proteomics Bioinformatics. 2007 5(3-4):152-7; Fellstrom et al., J Microbiol Methods. 2008 72(2):133-40; Song et al., Conf Proc IEEE Eng Med Biol Soc. 2006 1:4556-9; De Vuyst et al., Int J Food Microbiol. 2008 125(1):79-90).

The use of transmembrane channels has been demonstrated in stochastic analyte detection (Bayley et al., 2001 Nature 13:225-230), an electrochemical approach relying on the real-time observation of individual binding events between single substrate molecules and a receptor, as evidenced by altered (e.g., decreased or increased in a statistically significant manner) electrical conductance by the channel (receptor) as a result of substrate (analyte) binding. A wide range of processes, such as the transport of DNA, RNA, pharmaceutical agents, peptides, proteins, and polymers, have been studied by such approaches, for example, using electrophysiological measurements of individual membrane channels (Thieffry et al., 1988 EMBO J 7:1449; Hinnah et al., 2002 Biophys J 83:899; Alcayaga et al., 1992 FEBS Lett. 311:246-50; Benz et al., 1986 J Bacteriol 165: 978; Movileanu et al., 2000 Nat. Biotechnol. 18:1091).

For instance, the transient blockade of ionic current through the *Staphylococcus aureus* alpha-hemolysin (α-HL) channel, a bacterial transmembrane pore-forming protein, has been used to measure the length of single-stranded DNA or RNA (Kasianowicz et al. Proc. Natl. Acad. Sci. USA 93, 13770-13773 (1996)). Subsequently, DNA hairpin molecules have been used to decelerate the DNA translocation rate through the alpha-hemolysin (α-HL) pore, to demonstrate the ability of a transmembrane ion channel to discriminate between single nucleotide polymorphisms (Vercoutere et al., 2001 Nat. Biotechnol. 19:248). Detection of base pair stacking and strand orientation within the pore have also been investigated (Vercoutere et al., 2003 Nucl Ac. Res. 31:1311; Howorka et al., 2001 Nat. Biotechnol. 19:636; deGuzman et al., 2006 Nucl. Ac. Res. 34:6425). The channel of α-HL with a covalently attached adapter molecule has been shown to discriminate the nucleotides A, T, G, and C (Clarke et al., 2009 Nat. Nanotechnol. 4:265).

The α-HL channel has also been reported to provide some ability to translocate small peptides (See e.g., Mohammad, et al., "Protein Sensing with engineered protein nanopores," Methods Mol Biol. 2012, 870:21-37; Jetha, et al., "Nanopore Analysis of Wild-Type and Mutant Prion Protein (PrPc): Single Molecule Discrimination and PrPc Kinetics," PLOS ONE, 2013, 8(2); Mereuta, et al., "Slowing down single-molecule trafficking through a protein nanopore reveals intermediates for peptide translocation," Scientific Reports, 2014, 4:3885; Rosen, et al., "Single-molecule site-specific detection of protein phosphorylation with a nanopore," Nat Biotechnol, 2014 February, 32(2):179-81); Movileanu, "Watching single proteins using engineered nanopores," Protein Pept Lett. 2014 March, 21(3):235-46). However, at only about 1.2-1.5 nm, only a limited number of peptides are capable of being translocated through the α-HL channel and there is not an ability to differentiate between different peptides.

Other protein channels that have been investigated include alamethicin for detection of polyethylene glycol (Bezrukov, 2000 J Membr Biol. 174:1-13), and the reengineered MspA protein from *M. smegmatis* for translocation of ssDNA (Butler et al., 2008 Proc. Nat. Acad. Sci. USA 105:20647). Most studies involving nucleic acid transport through nanopores have focused on α-HL. However, the limiting lumen diameter of α-HL (about 1.2-1.5 nm) and other channels has restricted their DNA and RNA applications to translocation of single-stranded nucleic acid (Song, 1996 Science 274:1859). A similar limitation was also reported for the MspA nanopore (Butler et al., 2008).

In a small number of other membrane pore systems, evidence of double-stranded DNA (dsDNA) transport across the membrane has been presented (Szabo et al., 2002 Cell Physiol Biochem 12:127; Mobasheri et al. 2002 Eur J Bipohys 31:389; Carneiro et al., 2003 Biochim Biophys Acta 1612:144), but these systems are not robust and represent poor candidates for widespread use such as biomedical applications, due to their undesirable voltage gating properties and the associated signal fluctuation. For this reason, their potential is considered limited and researchers have switched instead to fabricating synthetic metal or silicon nanopores for potential use in DNA sequencing (Smeets et al, 2006 Nano Lett 6:89; Wang et al., 2001 Nat. Biotechnol. 19:622; lqbal et al., 2007 Nat. Nano 2:243). Such synthetic nanopores, however, suffer from shortcomings due to difficulties in reliably producing replicated structures having consistent properties from batch to batch, and also lack versatility with regard to the ability to engineer modifications to pore structures and/or to serve as substrates for modification by a wide range of chemical conjugation. As a result, the search for superior alternatives to currently available protein nanopores is still ongoing.

There is a need for improved compositions and methods that would provide a versatile membrane conductive channel platform for sensitively detecting and characterizing a wide range of analytes, having a lumen capable of accommodating dsDNA and polypeptides, that can be reliably and reproducibly assembled, that is not susceptible to voltage gating under working conditions, and that can be readily modified to feature a wide variety of specific affinity receptors for use in the detection and characterization of different analytes. The presently disclosed invention embodiments fulfill such a need, and offer other related advantages.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes a nucleic acid molecule encoding an SPP1 connector polypeptide variant. In some embodiments, the SPP1 connector polypeptide variant comprises an amino acid sequence having at least 95% sequence identity to the sequence shown in SEQ ID NO:4, SEQ ID NO:6, SEQ ID NO:8, or SEQ ID NO:10. In some embodiments, the SPP1 connector polypeptide variant comprises an amino acid sequence having at least 95% sequence identity to the sequence of SEQ ID NO:4, SEQ ID NO:6, SEQ ID NO:8, or SEQ ID NO:10. In some embodiments, the SPP1 connector polypeptide variant comprises an amino acid sequence having at least 99% sequence identity to the sequence of in SEQ ID NO:4, SEQ ID NO:6, SEQ ID NO:8, or SEQ ID NO:10. In some embodiments, the SPP1 connector polypeptide variant comprises the amino acid sequence of SEQ ID NO:4, SEQ ID NO:6, SEQ ID NO:8, or SEQ ID NO:10. In some embodiments, the nucleic acid molecule encoding an SPP1 connector polypeptide variant includes the sequence of SEQ ID NO:3, SEQ ID NO:5, SEQ ID NO:7, or SEQ ID NO:9.

The presently disclosed subject matter further includes a SPP1 connector polypeptide variant, wherein the polypeptide comprises an amino acid sequence having at least 95% sequence identity to the sequence of SEQ ID NO:4, SEQ ID NO:6, SEQ ID NO:8, or SEQ ID NO:10. at least 95% sequence identity to the sequence shown in SEQ ID NO:4, SEQ ID NO:6, SEQ ID NO:8, or SEQ ID NO:10. In some embodiments, the SPP1 connector polypeptide variant comprises an amino acid sequence having at least 95% sequence identity to the sequence of SEQ ID NO:4, SEQ ID NO:6, SEQ ID NO:8, or SEQ ID NO:10. In some embodiments, the SPP1 connector polypeptide variant comprises an amino acid sequence having at least 99% sequence identity to the sequence of in SEQ ID NO:4, SEQ ID NO:6, SEQ ID NO:8, or SEQ ID NO:10. In some embodiments, the SPP1 connector polypeptide variant comprises the amino acid sequence of SEQ ID NO:4, SEQ ID NO:6, SEQ ID NO:8, or SEQ ID NO:10.

The presently disclosed subject matter further includes a SPP1 connector polypeptide variant, wherein the polypeptide comprises an amino acid sequence encoded by a nucleic acid molecule having the sequence of SEQ ID NO:3, SEQ ID NO:5, SEQ ID NO:7, or SEQ ID NO:9.

The presently disclosed subject matter further includes a conductive channel-containing membrane, which includes (a) a membrane layer, and (b) a SPP1 connector polypeptide variant that is incorporated into the membrane layer to form an aperture through which conductance can occur when an electrical potential is applied across the membrane.

In some embodiments the SPP1 connector polypeptide variant of the conductive channel-containing membrane is selected from (i) a polypeptide comprising an amino acid sequence having at least 95% sequence identity to the sequence of SEQ ID NO:4, SEQ ID NO:6, SEQ ID NO:8, or SEQ ID NO:10; (ii) a polypeptide comprising an amino acid sequence having at least 99% sequence identity to the sequence of SEQ ID NO:4, SEQ ID NO:6, SEQ ID NO:8, or SEQ ID NO:10; (iii) a polypeptide comprising the amino acid sequence of SEQ ID NO:4, SEQ ID NO:6, SEQ ID NO:8, or SEQ ID NO:10; and (iv) a polypeptide comprising an amino acid sequence encoded by a nucleic acid molecule having the sequence of SEQ ID NO:3, SEQ ID NO:5, SEQ ID NO:7, or SEQ ID NO:9.

In some embodiments of the conductive channel-containing membrane the SPP1 connector polypeptide variant comprises a detectable label. In some embodiments of the conductive channel-containing membrane, the detectable label is selected from the group consisting of a colorimetric indicator, a (iCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label.

In some embodiments of the conductive channel-containing membrane, the membrane layer comprises a lipid layer. In some embodiments, the lipid layer comprises amphipathic lipids. In some embodiments, the amphipathic lipids comprise phospholipids and the lipid layer comprises a lipid bilayer. In some embodiments, the lipid layer is selected from the group consisting of a planar membrane layer and a liposome. In some embodiments, the liposome is selected from the group consisting of a multilamellar liposome and a unilamellar liposome. In some embodiments, the incorporated SPP1 connector polypeptide variant is mobile in the membrane layer.

In some embodiments, the conductive channel-containing membrane is capable of translocating a single stranded nucleic acid molecule, a double-stranded nucelic acid molecule, and/or a polypeptide through the aperture when the electrical potential is applied, wherein said conductive channel-containing membrane is capable of polypeptide detection, identification, sequencing, and discrimination.

The presently-disclosed subject matter further includes a method of sensing a molecule using a conductive channel-containing membrane as disclosed herein. In some embodiments, the molecule is a polypeptide. In some embodiments, the molecule is a nucleic acid molecule. In some embodiments, the nucleic acid molecule is a double-stranded nucleic acid molecule.

The presently-disclosed subject matter further includes a method of DNA sequencing using a conductive channel-containing membrane as disclosed herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

BRIEF DESCRIPTION OF THE SEQUENCE LISTING

Figure 1:
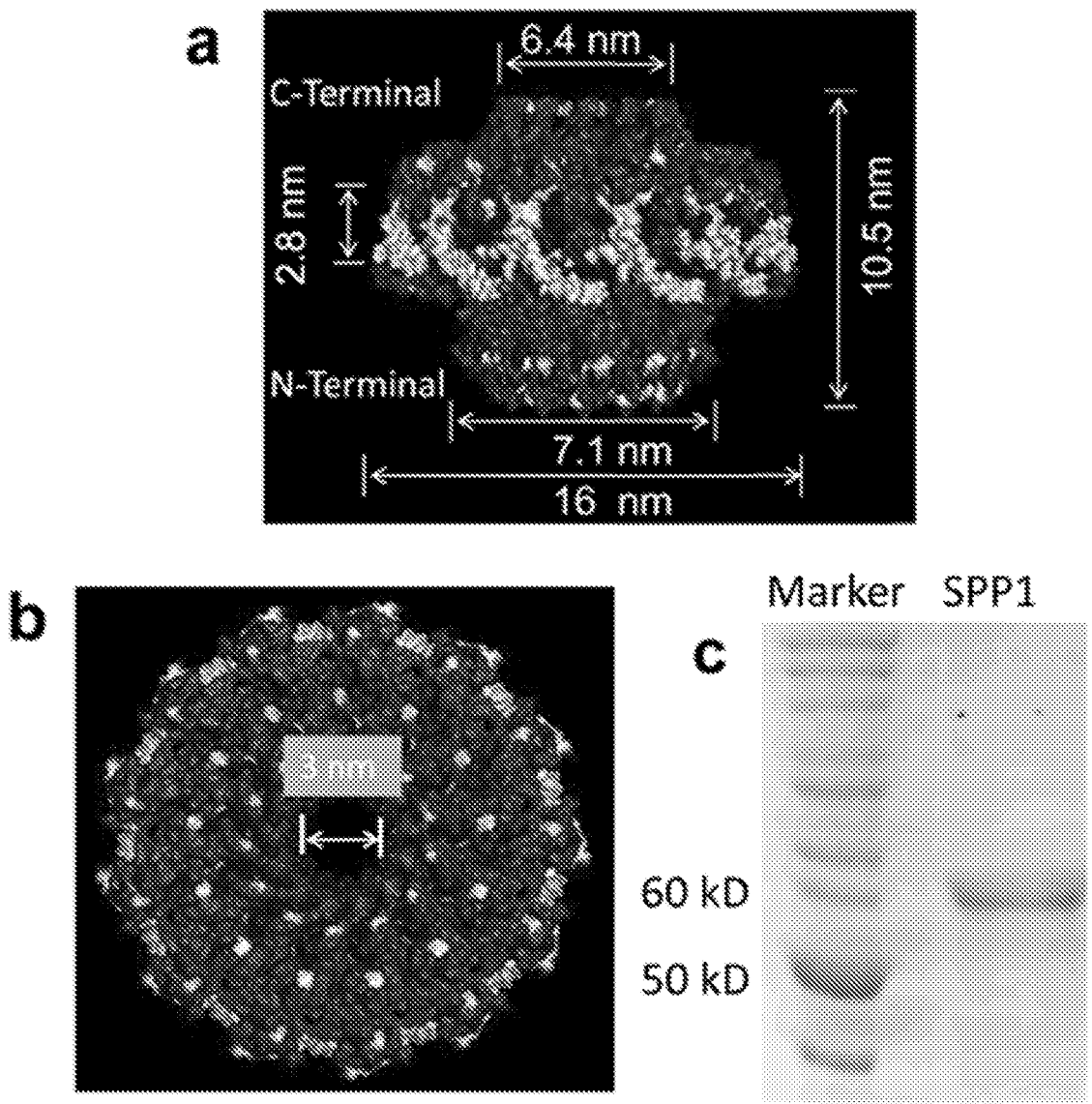
FIG. 1: Structure of the channel of SPP1 DNA packaging motor. (a) Side view and (b) top view from PDB file 2JES showing hydrophilic (red), hydrophobic (blue) and neutral (white) amino acids; and dimensions of the channel (PDB: 2JES). (c) Coomasie-blue stained SDS PAGE showing the purified SPP1 channel subunits gp6.

SEQ ID NO: 1 is the nucleic acid sequence of a nucleotide encoding a wild type SPP1 connector channel polypeptide.

SEQ ID NO: 2 is the amino acid sequence of a wild type SPP1 connector channel polypeptide.

SEQ ID NO: 3 is the nucleic acid sequence of a nucleotide encoding an exemplary SPP1 connector channel polypeptide variant.

SEQ ID NO: 4 is the amino acid sequence of the exemplary SPP1 connector channel polypeptide variant encoded by the nucleotide of SEQ ID NO: 3.

SEQ ID NO: 5 is the nucleic acid sequence of a nucleotide encoding another exemplary SPP1 connector channel polypeptide variant.

SEQ ID NO: 6 is the amino acid sequence of the exemplary SPP1 connector channel polypeptide variant encoded by the nucleotide of SEQ ID NO: 5.

SEQ ID NO: 7 is the nucleic acid sequence of a nucleotide encoding another exemplary SPP1 connector channel polypeptide variant.

SEQ ID NO: 8 is the amino acid sequence of the exemplary SPP1 connector channel polypeptide variant encoded by the nucleotide of SEQ ID NO: 7.

SEQ ID NO: 9 is the nucleic acid sequence of a nucleotide encoding another exemplary SPP1 connector channel polypeptide variant.

SEQ ID NO: 10 is the amino acid sequence of the exemplary SPP1 connector channel polypeptide variant encoded by the nucleotide of SEQ ID NO: 9.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes, in some embodiments, a nucleic acid molecule encoding an SPP1 connector polypeptide variant. The SPP1 connector polypeptide variant can comprises an amino acid sequence having at least 90, 91, 92, 93, 94, 95, 96, 97, or 99% sequence identity to a sequence shown in SEQ ID NO:4, SEQ ID NO:6, SEQ ID NO:8, or SEQ ID NO:10. In some embodiments, the nucleic acid molecule encodes a SPP1 connector polypeptide variant comprising an amino acid sequence as set forth in SEQ ID NO:4, SEQ ID NO:6, SEQ ID NO:8, or SEQ ID NO:10. In some embodiments, the nucleic acid molecule has the sequence shown in SEQ ID NO:3, SEQ ID NO:5, SEQ ID NO:7, or SEQ ID NO:9.

The presently-disclosed subject matter further includes, in some embodiments, a SPP1 connector polypeptide variant comprising an amino acid sequence having at least 90, 91, 92, 93, 94, 95, 96, 97, or 99% sequence identity to a sequence shown in SEQ ID NO:4, SEQ ID NO:6, SEQ ID NO:8, or SEQ ID NO:10. In some embodiments, the SPP1 connector polypeptide variant comprises an amino acid sequences as set forth in SEQ ID NO:4, SEQ ID NO:6, SEQ ID NO:8, or SEQ ID NO:10. In some embodiments, the SPP1 connector polypeptide variant comprises an amino acid sequence encoded by a nucleic acid molecule having the sequence shown in SEQ ID NO:3, SEQ ID NO:5, SEQ ID NO:7, or SEQ ID NO:9.

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence disclosed herein (e.g., SEQ ID NOs:1-10) and another sequence, the default parameters of the respective programs are used.

TABLE 1

Conservative Amino Acid Substitutions

| Amino Acid | Representative Conservative Amino Acids |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

Modifications, including substitutions, insertions or deletions are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

The presently-disclosed subject matter further includes, in some embodiments, a conductive channel-containing membrane, comprising (a) a membrane layer; and (b) a SPP1 connector polypeptide variant that is incorporated into the membrane layer to form an aperture through which conductance can occur when an electrical potential is applied across the membrane, wherein the SPP1 connector polypeptide variant is selected from among those disclosed herein.

Embodiments described herein find use in a variety of molecular analytical contexts, including, for example, sensitive detection and characterization of chemical and biochemical analytes for biomedical, clinical, industrial, chemical, pharmaceutical, environmental, forensic, national security, toxicological and other purposes, including any situation where rapid, specific and exquisitely sensitive detection and/or characterization of an analyte (e.g., preferably a soluble analyte that is provided in solution) may be desired. Expressly contemplated are embodiments in which the presently disclosed compositions and methods are used for DNA sequencing, including dsDNA sequencing, high-throughput DNA sequencing, genomics, SNP detection, molecular diagnostics and other DNA sequencing applications, and polypeptide detection and identification. Additional utilities include those described in International Patent Application Publication No. WO2010/062697, which is incorporated herein in its entirety by this reference.

Exemplary analytes thus include nucleic acids such as DNA and RNA (including dsDNA and dsRNA), including for the detection and identification of single nucleotide polymorphisms (SNPs) and/or mutations in such nucleic acids, and/or nucleic acid sequence determination. Other exemplary analytes that may be detected and/or characterized using the herein described compositions and methods include polypeptides and other biopolymers (e.g., proteins, glycoproteins, peptides, glycopeptides, oligosaccharides, polysaccharides, lipids, glycolipids, phospholipids, etc.) and other biomolecules (e.g., soluble mediators, cofactors, vitamins, bioactive lipids, metabolites, and the like), drugs and other pharmaceutical and pharmacological agents, including natural and synthetic compounds, food and cosmetics agents such as flavorants, odorants, preservatives, antioxidants, antimicrobial agents, stabilizers, carriers, excipients, modifying agents and the like, natural and synthetic toxins, dyes, and other compounds.

Accordingly and in certain embodiments, any analyte for which detection and/or characterization is desired may be used, where it will be recognized from the disclosure herein that the analyte is preferably soluble in a solvent that does not compromise the integrity of the particular membrane layer in which the SPP1 connector polypeptide variant is incorporated to form an aperture through which conductance can occur when an electrical potential is applied across the membrane. Analyte selection may thus vary as a function of the composition of the particular membrane layer being used, which may therefore influence solvent selection. Those skilled in the art will be familiar with criteria to be employed for selecting a solvent that is compatible with a membrane layer of any particular composition. In preferred embodiments, the membrane layer comprises a phospholipid bilayer and the solvent in which the analyte is provided comprises an aqueous solvent, e.g., a solvent that comprises water.

In some embodiments of the conductive channel-containing membrane, the membrane layer comprises a lipid layer. In a further embodiment the lipid layer comprises amphipathic lipids, which in certain still further embodiments comprise phospholipids and the lipid layer comprises a lipid bilayer. In certain other embodiments the lipid layer is selected from a planar membrane layer and a liposome. In certain embodiments the liposome is selected from a multilamellar liposome and a unilamellar liposome. In certain other embodiments the incorporated SPP1 connector polypeptide variant is mobile in the membrane layer. In certain other embodiments the conductive channel-containing membrane is capable of translocating double-stranded DNA through the aperture when the electrical potential is applied. In certain other embodiments the conductive channel-containing membrane is capable of translocating polypeptides through the aperture when the electrical potential is applied. In certain embodiments conductance occurs without voltage gating when the electrical potential is applied.

In some embodiments, the SPP1 connector polypeptide variant comprises a detectable label. In some embodiments, the detectable label is selected from the group consisting of a colorimetric indicator, a GCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

Although any methods, devices, and materials similar or equivalent to those described herein can be used in the practice or testing of the presently-disclosed subject matter, representative methods, devices, and materials are now described.

The presently-disclosed subject matter is further illustrated by the following specific but non-limiting examples. The following examples may include compilations of data that are representative of data gathered at various times during the course of development and experimentation related to the present invention.

EXAMPLES

Example 1

Nanopore of SPP1 DNA Packaging Motor for Dynamic Analysis of Protein Conformation and Folding in Real Time Information about conformation and folding of proteins can convey biological functions. A simple method to replace conventional sophisticated and labor-intensive methodology to detect protein conformation and kinetic folding in real time is desirable. While nanopore technology has become a powerful tool in single molecule sensing, protein nanopore appears more advantageous concerning channel amenability, structure homogeneity, and production reproducibility. However, most of the well-studied protein nanopores are ion channels with a pore size of only around 1.2-nm, which is too small to allow passage of protein or peptides that are typically in multiple nanometers scale. To acquire protein channels with larger pore sizes, we reengineered a robust portal channel from bacteriophage SPP1 that allowed the translocation of peptides with higher ordered structure to produce clear and reproducible electron signatures. By combining optical single molecule microscopy with resistive pulse technologies, we observed translocation of peptides quantitatively and analyzed their conformation and dynamic folding in real-time at single molecule level. The secondary structure and conformation, such as the oxidative and the reduced states, were directly and clearly differentiated. A similar $\Delta G^0$ was obtained when different concentrations of substrates were applied, suggesting that the use of SPP1 nanopore for real-time quantification of peptide folding is feasible. With the intrinsic nature of size and conjugation amenability, this SPP1 nanopore has the potential for development into a tool for the quantification of protein structure and folding in real time.

Living systems contain wide varieties of nanomachines with diverse structures and functions. The ingenious design of viral DNA packaging motors and their intriguing mechanism of action has provoked a wide range of interests among scientists in many different areas[1-5]. Tailed bacteriophages are viruses that infect and reproduce within a bacterium, and widely exist in the biosphere. The portal protein is one of the essential components of the viral packaging motors with a turbine-like shape[6, 7]. SPP1 is a dsDNA phage that infects *Bacillus subtilis*. The DNA packaging motor of SPP1 consists of a terminase composed of small (gp1) and large (gp2) subunits, portal protein gp6, and a two head completion proteins gp15 and gp16[8, 9] that powers the encapsulation of 45.9 kbp genomic DNA[10]. The central core of the SPP1 motor is a portal channel, termed connector, which is composed of 12 or 13 copies of protein gp6[9, 11]. Explicit engineering of the SPP1 portal protein is possible due to its available crystal structure[12, 13]. The connector has an overall diameter of 16 nm and a height of 10.5 nm. The narrowest constriction of the internal channel is ~3 nm (FIG. 1)[12, 13].

Nanopore technology has recently emerged as a real-time and high-throughput single molecule detection method, holding great potential for sensing a wide range of analytes, molecular diagnostics and DNA sequencing applications[14-23]. Solid state nanopores generated by microfabrication generally have less reproducible pore sizes and lack chemical and location selectivity. Protein nanopores harvested in bacteria are homogenous in size and can be functionalized with probes, but commonly used nanopores derived from ion channels have an internal channel diameter of only ~1.2 nm[24-27]. In search for alternative larger sized protein channels, we have previously developed membrane-embedded phi29 motor channels[28-30] for single molecule sensing of nucleic acids[28, 29, 31-34], chemicals[35], or binding assays of antibody based on channel conformational change[31, 36]. Herein, we reengineered the SPP1 connector and inserted it into a lipid bilayer to serve as a robust nanopore for detecting the translocation and conformational dynamics of peptides and proteins at single molecule level.

Elucidating the structural conformation and folding of proteins and peptides is critical for understanding their biological functions. A wide range of biophysical methods, such as X-ray crystallography, NMR, Circular Dichroism, Dual Polarization Interferometry, and Mass Spectrometry have been used to investigate folding and dynamic structural changes of proteins. However, these methods require expensive instrumentation and specialized labor. Nanopores offer an attractive alternative as they are intrinsically single molecule in nature requiring ultra-low sample volumes, are label free, amplification free, and function using a simple detection process requiring no specialized expertise. While the translocation of DNA and RNA have been studied extensively in biological nanopores[14, 16, 24, 37], studies on translocation of protein or peptides have just been emerged. This is mainly due to the size limitation of the commonly used protein pores, which are not large enough to allow the passage of proteins. The proteome can be an accurate and direct indicator of current health status of patients[38]. For example, early diagnosis and monitoring the changes of amyloid-β peptide and α-synuclein are critical for the management of Alzheimer's and Parkinson's disease[39].

A handful of studies demonstrating peptide translocation using nanopores have been published, but quantitative analysis and translocation validation remain challenging[40-47], since there is no technique available for amplifying protein substrates as in DNA or RNA qualification using PCR[48]. The availability of only trace amounts of peptide or protein for analysis after translocation is far beyond the sensitivity threshold of classical protein detection methods. In this report, we combined single molecule fluorescence microscopy and resistive pulse technique to quantitatively study peptide translocation through SPP1 connectors and elucidate the structural conformations of peptides at the single molecule level. This new nanopore peptide sensing technology with explicit engineering capabilities has the potential to transform the proteomics field, including future biomarker analysis, early disease diagnosis and even protein sequencing.

Results

Characterization of SPP1 Reengineered Nanopore Embedded in a Lipid Bilayer

Figure 7:
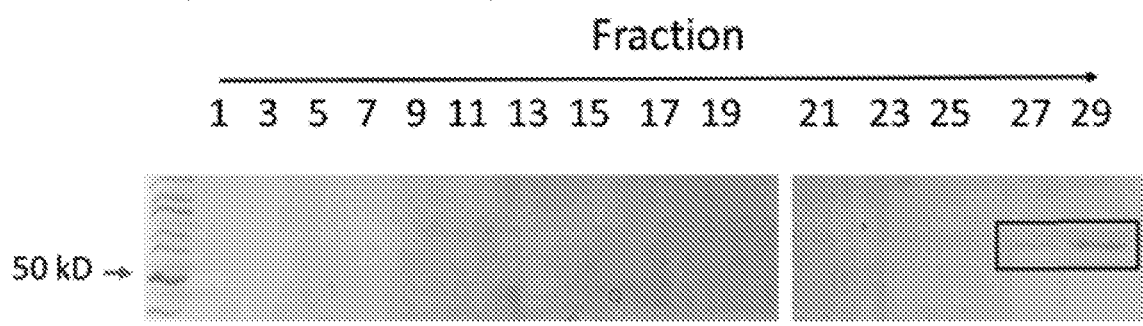
FIG. 7: Assembly of SPP1 gp6 subunits into 12 subunit connector complexes as shown by 15-35% glycerol gradient ultracentrifugation. BSA was used for size control.
Figure 7:
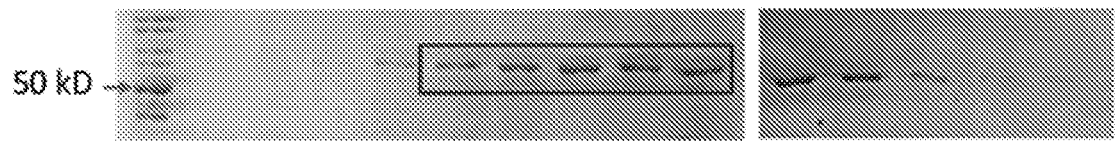

Structural analysis revealed that the central region of the SPP1 connector shows slight hydrophobicity compared with the flanking regions at the N- and C-terminal ends which are more hydrophilic (FIG. 1a-b). To facilitate SPP1 connector purification, a 6×His-tag (SEQ ID NO: 11) was inserted at the C-terminal end along with a 6×glycine linker fSEQ ID NO: 12) for end-flexibility. The presence of His-tag enhanced the hydrophilicity of the C-terminal, thus making the hydrophilichydrophobichydrophilic layers more distinct, which is necessary to mimic the lipid bilayer architecture. After His-tag column purification, the purified protein was further purified by 15-35% glycerol gradient ultracentrifugation to verify whether SPP1 subunit could assemble into the channel complex (FIG. 7). Bovine serum albumin (BSA) with molecular weight of 60 KDa, which is almost equal to a single subunit (58 KDa) of the SPP1 connector, centered at fraction 27, whereas the SPP1 portal complex was at fraction 17, indicating the formation of higher molecular weight complex.

Figure 2:
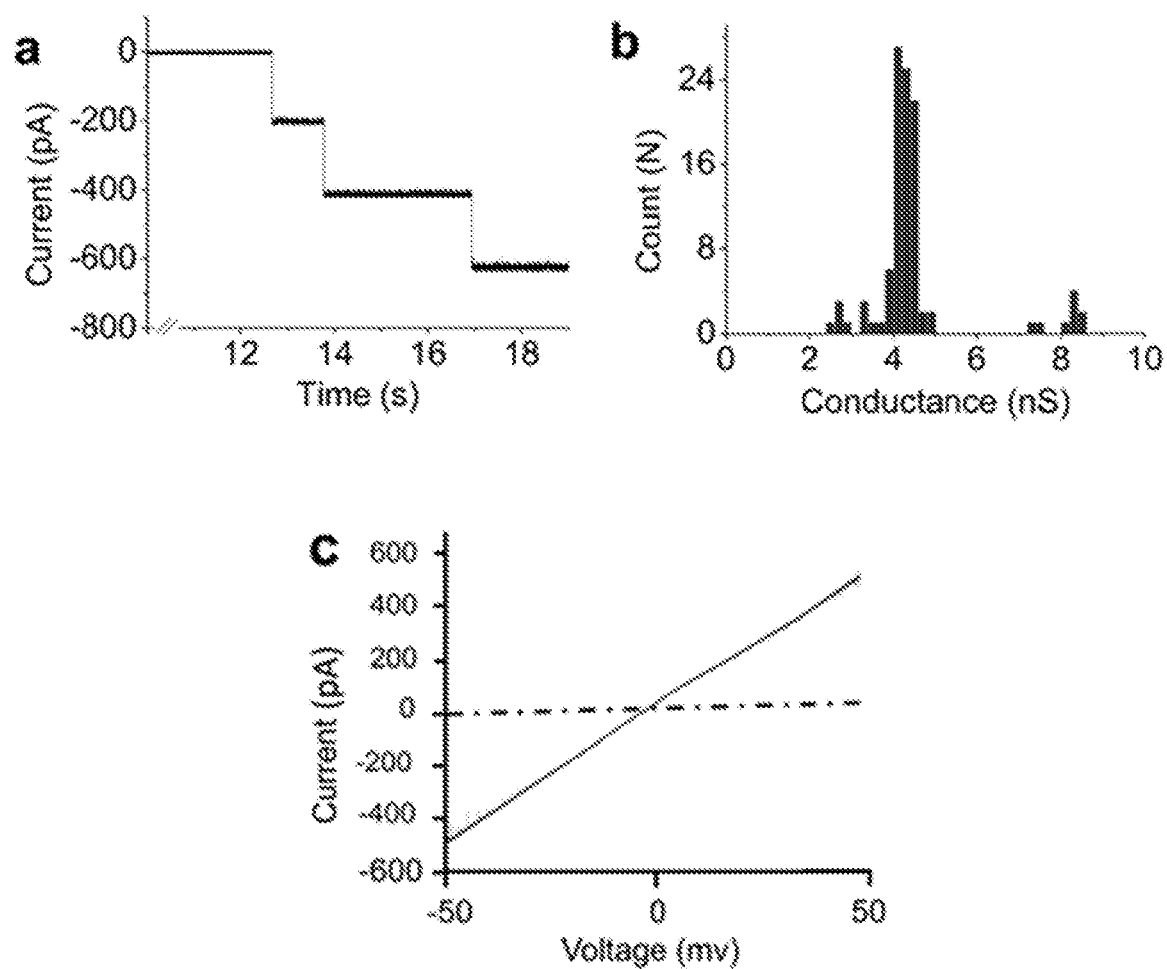
FIG. 2: Electrophysiological properties of Membrane-embedded SPP1 connector. (a) Current trace showing the insertion of SPP1 connector into the planar membrane with a characteristic step size of ~200 pA at 50 mV. (b) Conductance distribution based on 104 insertion events. (c) Current-Voltage trace acquired from −50→50 mV. Buffer: 1 M KCl, 5 mM HEPES, pH 8.

To incorporate SPP1 portal channel into planar lipid membranes, a two-step procedure was employed[28]. The connector was first reconstituted into liposomes and then the liposome-connector complex was fused with a planar lipid membrane. Direct incubation of the connector or liposome alone with a planar lipid bilayer did not result in connector insertion into the lipid bilayer. Single channel conductance assay was performed to measure the electrophysiological properties of membrane-embedded SPP1 connectors. The connector insertion steps were observed as distinct stepwise increase in conductance as revealed in a continuous current trace (FIG. 2a). The insertion of single portal channel results in ~200 pA in current jump under an applied potential of 50 mV in conducting buffer (1 M KCl, 5 mM HEPES, pH 8). Occasionally ~400 pA current jumps were observed, attributed to simultaneous insertion of two connectors. The average conductance of reengineered SPP1 connectors is 4.27±0.27 nS (FIG. 2b). The conductance is uniform without displaying any voltage gating phenomena under the reported conditions of ±50 mV (FIG. 2c).

Characterization of Peptide Translocation Through Reengineered SPP1 Connector

Figure 3:
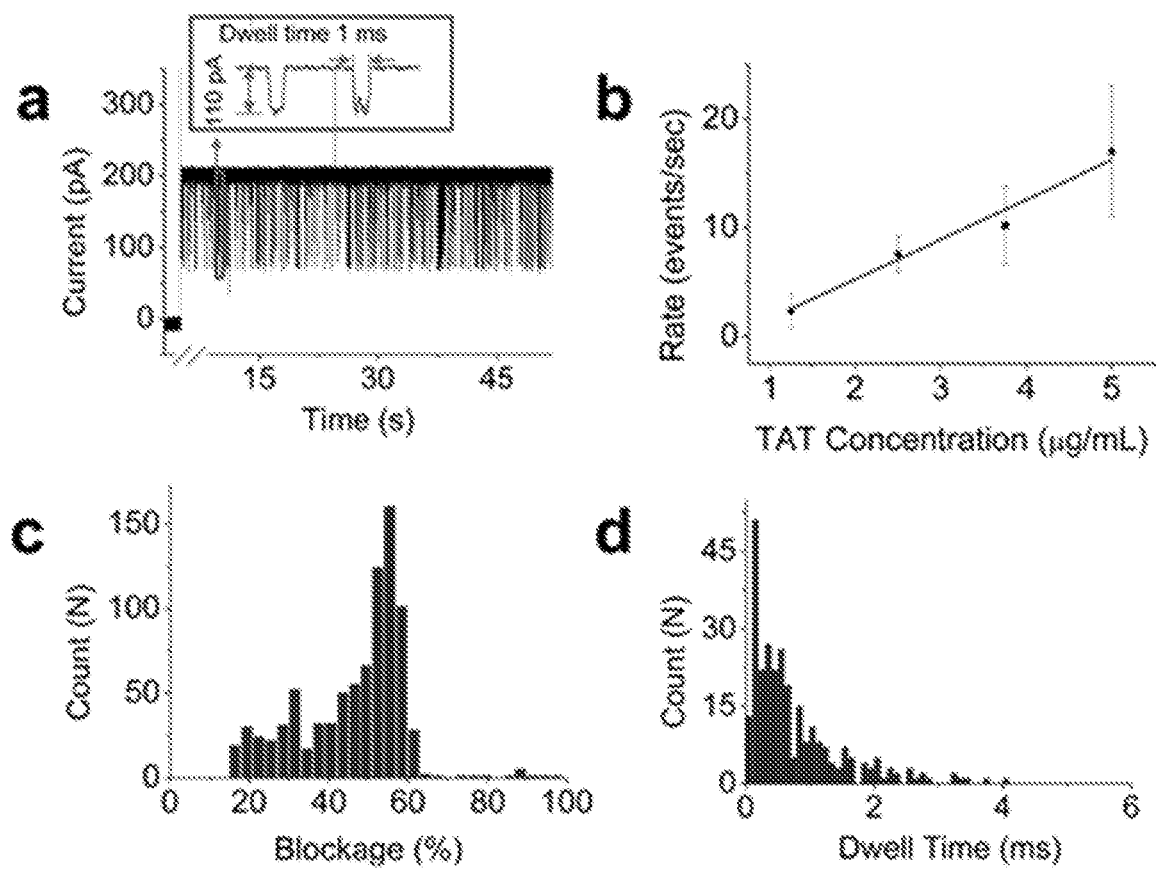
FIG. 3: Peptide translocation through SPP1 connector. (a) Current trace showing a burst of current blockage events with characteristic current amplitude and dwell time (insert) indicating the translocation of TAT peptides. (b) Rate of peptide translocation as a function of peptide concentration (n=3). (c) Histogram of current blockage percentage from 285 events. (d) Dwell time of peptide translocation events fitted with a single exponential function. Applied voltage: 50 mV; Buffer: 1 M KCl, 5 mM HEPES, pH 8.

A positively charged 12 amino acid TAT peptide was used in the translocation studies with sequence Cys-Tyr-Gly-Arg-Lys-Lys-Arg-Arg-Gln-Arg-Arg-Arg. Due to the presence of cysteine at the N-terminus, the peptide forms a dimer by disulfide bond under physiological conditions, which is confirmed by mass spectroscopy. In the absence of peptide, the current trace was quiescent. In contrast, when the peptide was premixed with the conducting buffer in both cis- and trans-chambers, a burst of transient blockage events were observed immediately after the insertion of connector in the lipid membrane (FIG. 3a). As the peptide concentration was increased from 1.25, 2.5, 3.75, to 5 µg/mL, the density of current blockage events increased with a corresponding linear increase in peptide translocation rate from 2.33±1.54, 7.5±1.66, 10.17±3.58, to 16.96±6.01 events per second (FIG. 3b). One parameter used to characterize the translocation was the current blockage percentage, calculated as the ratio of current blockade resulting from peptide translocation to the open current of one portal channel, expressed as $[(1-\text{Current}_{peptide})/\text{Current}_{open\_channel}]$. The distribution of current blockage was relatively broad with a major peak at ~55.1±3% (FIG. 3c). Another parameter was the dwell time (τ), the time taken for the peptide to traverse from one end of the connector to the other end. The dwell time distribution followed an exponential decay with a rate constant of 0.84±0.09 s$^{-1}$ (FIG. 3d).

Figure 5:
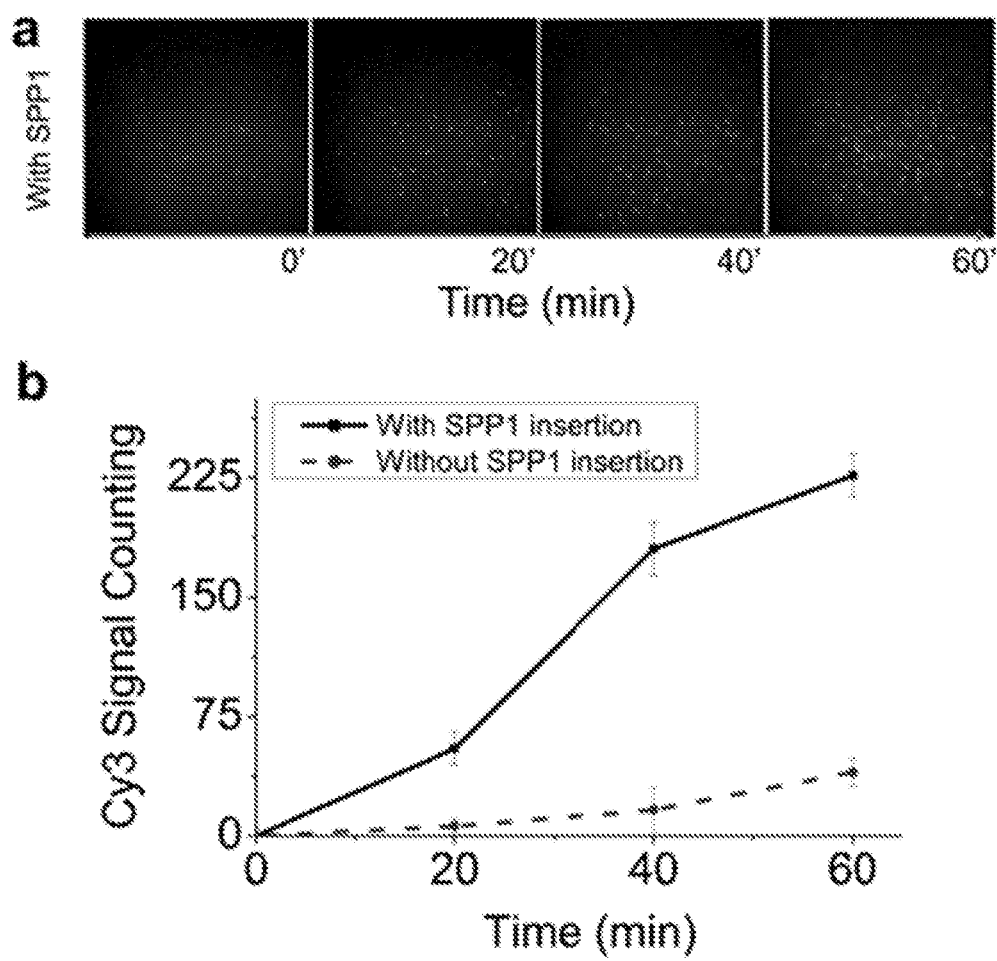
FIG. 5: Single molecule fluorescent images validating TAT peptide translocation. (a) The upper row is the image showing the detection of Cy3-labeled TAT peptide from the fractions collected from patch clamp at 0, 20, 40 and 60 mins. The lower row shows the background resulting from the self-permeation of the TAT peptide which is the HIV membrane penetrating peptide. Excitation □: 532 nm; laser power: 5 mW; 60× objective (N.A.=1.4, oil immersion); Exposure time: 500 ms. (b) Quantitative analysis showing the increase in Cy3-TAT peptide signal in presence of SPP1 connector compared to control without connector. The error bar is based on counting of the spots from different image areas. Applied voltage: 50 mV; Buffer: 1 M KCl, 5 mM HEPES, pH 8.

Quantitative Validation of Peptide Translocation by Single Molecule Fluorescence Imaging To validate the translocation of peptide through SPP1 connector, we conducted single molecule fluorescence imaging of samples collected from patch clamp experiments. HPLC purified Cy3 conjugated TAT peptide at a final concentration of 2.5 ng/µL was added to the cis-chamber after stable insertion of SPP1 connectors in the lipid bilayer. Under an applied negative trans-membrane voltage, the positively charged peptide translocated through the portal channel to the trans-chamber. 50 µL samples were collected from the trans-chamber at 0, 20, 40, and 60 minutes after addition of Cy3-TAT peptide and loaded onto glass coverslips. The positively charged peptide bound to the negatively charged glass surface through charge-charge interactions and appeared as individual fluorescent spots (FIG. 5a). Fluorescence imaging revealed that the number of Cy3 spots in the field of view increased over the time course of 60 mins (FIG. 5b). In contrast, in a control experiment under the same conditions but in the absence of portal channel, very few Cy3 spots were observed, compared to the sample containing SPP1 connector (FIG. 5b). Since TAT is a membrane penetrating peptide, it is conceivable that a small fraction could potentially pass through the lipid bilayer, contributing to the small increase in the fluorescence background signal.

Kinetic Analysis of TAT Conformational Status in Real Time

Figure 4:
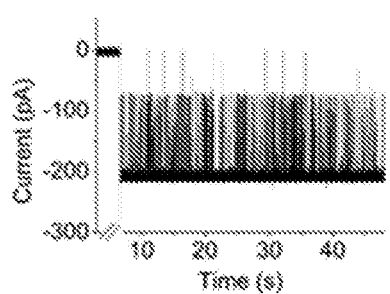
FIG. 4: Determining the conformation states of TAT peptide. Current trace (left), current blockage distribution (middle) and conformation (right) for (a) Oxidized dimer state of TAT peptide; (b) reduced monomer state of TAT peptide; and (c) Cy3-conjugated TAT monomer. Applied voltage: 50 mV; Buffer: 1 M KCl, 5 mM HEPES, pH 8. Total number of events: 858 in A; 367 in B and 1128 in C.
Figure 4:
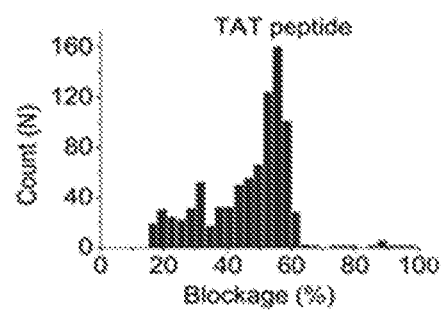
Figure 4:
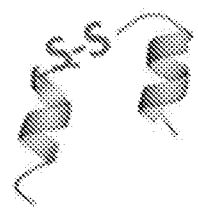
Figure 4:
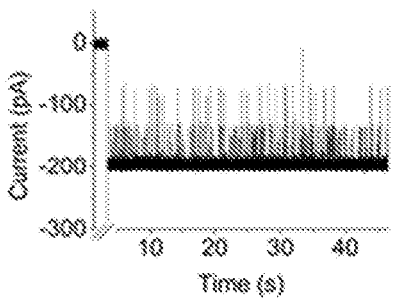
Figure 4:
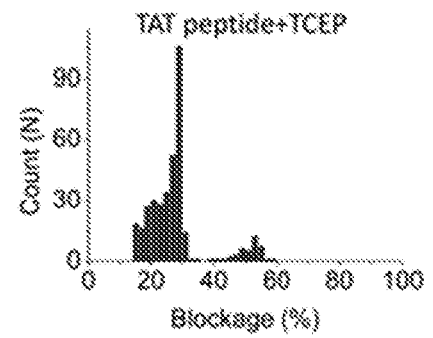
Figure 4:
Figure 4:
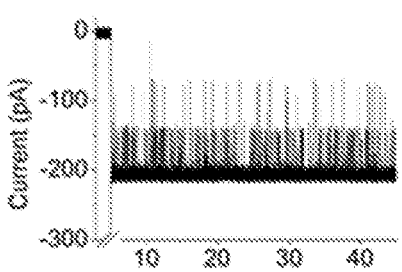
Figure 4:
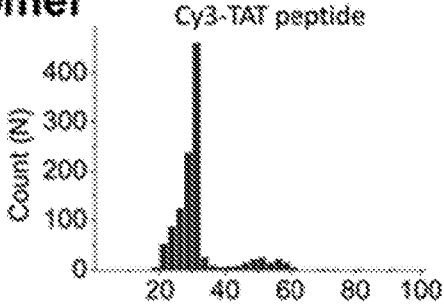
Figure 4:

The focus of this study was to investigate whether the large and robust SPP1 motor nanopore can be used for kinetic analysis of protein folding in real time. TAT peptide with and without a cysteine was used as a model system to study conformational changes. Structural analysis of TAT sequence using the computer program PEP-FOLD[49] revealed that without forming disulfide bond, the TAT only adopts one α-helical conformation (FIG. 4). However, in the presence of a cysteine at the N-terminus, the peptide can be oxidized into a dimer by forming a disulfide bond between two N-terminal cysteines and exhibiting two parallel α-helices. The presence of two states, the oxidized and the reduced conformations, were confirmed by translocation studies with the SPP1 portal channel. Under an oxidized state, the current blockage distribution by TAT displayed a major peak, centered at 55.1±3% (FIG. 4a), with a minor peak centered at 28.5±1.9%. However, after adding the reducing agent TCEP [(tris(2-carboxyethyl)phosphine)] to break the disulfide bond, the blockage distribution significantly changed. The peak of 55.1±3% decreased significantly with time, while the majority of the blockade distribution shifted to 28.5±1.9%. This indicated that most of the peptide passing through the channel is in its single α-helical conformation (FIG. 4b). Current blockage distribution of the reduced TAT peptide was similar to Cy3-TAT signature with TCEP treatment, since the conjugation of Cy3 prevented the disulfide bond formation and resulted in similar blockage, representing the single TAT helix (FIG. 4c).

Figure 6:
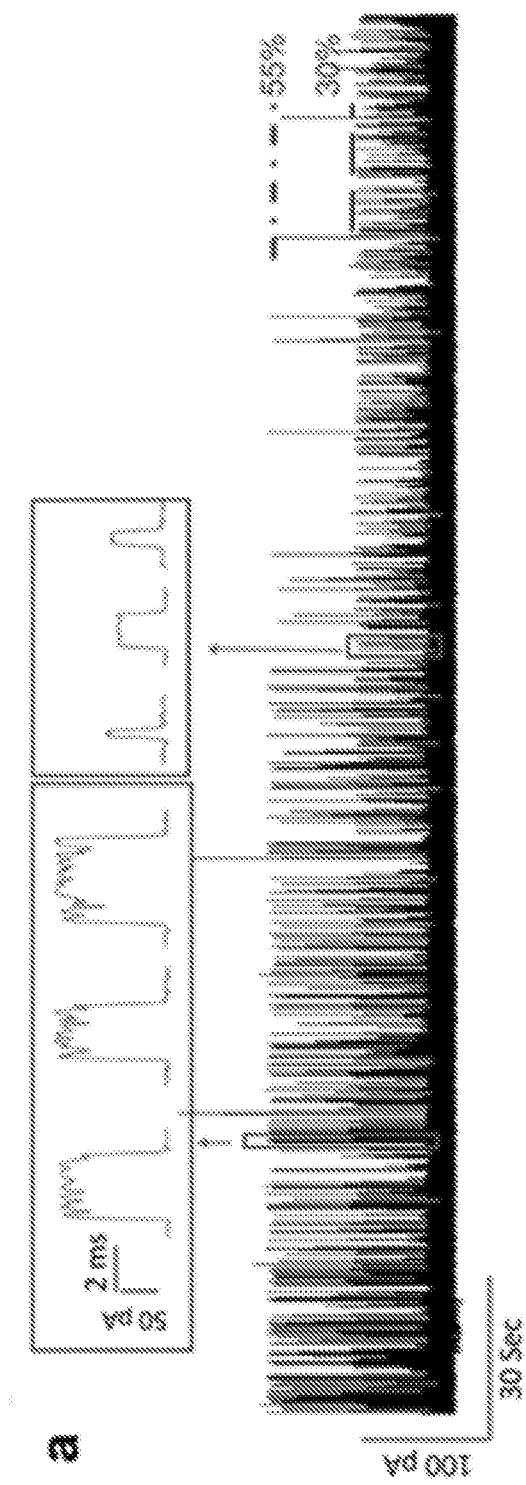
FIG. 6: Real-time assessment of the conformation states of TAT peptide. (a) Continuous current trace showing transition of oxidized dimer states to reduced monomer states after addition of reducing agent TCEP. (b) Quantitative analysis showing the fraction (□) of dimer and monomer states as a function of reaction time. (c) Current blockage versus dwell time distribution over the course of reaction time. Applied voltage: 50 mV; Buffer: 1 M KCl, 5 mM HEPES, pH 8. (d) Quantitative analysis showing the reaction quotient $Q_r$ as a function of reaction time.

To quantify the kinetics parameter, we further examined the conformational changes of TAT peptide upon addition of TCEP and recorded the change of the current blockage profile in real time (FIG. 6). The current blockade signature progressively shifted from predominantly 55.1±3% to 28.5±1.9%, representing the real-time kinetic process of disulfide bond reduction (FIG. 6a). To derive the kinetic parameter of this reaction process, two parameter γ (defined as the ratio of the number of peak A versus the sum of A and B) and reaction quotient $Q_r$ were determined (FIGS. 6b, d). The transition of γ and $Q_r$ as shown in FIGS. 6b and 5d represents the timely evolution of the reduction reaction. The γ and $Q_r$ is theoretically derived by applying second-order reaction dynamics and diffusion model, as follows:

$$TAT-TAT + TCEP \xrightarrow{H_2O} 2TAT + O - TCEP \quad (1)$$

| | | | |
|---|---|---|---|
| $C_0$ | $C(t)$ | 0 | 0 |
| $C_t$ | $C(t)-(C_0-C_t)$ | $2(C_0-C_t)$ | $C_0-C_t$ |

$$\frac{dC_t}{dt} = -kC_t[C(t)-(C_0-C_t)],$$

since $C(t) \gg C_0$, then, $C_t = C_0 * \exp(-kC(t)t)$

C(t) is the TCEP concentration at the pore entrance. According to diffusion equation, C(t) has the following form:

$$C(t) = \frac{N}{(4\pi Dt)^{1.5}} \exp\left(-\frac{r^2}{4Dt}\right).$$

In order to study the TAT reduction process quantitatively, we calculated the ratio

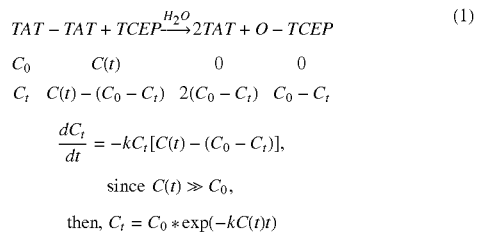

and the reaction quotient $$Qr\left(Qr \equiv \frac{[TAT]^2 * [O-TCEP]}{[TAT-TAT] * [TCEP]}\right),$$

unit is normalized). Because there is a ε

$$\left(\varepsilon \equiv \frac{[TAT]}{[TAT-TAT]}\right),$$

prior to adding TCEP) portion of TAT monomer at the beginning, the equation was solved to obtain the following equation:

$$\gamma = \frac{1}{2\exp\left(\frac{Nk}{(4\pi D)^{1.5}t^{0.5}}\exp\left(-\frac{r^2}{4Dt}\right)\right)-1+\varepsilon} \quad (2)$$

$$Q_r = \frac{2(1-\gamma)^3 C_0^2}{\gamma C_T (1+\gamma)^2}. \quad (3)$$

C(t) is the equilibrium TCEP concentration. To evaluate whether the parameters derive from this real time quantification analysis represent the real parameters of the reaction, the $\Delta G^\ominus$ value were determined from different assays using constant TAT but varied concentration of TCEP from 100, 250, 500 μM, and compared with the $\Delta G^\ominus$ derived by conventional methods.

The red line in FIG. 6b is the fitting curve with equation (2) and Qr in FIG. 6d is derived from γ with equation (3). When the reaction approaches equilibrium, Qr is equal to standard equilibrium constant $K^\ominus$. From FIG. 6d, $K^\ominus$ is estimated to be 1.4×104 and corresponding to −23.3 kJ/mol Gibbs free energy ($\Delta G^\ominus$).

As shown in FIG. 6b, γ decreased over the course of reaction time, indicating the decrease in oxidized dimer conformation and concurrent increase in reduced monomeric state. Fitting the data to a single exponential function revealed a rate constant, k=0.989±0.096 min-1 and $t_0$=5.2±0.04 min. The trend is also demonstrated in current blockage percentage versus dwell time distribution of events over the course of the reaction time (FIG. 6c). All the data from different concentrations of TCEP, show the same trends to approach equilibrium status. The related $K^\ominus$ and $\Delta G^\ominus$ are depicted in table 1.

The assay revealed that, when different concentration of TCEP were used, the $\Delta G^\ominus$ were very similar (Table 1). When the concentration of TCEP was increased from 100, 250, to 500 μM μM, the $\Delta G^\ominus$ were −24.5, −23.1, and −23.3 kJ/mol respectively. The similarity of the $\Delta G^\ominus$ derived from different assays with variable TCEP concentration suggests that using SPP1 nanopore for real time quantification of peptide folding is feasible. In addition, $\Delta G^\ominus$ derived from these experiments is very close to the $\Delta G^\ominus$ of −27 kJ/mol for disulfide bond in protein obtained by conventional methods[50].

TABLE 1

Parameters for the quantification of dynamic folding of TAT peptide in real time

| TAT concentration (nM) | TCEP concentration (μM) | $Q_r$ ($10^3$) | $K^\ominus$ ($10^3$) | $\Delta G^\ominus$ (kJ/mol) |
|---|---|---|---|---|
| 300 | 100 | 26.6 | 26.6 | −24.5 |
| 300 | 250 | 11.8 | 11.8 | −23.1 |
| 300 | 500 | 13.9 | 13.9 | −23.3 |

Discussion

In this study, we showed that the SPP1 portal channel can be successfully incorporated into planar lipid bilayer to serve as a nanopore with robust electrophysiological properties. With a conductance of 4.27 nS, it is one of the larger channels and only the second viral protein channel (apart from phi29 connector)[28] to be incorporated into a lipid membrane. In the presence of TAT peptide, a burst of current blockage events with characteristic current amplitude and dwell time were observed indicating the translocation of the peptides through the SPP1 connector. This was further validated by single-molecule fluorescence imaging. The oxidized and reduced conformations of TAT peptide can be clearly distinguished in real time. The results demonstrate the potentials of nanopore-based proteomics.

Direct evidence of DNA translocation through a-hemolysin was demonstrated twenty years ago by quantitative PCR[51]. Although a handful of studies utilizing peptide and protein translocation through nanopore, have been published over the last several years including protein folding, unfolding, stability and disease detection[41, 44, 45, 52-61]. Here, we developed a very simple method to provide evidence of peptide translocation using single molecule fluorescence imaging of samples obtained from the nanopore setup. This method can be easily adapted and employed by other laboratories to prove protein translocation and quantitatively study peptide translocation through nanopores.

In this study, we further demonstrated that this new protein nanopore is capable of detecting kinetics of TCEP mediated reduction of disulfide bond and demonstrating peptide conformational changes in real time. From FIG. 6, the frequency of dimer forms (~55%) decreased gradually to monomer forms (30%), upon addition of TCEP, as the reaction time increased. Analyzing peptides and proteins is a complex task, since they fold into versatile and complex three dimensional structures composed of 20 building blocks compared to DNA or RNA with only 4 building blocks. Further improvements are necessary to develop the nanopore into a robust platform for proteomic profiling. The current blockage signature based on the translocation profile can be used to investigate the length, charge, hydrophobicity, secondary structures and ultimately the amino acid sequences of the peptides. The kinetics of protein folding and unfolding as well as entropic and energetic contributions can be further dissected at the single molecule level.

Conclusion

A robust portal channel of bacteriophage SPP1 has been reengineered and inserted into lipid bilayer to allow the translocation of peptides with higher ordered structure to produce clear and reproducible electron signatures. Optical single molecule fluorescence microscopy were combined with resistive pulse technologies to detect the translocation of peptides quantitatively and to analyzed their conformation and dynamic folding in real-time at single molecule level. The oxidative and the reduced conformation were clearly differentiated and their timely transition in the presence of reducing agent were directly observed. When different concentrations of substrates were applied, a similar $\Delta G^\ominus$ was obtained, suggesting that the use of SPP1 nanopore for real-time dynamic quantification of peptide folding is feasible.

Materials and Methods

Materials: The phospholipid 1,2-diphytanoyl-sn-glycerol-3-phosphocholine (DPhPC) was obtained from Avanti Polar Lipids, Inc. Organic solvents (n-decane and chloroform) were purchased from Fisher Scientific, Inc. and TEDIA, Inc., respectively. TAT peptide was custom-ordered from GenScript, Inc. All other reagents were purchased from Sigma or Fisher, if not specified.

Cloning and Purification of the SPP1 connector: Gene gp6 encoding SPP1 portal was synthesized and cloned into PET3 vector between NhdeI and BamHI by GenScript, Inc. His-tag was inserted into the C-terminal of the connector for purification. Then the plasmid was transformed into BL21 (DE3) for expression and purification. The purification procedure has been described previously[28,30]. Briefly, the transformed bacteria were cultured in 10 mL LB medium overnight at 37° C. The bacteria were transferred to 1 L of fresh LB medium. When the $OD_{600}$ reached ~0.5-0.6, 5 mM IPTG was added to the medium to induce protein expression. The bacteria were collected by centrifugation after 3 hours continuous culture. Bacteria was lysed by passing through French press. Lysed cell was separated by centrifugation and supernatant containing expressed protein was collected. The supernatant was purified with Nickel affinity chromatography (Novagen)[62]. His Binding Buffer (15% glycerol, 0.5 M NaCl, 5 mM Imidazole, 10 mM ATP, 50 mM Tris-HCl, pH 8.0), and the cleared lysate was loaded onto a His•Bind® Resin Column and washed with His Washing Buffer (15% glycerol, 0.5 M NaCl, 50 mM Imidazole, 50 mM Tris-HCl, pH 8.0). The His-tagged connector was eluted by His Elution Buffer (15% glycerol, 0.5 M NaCl, 0.5 M Imidazole, 50 mM Tris-HCl, pH 8.0). The purified connector from chromatography was further purified by a 15-35% glycerol gradient ultracentrifugation at 35K for 2 hrs. Before incorporating into liposomes, the purified connector was dialyzed against buffer (0.5 M NaCl, 50 mM Tris-HCl, pH 8.0) to remove excess glycerol.

Insertion of the connector into planar lipid bilayer: The protocol for the incorporation of connectors into lipid bilayer has been reported[28-31, 63]. Briefly, planar bilayer lipid membranes (BLMs) were generated in a BCH-1A horizontal BLM cell (Eastern Scientific). A Teflon partition with a 200 μm aperture was placed in the apparatus to separate the BLM cell into cis-(top) and trans-(bottom) compartments. A planar lipid bilayer was formed by painting the aperture with 0.5 μL, of 3% (w/v) DPhPC in n-decane. A conducting buffer (1 M KCl, 5 mM HEPES, pH 7.8) was added to both the top and bottom compartments of the BLM cell, and Ag/AgCl electrodes were placed in the buffer of each compartment. The electrode in the trans-compartment was connected to the headstage of an Axopatch 200B amplifier (Axon Instruments, Inc.), and the electrode in the top compartment was grounded. Connector insertion was observed after addition of 1 μL of the diluted Liposome/connector complex to the cis-compartment directly.

Electrophysiological measurements: The headstage and Axopatch 200B patch clamp amplifier were connected to a DigiData 1440 analog-digital converter (Axon Instruments, Inc.) to monitor and record electrochemical currents through BLMs[28-30]. The current recordings were low-pass filtered at a frequency of 1 or 5 kHz. The sampling frequency was 20-200 kHz in all experiments, unless otherwise specified.

The data were recorded a with pClamp 9.1 software (Axon Instruments, Inc.), and analyzed with the Clampfit module of pClamp 9.1 and OriginPro 8.1 (OriginLab Corporation).

Peptide Translocation Experiments: TAT peptide (Cys-Tyr-Gly-Arg-Lys-Lys-Arg-Arg-Gln-Arg-Arg-Arg (SEQ ID NO: 13)) with a final concentration of 23 µg/mL was premixed with the conducting buffer before the insertion of connector. For quantitative validation, Cy3 fluorophore was conjugated to TAT peptide by sulfhydryl-maleimide chemistry and purified by HPLC. Multiple channels were inserted into bilayer lipid membrane and then Cy3-TAT peptide was added into cis-chamber. Samples were collected from the trans-chamber after 0, 20, 40, and 60 min.

Single molecule fluorescence imaging: Samples collected from the patch clamp were incubated with the ozone pretreated glass substrate for 10 min before imaging to ensure sufficient adsorption. A 532 nm green laser was used for the excitation of Cy3. A 60× objective (N.A.=1.4, oil immersion) was used for fluorescence imaging. The signals were recorded using Andor iXon 887 V electron multiplied CCD camera. Images were taken with an exposure time of 500 ms. The number of spots in the images were counted using iSMS software[64].

Example 2

Translocation of Double Strand DNA Through C-his SPP1 Phage Nanomotor Embedded in Lipid Bilayer During the process of assembly of tailed bacteriophages, their genome is packaged within a preformed procapsid through a tunnel formed by the portal protein assembly. Such entropically unfavorable process is accomplished by an ATP-driven molecular motor.[65-68]

For spp1 bacteriophage, the molecular motor consists of three proteins: gp1, gp2 (ATPase) and gp6 (portal protein). Such cyclical homooligomers are located at a single vertex of the icosahedral viral capsid that binds to the tail. During the process of assembly, portal protein translocate double-stranded DNA. After termination of packaging, portal protein is binded by head completion proteins (gp15 and gp16), which form a head-to-tail connector stereoscopic structure (Andrey A Lebedev, The EMBO Journal 2007). In common with the other herpesvirus portal protein[69], the portal protein of bacteriophage SPP1 can exist as a circular assembly. The novelty and ingenious design of viral DNA packaging motors and their mechanism of action have provoked a broad range of interest among scientists in nanotechnology, biophysics. The genome of linear double-stranded DNA (dsDNA) virus is packaged into a preformed delicate procapsid.

There exists debate about the molecular motor work mechanism of how each different component coordinate with each other. Hendrix proposed that DNA translocation is accompanied by rotation of portal protein based on the fact the low-energy barriers to rotation of symmetry mismatching protein rings relative to each other. Another models which involve the rotation of the portal protein DNA translocation is accompanied by sequential conformational changes propagating along the belt of tunnel loops with the porta protein[70-71]. Also, the structure of the most constricted part of the internal loops which is expected to be in close contact with the DNA during translocation has been characterized and defined. The portal protein has varying number of subunits: it exerts as a 13-subunit assembly in its isolated form but as a 12-subunit assembly active form when integrated into the functional viral capsid[72]. Based on the above mentioned models, a possible scenario of events during DNA translocation was discussed[73]. There is a close interaction between the portal protein and DNA and such interactions are independent of whether the viral ATPase itself performs the power stroke pushing the DNA into the capsid or whether portal protein apply the force to the DNA in response to conformational changes. Also, a 4-steps model for DNA gating (a state from open state to closed state) was proposed[74]. During this model, the nascent prohead portal binds to the packaging proteins and then a conformational change causes termination of packaging and conformational switch. After the neck and tail assembly, DNA is delivered into the host.

The information encoded in DNA is the footing stone for the development of modern medicine and life sciences. The development of individualized medicine and related scientific research has prompted the development of new kind of sequencing techniques beyond the original Sanger sequencing. As one of potential technologies, nanopore sequencing is one the rapidly sequence approaches which is expected to sequence a human genome for under $1000. So far, biological nanopores have been used to study the transport of DNA and other molecules like DNA, RNA, chemical agents, peptides, proteins and polymers[75-79]. But due to the limitation of pore dimension, most pores only allow small molecules and single-strand DNA or RNA, such as hemolysin and MSPA. α-haemolysin (α-HL) pore has been used to study the transportation of single DNA or RNA by using the transient blockade of ionic current. Bacteriophage phi 29 motor, having a larger pore size of 3.6 nm, have highly widen nanopore biomedical applications for potential DNA sequencing. There are a variety of engineered phi 29 channel have been developed to detect dsDNA, ssDNA, chemical agents and even carcinogenic antigens[80-83]. For bacteriophage spp1 molecular motor, it has similar pore size of 3.5 nm which make it very suitable for dsDNA sequencing because dsDNA normally just have a diameter of about 2 nm. However, the electrophysiological measurements of spp1 connector channels for translocation of double strand DNA have not been reported so far. In this study, the wild type spp1 connector was cloned and purified. After that, the connector was inserted into liposomes and lipid bilayer. dsDNA translocation was confirmed by single channel conductance measurements and Q-PCR assay. Our study expands the future application of spp1 nanopore in nanomedicine and nanobiotechnology.

Results

Cloning and Purification of C-his spp1 Connector

To facilitate connector purification, a C-terminus was inserted with a poly histidine tag for improved affinity tag flexibility. The linker was included to provide end flexibility. After purified by his-tag affinity column, it was found that the C-his spp1 connector self-assembled a unique 13-fold symmetric structure, which is compared with 12-fold in vivo active form, as observed by transmission electron microscopy. The existence of the motor configuration was demonstrated through its ability to package the dsDNA into the procapsid and to assemble the resulting DNA-filled capsid into the infectious phi29 virion.

Reconstituting the Connector into Liposomes

A protocol for reconstituting the connector into liposomes was developed by co-incubation of the connector with the DOPC or DPhPC lipid and hydration-rehydration of the lipid film with proteolipsome containing the reengineered connector in the presence of sucrose. Such rehydration and co-incubation make the hydropobic layer of the connector easier to interact with the hydrophobic domain of the lipid molecules. By such hydration-dehydration process, small unilamellar vesicles containing spp1 connectors (50 μm) was developed. Fluorescence microscopy and sedimentation analysis was used to confirm the insertion of the connector protein into the lipid membrane. The presence of the connector in the membrane was showed a clear florescent ring around the lipsome. While as a negative control, no fluorescent ring was observed when fluorescently tagged connector was mixed non-specifically with the non-connector inserted liposome. The free connectors were removed by 5-20% sucrose gradient ultracentrifugation.

Incorporating the Connector into Planar Lipid Membranes

The purified connector was then inserted into a planar lipid bilayer membrane (BLM). The insertion was demonstrated by the discrete stepwise increase of the current. The number of the channels inserted can be counted by counting of the number of the stepwise.

The step size of each current augment was almost identical, representing the even and uniform structure and stoichiometry. This was similar with the phi29 gp10 connector channel, which also can formed quite uniform and even channels in the BLM[75, 79]. The channel conductance of the connector was compared with that of phi29 gp10 using solutions of different ionic strength. Similarly, after a statistically analysis of conductance of two kinds of channel: wild type phi29 GP10 connector and C-his spp1 connector, two sharp Gaussian distribution was shown. Comparing to the conductance of phi29 gp10 connector, spp1 connector has a similar conductance of 4.4 ns in the presence of 1M Kcl, 5 mM HEPES, representing that both spp1 and phi29 gp10 connector has similar size. This can also be demonstrated by the crystal structure of two connector proteins[70, 79]. In addition, the channel demonstrate a perfectly linear relationship with respect to the applied voltage of 50 mV. The spp1 connector did not display voltage gating properties under the conditions described above but it showed gating at a higher voltage of 75 mV.

Translocation of Double-Strand DNA

In this report, both linear and circular plasmid were used to examine the translocation to examine the translocation of dsDNA through the connector channel. In the absence of linear DNA, the current trace was quiescent and only a quite small number of unspecific blockades were observed with a long time trace. But when dsDNA (142 bp) were added in to the cis chamber, numerous current blockades were observed, which led to the current jump of single connector insertion to be transiently reduced by 28-34%. When the voltage change to negative potential, the blockades cannot be observed. This implies that the connector exerts one-way traffic for dsDNA translocation, which is similar with one way traffic mechanism of phi29 gp10 connector. When circular plasmid dsDNA was used, no translocation of the circular plasmid was observed. Interestingly, the same amount of circular plasmid was digested by DNase and then added into the chamber, a burst of transient blockades occurred. All the above results piles up to prove that only the linear dsDNA can pass through the connector channels.

The blockade rates were affected by two factors: DNA concentration and transmembrane voltage. In the presence of 30 μM DNA under one channel insertion, the blockade rate was approximately 18 blockades per second. When the concentration of DNA placed in the chamber was doubled and tripled, the blockades frequency per second almost doubled and tripled. This implies that the blockades frequency is direct proportion to the DNA concentration.

To calculate the dwell time (τ) for DNA translocation events, only the blockade episodes greater than 30% were grouped as this percentage of blockade seemed consistent with the ratio of the cross-sectional area between dsDNA and the pore. It should also be noted that 8 (under 75 mV) individual outlying events which scattered from 100 ms to 10000 ms were excluded in the graph for clarity. The dwell time distribution under 40 mV seemed broader than that under 75 mV. The average dwell time for DNA blockades under 75 mV was 14.6 ms.

To verify the passage of dsDNA through the connector channels, quantitative polymerase chain (PCR) (Q-PCR) was used to quantify the translocation of 142-bp DNA under a voltage of 75 mV. DNA was added to the trans side and samples were taken from the cis side for quantification at 30 minutes intervals. For comparison, control experiments were performed in the absence of connectors.

The SPP1 connector protein used in this example comprises the sequence of SEQ ID NO: 4.

Example 3

Translocation of Peptides Through Membrane-Embedded C-his SPP1 Motor Protein Nanopores Living systems contain a wide range of nanomachines with diverse structures and functions. Tailed bacteriophages are a virus that infect and reproduce within a bacterium, and widely exist in the biosphere. Among the variety of bacterial viruses, viral connector protein is one of the essential components in packaging motor with turbine-like shape. SPP1 is a dsDNA phage which infects *Bacillus subtilis* and the connector of SPP1 is composed of portal protein gp6, and two head completion protein gp15 and gp16.[84, 85] The packaging motor of SPP1, which consist of gp1, gp2, and gp6, powers encapsulation of the 45.9 kb genome.[86] The ingenious design of viral DNA packaging motors and the novel mechanism of action has provoked a wide range of interest among scientists in many different areas. Although various portal proteins share little homology in primary sequence, and varies in size[87-89], they exhibit significant morphological similarity. Portal protein of SPP1 and phi29 share similar secondary structure and 3-D structure. Our recent research also found that they even share similar role in packaging genome[91-93]. Explicit engineering of the SPP1 connector is possible due to its accessible crystal structure[94, 95]. SPP1 portal protein have 13-subunit form and the pseudoatomic structure with 12-subunits. The overall diameter of 13-subunit form is ~1.65 nm, and the height is ~1.10 nm. The narrow part is 2.77 nm in 13 subunit form and 1.81 in 12 subunit form.[94, 95]

Nanopore technology has recently emerged as a new real-time single molecule sensing method, holding a great potential to reduce the cost of biosensing and DNA sequencing. Over the last decade, the α-hemolysin (α-HL) and MspA channel has been expansively investigated for sensing and DNA translocation.[96-99] Previously, we have successfully inserted phi29 connector channel from bacteriophages phi29 into lipid bilayer with robust properties.[100, 101] A one-way traffic property for dsDNA translocation with a valve mechanism for DNA packaging has also been observed.[102] The reengineered connector channel is capable to discriminate single-strand DNA or RNA from double strand. By selectively engineering a probe on the connector, single chemicals and antibody can be identified based on their distinct fingerprints.[103]. The channel also exhibits gating (a transition from an open state to a closed state) at higher trans-membrane potentials, a process that induces a conformational change in the channel subunits.[104]

The translocation of DNA and RNA have been studied extensively in other biological nanopores, such as the α-hemolysin, MsPA channel.[105] However, translocation of protein or peptide studies still have not attraction enough attention as it should be. Compared to the genome, the proteome is probably a much more accurate and direct indicator of the current health status of humans[106]. For examples, early diagnosis and monitoring the change of amyloid-β peptide is critical to the treatment of Alzheimer's and Parkinson's disease[107]. However, proteomic data practically when only trace amount of peptide or protein is present, is more difficult to acquire, because there is no amplified technique available for protein as DNA or RNA which can be readily amplified by the polymerase chain reaction[108]. In this report, we first time show that this reengineered SPP1 reengineered motor channel has been successfully incorporated into plannar lipid bilayers, when reconstituted into liposomes, allows the translocation of various charged peptides with different level blockade. The peptides can be differentiated by the blockage of the channel. This engineered SPP1 connector channel has potential for peptide or protein related diagnosis and sequencing in the future.

Results

Characterization of C-his SPP1 connector channel embedded into lipid bilayer Portal protein of SPP1 and phi29 share high homology. Similarly to phi29 connector, the central surface region of SPP1 portal protein also shows slight hydrophobicity compared with the two flanking layers at both ends, which are hydrophilic. To facilitate SPP1 connector channel purification, a C-terminus his tag was inserted just downstream of a six-glycine linker for improved affinity tag flexibility. The linker was introduced to provide end flexibility. After purification to homogeneity, the molecular weight of single subunit of SPP1 is 56 kDa as revealed in SDS PAGE gel, in agreement with theoretical molecular weight. To verify whether C-his SPP1 subunit could assemble to complex correctly, 15-35% sucrose gradient ultracentrifugation was performed. The fraction of *bovine* serum albumi (BSA) with molecular weight 60 KDa, is located at fraction 27, which represented single subunit of C-his SPP1 connector, whereas the fraction of C-his SPP1 portal protein shift to fraction 17, demonstrating high molecular weight complex has been formed.

To incorporate C-his SPP1 connector channel into planar lipid membranes, two step procedures which was also used in phi29 connector channel, was employed that the connector channel was first reconstituted into liposome first and then the liposome connector complex was fused into lipid membrane. Direct incubation of the connector channel or liposome with a planar lipid bilayer did not lead to channel insertion into the lipid bilayer. Single channel conductance assay was performed to measure the property of SPP1 connector channel. The connector channel insertion was observed through a distinct stepwise increase in conductance. The insertion of single connector channel into lipid bilayer results in an approximately 200 pA in the current jump under a potential of 50 mV in 1 M KCl 5 mM HEPES pH 8. Occasionally 400 pA current jump was observed, attributed to two connector channels insertion. Similar results were also observed under different buffer condition (data not shown). As comparison, the conductance of C-his SPP1 connector channel was also measured under a scanning voltage. Uniform distribution of conductance under and linear I-V relationship without display any voltage gating phenomenon under the reported conditions, 50 and 65 mV. The average conductance for a single channel was 2.06±0.08 nS 50 mV in 1 M NaCl 5 mM HEPES pH 8.

Translocation of Peptides Through C-his SPP1 Connector Channels and Kinetic Study Several different peptides with various isoelectric point (PI) and length have been used to examine the translocation through SPP1 connector channel, including poly histidine, poly lysine and CysTyrGlyArgLysLysArgArgGlnArgArgArg(TAT) (SEQ ID NO: 13). In absent of peptide, the current trace was quiescent. Occasionally, unspecific blockades were detected with a minimum detectable time. Compared with peptide translocation events, these unspecific blockades happened rarely. Buffer pH was adjusted according to corresponding peptide pI to have peptide possessed positive charge in order to translocate through channel under voltage. A continuous current trace recording was shown before and after addition of peptide in real timee. Before TAT was added, the current trace was quiescent with occasionally non-specific blockade events during long time recording time. Once TAT peptide was added to cis-chamber after X channel inserted into lipid bilayer, the blockage events was not immediately observed. After X minutes from the adding point, the blockade events gradually increased sparsely until reaching to a burst stage. This lagging time between the adding point and the events showing up, indicates the diffusion time from top of the solution to the nearby entrance of channel. In addition, the blockade events can only be observed under negative voltage, because the peptide was only added to cis-chamber and positive charged peptide can only translocate from cis- to trans-chamber under negative voltage. When switch the polarity to positive voltage, there is no translocation events observed. In the same experiment, however, when small amount of buffer was transferred from cis-chamber to trans-chamber, the translocation events have been observed under positive voltage. However, the translocation rate is much lower than that under negative voltage due to the concentration of TAT in trans-chamber is much lower than cis-chamber.

In comparison, when TAT peptide was premixed with buffer in both chamber before channel insertion, a burst of transient translocation events have been observed immediately after the first insertion occurred. One parameter used to characterize the translocation was the current blockage percentage, which represents the difference between the open connector channel and the reduced current caused by peptide translocation. Current blockage percentage was calculated as follows: size of current blockage resulting from peptide translcocation to one connector channel divided by step size of the current for one connector insertion.

The reduced current caused by TAT translocation is about 115 or 170 pA, and the blockade has two major distributions, 55±3% and 81±4% respectively. Translocation rate was influenced by peptide concentration. The current trance of single channel with different concentration of premixed TAT peptide under same time length. As the concentration increased from 1.25, 2.5 and 5 ug/ml, the density of blockade events has also increased correspondingly. The translocation rate versus the concentration. As concentration increases from 1.25, 2.5, 3.75, 5 ug/ml, the translocation rate also increase linearly from 2.33±1.54, 7.5±1.66, 10.17±3.58, to 16.96±6.01 events per second.

Theoretical PI of poly lysine is about 9.7, therefore here we used 1 M KCL 5 mM Hepes, pH 8. When poly lysine peptide was added to the chamber, similar results have been observed but with different level of blockade. The current trace of single channel under 1M KCl 5 mM Hepes, pH X, 65 mV and as the concentration increase from 2 ug/ml to 20 ug/ml, the translocation events increase dramatically. The reduced current is about and the blockade distribution is majored in 25%.

Similar to other peptides, the blockade events have been observed after adding poly histidines. Because poly histidine theoretical PI is only 7.6, we used 1 M KCL 5 mM Hepes, pH 6 in the experiments to ensure poly histidines possessed positive charge. Under 50 mV, translocation events have been observed immediately when poly histidines was premixed with buffer in both chamber. Compared with TAT and poly lysine, the blockade is not uniform and the major blockage distribution is majored in X. As concentration increase from X to 18 ug/ml, the translocation rate increase linearly from X.

Discussion

In this study, we first time showed that C-his SPP1 connector channel successfully has been incorporated into planar lipid bilayers when reconstituted into liposomes. Similar to phi29 connector channel, SPP1 connector channel with a central tunnel plays crucial role during the DNA packaging or ejection[109]. Although the connector proteins of different phage have no similarity in the primary sequence, available electron microscopy data has shown that they all share a common turbine-like structure (Carrascosa, 2012). SPP1 portal protein has 13-subunit in its isolated form, but as a 12 subunit from when assembled into the functional viral capsid (Orlova et al, 2003). The diameter of SPP1 connector channel as 13 subunit form in the constrict part is 2.8 nm, which is smaller than phi29 connector channel which is 3.6 nm. Similar to phi29 connector channel, structure analysis of SPP1 connector revealed that the central surface region of SPP1 connector also shows slight hydrophobicity compared with the two flanking layers at both ends.

Nanopore detection is an emerging technique that has been extensively used to study the DNA, RNA translocation given the promise of ultra-rapid nucleic acids sequencing. In contrast, study of polypeptide or protein translocation through a protein nanopore has not been pursued as aggressively. One of the biggest challenges probably is due to the complexity of protein or polypeptide which could fold into different structure and even interact with nanopore. Another problem is that neutral peptides cannot be driven through the nanopore under voltage. In addition, sequencing peptides or protein with nanopores is even more challenging since there are 20 common amino acids in nature protein compared to 4 nucleotides in DNA.

The insertions result in a uniform conductance distribution, we first time Nanopores have been extensively utilized to study DNA, RNA and analytes. However, peptide or protein recognition or sequencing using nanopore technique is still not studies extensively and has been attract enough attention. Compared to the genome, the proteome is probably a much more accurate and direct indicator of the current health status of humans. Various modifications have been studied extensively on both biological nanopores and solid-state nanopores for use in nucleic acid sensing.[110, 111] The modification of biological nanopores can b e easily achieved by the insertion, deletion, or substitution of various amino acids.112, 113 Biological nanopores can also be modified by covalently linking molecular recognition agents in the interior lumen of the pores.[103] Solid-state nanopores, conversely, have been studied mainly by chemical modifications. Different assembly pathways from modified phage portal protein monomers have been reported on SPP1[94], phi29[87], T7[114] and P2.[115] Both 12-mer and 13-mer assembly of SPP1 connectors were obtained at different conditions[94]. The mutations and modifications of these portal protein channels can be used to investigate and refine the nanopores for technical applications, such as DNA sequencing.

Translocation of single-stranded DNA or RNA by biological or solid state nanopores has drawn great attention and has been well studied by several research groups, because of its importance in DNA sequencing and many other applications in recent years.[116-119] Discrimination between single- and double-stranded nucleic acid molecules by translocating single-stranded homopolymers poly (A), poly (U), and poly (C) through solid state nanopore has been reported.[116] The translocation of long random sequence and short length ssDNA through solid state nanopores has been characterized compared with the dsDNA and the hybrid DNA/RNA.[117, 118] The relatively large diameter of the connector channel is an ideal tool for studying double-stranded DNA transport,[117] but detection of single-stranded nucleic acid remained difficult using the system reported previously.100, 101 In this paper, we generated smaller connector channels by deleting the internal loop segments of gp10 subunits and demonstrated its capability to detect ssDNA and ssRNA. The translocation events produced a uniform current blockade of 16-21%, with a peak value of ~19%. This blockade percentage is approximately half of the dsDNA blockade through the native channel, even though the cross-sectional area of the mutant channel is only 60% of the wild type.

Conclusion

The deletion of an internal flexible segment from the gp10 subunit of the phi29 DNA packaging nanomotor resulted in a smaller conductance channel with a pore diameter ~60% of the wild-type connector channel. While the single-stranded nucleic acids could not be detected by wild type channel, they showed a blockade of 16-21% while translocated through the smaller size channel. This mutant channel with smaller size is ideal for the detection and sensing of single-stranded nucleic acids, including ssDNA and ssRNA. Connector channels created from gp10 subunits with the internal loop deleted allowed for bidirectional translocation of single-stranded nucleic acids. This may also lead to the development of a hybrid system in which the smaller conductance channel can be reconstituted into a lipid bilayer, in conjunction with the wild type connector channel, for the simultaneous detection and sensing of both dsDNA and ssDNA.

Materials and Methods

Materials

The phospholipids 1,2-diphytanoyl-sn-glycerol-3-phosphocholine (DPhPC) and 1,2-dioleoyl-sn-glycerol-3-phosphocholine (DOPC) were obtained from Avanti Polar Lipids, Inc. Organic solvents (n-decane and chloroform) were purchased from Fisher Scientific, Inc. and TEDIA, Inc., respectively. The DNA and RNA oligonucleotides used in this study were obtained from Integrated DNA Technologies, Inc. All other reagents were purchased from Sigma-Aldrich, Inc., if not specified.

Cloning and Purification of the C-his SPP1 Connector Protein

Gene gp6 encoding SPP1 connector on the C-terminus was syntheses by Genescript company and then cloned into PET3 vector between NhdeI and BamHI. A His-tag was inserted into the C-terminal for purification. Then the plasmid was transformed into BL 21 (DE3) for expression and purification. The transformed bacteria were cultured in 10 ml Luria-Bertani medium overnight at 37° C. Then the cultured bacteria were transferred to 1 L of fresh LB medium. 0.5 mM IPTG was added to the medium to induce protein expression when $OD_{600}$ reached 0.5-0.6. The bacteria were collected by centrifugation after 3 hours continue culture. Bacteria was lysed by passing through French press. Lysed cell was differentiated by centrifugation and supernatant containing expressed protein was collected.=The supernatant was purified with Nickel affinity chromatography (Novagen)[120]. Cells were resuspended with His Binding Buffer (15% glycerol, 0.5 M NaCl, 5 mM Imidazole, 10 mM ATP, 50 mM Tris-Cl, pH 8.0), and the cleared lysate was loaded onto a His•Bind® Resin Column and washed with His Washing Buffer (15% glycerol, 0.5 M NaCl, 50 mM Imidazole, 10 mM ATP, 50 mM Tris-Cl, pH 8.0). The His-tagged connector was eluted by His Elution Buffer (15% glycerol, 0.5 M NaCl, 0.5M Imidazole, 50 mM ATP, 50 mM $Na_2HPO_4$-Tris-Cl, pH 8.0).

Insertion of the Connector Protein into Preformed Lipid Bilayers

Procedures have been recently developed[00-102, 104, 121] for the incorporation of connector channels into lipid bilayers. Planar bilayer lipid membranes (BLMs) were created in a BCH-1A horizontal BLM cell (Eastern Scientific, LLC). A Teflon® partition with a 0.2 mm aperture was placed in the apparatus to separate the top and bottom compartments of the BLM cell. A planar lipid bilayer of DPhPC was formed by painting the aperture with 0.5 µl of 3% (w/v) DPhPC in n-decane. A conducting buffer (1 M NaCl, 10 mM Tris-HCl, pH 7.8) was added to both the top and bottom compartments of the BLM cell, and a Ag/AgCl electrode was placed in the buffer of each compartment. The electrode in the bottom compartment was connected to the headstage of an Axopatch 200B amplifier (Axon Instruments, Inc.), and the electrode in the top compartment was grounded.

When a planar BLM was successfully formed in the aperture of the partition, separating the two compartments filled with buffer, the BLM acted as an insulator. Intact planar BLM exhibited no detectable electrical current between the two electrodes. GUVs (0.5-2.0 µl) containing connector channels were added to the top compartment. Membrane fusion between the liposomes and the BLM happened immediately after applying GUVs containing the connector protein, and it was found that a current passing through the connector channel could be recorded.

Electrophysiological Measurements The headstage and Axopatch 200B patch clamp amplifier were connected to a DigiData 1440 analog-digital converter (Axon Instruments, Inc.) to monitor and record electrochemical currents through BLMs[17, 18, 38]. The current recordings were low-pass filtered at a frequency of 1 kHz. The sampling frequency was 2 kHz in all experiments, unless otherwise specified. The data were recorded and stored on a PC with pClamp 9.1 software (Axon Instruments, Inc.), and analyzed with the Clampfit module of pClamp 9.1 and OriginPro 8.1 (OriginLab Corporation).

Electrical potentials were applied across BLMs in experiments with two different modes, holding potential mode and ramping potential mode with the pClamp 9.1 software. The ramping potential mode was used in the experiments to examine connector channel stability and DNA/RNA translocation orientation. In the holding potential mode, a constant voltage (either +75 mV or -75 mV) was applied across the BLM. In the ramping potential mode, a voltage which constantly increased over time, from either -100 mV or +100 mV to -200 mV or +200 mV, was applied across the BLM.

Purification of the DNA/RNA Used in the Experiment

A synthetic 20-nt DNA fragment was purified by mixing a 100 µM stock of the oligonucleotide with an equal volume of 2×TBE buffer (178 mM Tris base, 178 mM boric acid, 2 mM EDTA, pH 8.3). The oligonucleotide/TBE mixture was loaded onto an 8% (w/v) polyacrylamide gel containing 8 M urea-TBE. The DNA was electrophoresed through the gel at 120 V for ~1 h. After electrophoresis, the single-stranded DNA band was visualized as a shadow on a TLC plate with a hand-held UV light and then cut out of the gel. The gel containing the ssDNA was minced and the ssDNA was eluted from the gel fragments by incubating them in a small volume of elution buffer (0.5 M ammonium acetate) at 37° C. for 4 h. The gel fragments were pelleted by centrifugation and the supernatant was removed. The ssDNA was precipitated from the supernatant by adding 1/10 volume of 3 M sodium acetate and 2.5 volumes of ethanol and storing the solution overnight at -20° C. The ssDNA was again pelleted by centrifugation, and excess salt was removed by rinsing the ssDNA pellet with 70% ethanol. The purified ssDNA was dissolved and stored in TMS buffer (100 mM NaCl, 10 mM $MgCl_2$, 50 mM Tris-HCl, pH 8.0). A synthetic 20-nt ssRNA fragment was purified in a similar manner.

Translocation Experiments of DNA and RNA

Liposomes containing connector channels were added to the top compartment of the BLM cell. Soon after, highly conductive connector channel(s) were inserted into the planar BLM and a stepwise increase in current was observed. For translocation experiments, the purified ssDNA or ssRNA was mixed with conducting buffer and added to the top compartment in the BLM cell. The translocation of ssDNA or ssRNA was observed as transient blockades of the electrochemical current.

The SPP1 connector protein used in this example comprises the sequence of SEQ ID NO: 4.

Example 4

One-Way Traffic of SPP1 Viral Motor Channel for Peptide Translocation

A variety of bacterial viruses exist in diverse form in natural environment, however, many of them share lots of similarities from shape, structure, and life cycle, to packaging and infection mechanism. Recently, it was discovered a common mechanism of dsDNA translocation motors using one-way revolution mechanism, exits many bacteria and virus, including phi29, SPP1, T4, T7 and others. Among the complex system of many different phages, viral connector protein is one of the key components with turbine-like shape in phage genome packaging and ejection, shared by many bacteriophages and other viral system. Previously we have successfully inserted phi29 connector channel into lipid bilayer and found the one way traffic of DNA. Here we reported that inserted reengineered bacteriophage SPP1 connector channel also exercised a one-way traffic property for peptide translocation, as demonstrated by holding and ramping, voltage, electrode polarity switching, and quantification of peptide translocation frequency. These results indicate that most of the DNA packaging motors probably utilize the same one way traffic mechanism during DNA packing process. In addition, the observed single direction peptide transportation provide a novel system with a natural valve to control dsDNA loading and gene delivery in liposomes or peptide sequencing without using of gating control found in other biological channels.

Introduction.

A variety of bacterial viruses exist in diverse form in natural environment, however, many of them share lots of similarities from shape, structure, and life cycle, to packaging and infection mechanism. Recently, it was discovered a common mechanism of dsDNA translocation motors using one-way revolution mechanism, exits many bacteria and virus, including phi29, SPP1, T4, T7 and others[133-135]. An unusual feature of many linear dsDNA viruses is the packaging of their DNA into a preformed capsid, which is entropically unfavorable process and accomplished by an ATP-driven motor. The packaging motor of SPP1, composed gp1, gp2, and gp6, powers encapsulation of the 45.9 kb genome.[128] The ingenious and dedicate design of viral DNA packaging motors and the novel mechanism of action has provoked a wide range of interest among scientists in many different areas. Various portal proteins share little homology in primary sequence, and varies in size[129-131], although, they exhibit considerable morphological similarity[132]. Portal protein of SPP1 and phi29 both have similar secondary structure and 3-D structure. Explicit engineering of the SPP1 connector is possible because of its accessible crystal structure[135-137]. SPP1 portal protein exists in 13-subunit form and the pseudoatomic structure with 12-subunits. The overall diameter of 13-subunit form is ~1.65 nm, and the height is ~1.10 nm and the narrow part is 2.77 nm in 13 subunit form and 1.81 in 12 subunit form.[136, 137].

In vitro, the biomimetic motor can be inserted into synthetic nanodevices[138, 139]. In vivo, the artificial nanomotors can be also applied for loading drugs, delivering DNA/RNA, pumping ions, transporting cargoes, or driving the motion of components in the heart, eye or other sensing organs in the body. We have previously reengineered the connector protein and inserted the connector into lipid bilayers[1920]. The translocations of ions and peptide through the channel have been characterized to demonstrate the power of the SPP1 connector for use in single DNA sensing and fingerprinting. In this study, we report that the reengineered SPP1 motor channel exercises a one-way peptide traffic mechanism, which may related with the packaging mechanism.

Recently, chemically modified synthetic pores[141-144] and some reengineered protein channels[145-147] have been found to have ion rectifying capabilities by allowing ions to flow in one direction. For example, a mutant 7R-α-haemolysin has been discovered to only allow ion transport under positive voltages even under high ion concentrations[145]. Chemically modified synthetic pores can be made to exhibit electronic diode-like properties by a different mechanism.[148, 149].

Previously we have successfully inserted phi29 connector channel into lipid bilayer and found the one way traffic of DNA. Here we reported that inserted reengineered bacteriophage SPP1 connector channel also exercised a one-way traffic property for peptide translocation, as demonstrated by holding and ramping, voltage, electrode polarity switching, and quantification of peptide translocation frequency. These results indicate that most of the DNA packaging motors probably utilizes the same one way traffic mechanism during DNA packing process. In addition, the observed single direction peptide transportation provide a novel system with a natural valve to control dsDNA loading and gene delivery in liposomes or peptide sequencing without using of gating control found in other biological channels.

Results.

Characterization of Reengineered SPP1 Connector Channel

As revealed in crystal structure, SPP1 connector channel share similar structure with phi29 connector channel. To purify SPP1 connector channel, 6×his tag (SEQ ID NO: 11) was inserted downstream of a six-glycine linker (SEQ ID NO: 12) which was introduced to provide end flexibility. After purification to homogeneity, the molecular weight of single subunit of SPP1 is 56 kDa, which is much higher than 35 KDa of phi29 connector as revealed in SDS PAGE gel, in agreement with theoretical molecular weight. The purified reengineered SPP1 connector channel was inserted into a planar lipid bilayer membrane (BLM) via two steps. First, the connector channel was incorporated into liposome and then connector complex was fused into lipid membrane. The discrete stepwise increase of the current was observed after the connectors inserted into the membrane. Each step size was about 200 pA under 1M KCL 5 mM HEPES, pH 8 under 50 mV, and the conductance is uniform and did not display voltage gating under the applied voltage.

One-way traffic of peptide was probed by applying a constant holding voltage and by switching the voltage polarity to a membrane. There was no peptide translocation under either positive or negative voltage when no peptide is present in both chambers in a single channel study or multiple channel study. Peptide was pre-mixed in both chambers under a constant voltage. Under single channel, switching of voltage polarity showed that the connector channel allowed peptide a unidirectional translocation. Since the connector channel is incorporated into the lipid bilayer via the fusion of the liposome/connector complex, the direction of the connector cannot be controlled. The conformation of connector channel could be either C-terminus facing the cis-chamber or N-terminus facing the cis-chamber.

The correspondence to voltage switching was dependent upon the orientation of the connector in the BLM. For example, when there was no peptide translocation under positive potential, switching the voltage to negative potential resulted in peptide translocation. Similarly, translocation events appeared under positive voltage but disappeared when switch to negative voltage indicating the channel only allow one way traffic of peptide. Peptide translocation under multiple channels was shown. Under positive voltage, the first inserted channel has not shown any translocation events, however, when the second channel inserted into membrane, a burst of translocation events appeared immediately indicating the direction of two channel is opposite. Under positive voltage, the first channel has shown uniform blockade events. As expected, after switching the voltage to negative, there is no blockade events shown up, however, when the second channel inserted the blockade events suddenly appeared in a uniform manner. To further verify the one-way traffic, peptide was added to one side of chamber after multiple channel insertion. If is found that the blockade events was only appeared in one side. When the peptide added to cis-chamber, the translocation events only appeared under negative voltage since the peptide is positive charged. Similar phenomenon was also observed when peptide was added to the trans-chamber. In addition, after added different ratio of peptide in the two chambers, the blockade events rate is also different corresponding to the ratio of peptide in both chambers.

One-way traffic of peptide was probed by quantification of peptide translocation frequency in the presence of multiple channels. If connector channels allow peptide passing through only in one direction, the translocation frequency should be affected by a different conformation of connector orientation when multiple channels were inserted into the bilayer, regardless of the peptide concentration. Experiments were performed under a constant holding potential of −50 mV and in the presence of varying concentrations of peptide. The current traces of multiple connector insertions revealed the change in the frequency of peptide translocation events. When one additional connector was incorporated with an opposite orientation that did not allow peptide to pass, the frequency of DNA translocation did not change. The insertion of first channel allows the translocation of peptides from cis-chamber to trans-chamber under negative voltage. The additional insertion did not change the frequency due to the direction of second one is opposite to the first one which did not allow peptide translocation through that side. When one additional connector was incorporated with the same orientation to the previous one, the frequency of DNA translocation double depending if the direction allow peptide translocation. The second channel does not increase the translocation frequency because of the orientation is opposite to the first one, which allow peptide translocation. When the third channel inserted, the translocation frequency doubled because the direction is the same as the first connector channel.

One-way traffic of peptide was probed by applying a ramping potential to a membrane. Given that the connector channel is inserted into the BLM via the fusion of the liposome/connector complex with the BLM, the orientation of the connector channel is random. The application of a ramping potential to the BLM containing a single connector channel revealed a unidirectional translocation of peptide. A ramping voltage from −50 mV to +50 mV was applied to obtain the I-V curves.

Discussion.

Recently, Guo and Lee proposed a pushing or injection model[150]. In this model, the connector remains static; DNA translocation is induced by a DNA packaging enzyme or terminase, which pushes a certain length of DNA into the procapsid, and then shifts to bind to a far distal region of the DNA and inserts an additional section. This model does not exclude the socket wrench rotating motion by the enzyme. The studies reported here provide direct evidence to prove the model[150].

It is very interesting to observe the counter-chirality between the left-handed spp1 connector channel and the right-handed dsDNA. The spp1 connector channel is composed of 12 copies of the protein gp10 with each existing as three-helices to encircle the channel, and exhibiting a left-handed configuration. However, the regular viral dsDNA genome is the normal B-form DNA exhibiting a right-handed configuration. As far as the energy is concerned, it is expected that such an opposite configuration would favor the ejection of the dsDNA during infection and would not favor the packaging during assembly. However, our findings revealed a contrasting phenomenon: under an external electrical force, the channel favored DNA entry but blocked DNA exit, suggesting a very intriguing structure and motion mechanism for the motor. In this situation, the channel wall and the dsDNA constitute two counter-parallel helices. It is possible that the sequential attraction between the negative charge of the phosphate backbone and the positive charge of the channel wall, which contains two 12-lysine rings (aa #200, 209) separated by 2 nm (and possibly two more rings at locations K234, K235)[129], will produce a step wise propelling force for DNA translocation. It has been reported that the conformation of the spp1 connector is substantially changed after DNA packaging[151, 152]. Such significant rearrangements of the connector after DNA packaging, a similar feature reported in other phage systems as well[136, 137, 153] might change the channel configuration to reversely favor the DNA exit during infection.

Materials and Methods

Materials

The phospholipid, 1,2-diphytanoyl-sn glycerol-3-phosphocholine (DPhPC) (Avanti Polar Lipids, Alabaster, Ala.), Nickel-NTA nanogold (1.8 nm; Nanoprobes), n-Decane (Fisher), chloroform (TEDIA) were used as instructed by the vendor. All other reagents were from Sigma, if not specified. The construction and purification of reengineered spp1 C-terminal tagged connectors have been reported[140, 154].

Electrophysiological Measurements

A bilayer was formed on a thin Teflon film partition (aperture 200 μm in diameter) which separates a BLM chamber into a cis- and trans-chamber (compartment). The cis-chamber refers to the grounded compartment to which the connector reconstituted liposome was added. Connector channel insertion into the bilayer has been described previously using vesicle fusion[19]. Briefly, connector reconstituted liposomes were prepared using a dehydration-rehydration method and further extruded to form unilamellar liposomes. The reconstituted liposomes were further diluted by 10-fold using the conducting buffer before applying to BLM chambers. The final concentration of added protein was 5-50 μg/mL.

For electrophysiological measurements, both compartments in the BLM chamber were filled with a conducting buffer (1 M NaCl/5 mM Tris, pH 7.8, if not specified). A pair of Ag/AgCl electrodes connected directly to both the compartments was used to measure the current traces across the bilayer lipid membrane. The current trace was recorded using an Axopatch 200B patch clamp amplifier coupled with the Axon DigiData 1322A analog-digital converter (Axon Instruments) or the BLM workstation (Warner Instruments). All voltages reported were those of the trans-compartment. Data was low band-pass filtered at a frequency of 5 kHz or 1 KHz and acquired at a sampling frequency of 10 KHz. The PClamp 9.1 software (Axon Instruments) was used to collect the data, and the software Origin Pro 8.0 was used for data analysis.

The SPP1 connector protein used in this example comprises the sequence of SEQ ID NO: 4.

Example 5

Three-Steps of Channel Conformational Twisting Related to Paused and Quantized Packaging During Directional Genome Translocation of Bacterial Virus SPP1

The channel of the DNA-packaging motor of double-stranded DNA virus allows viral genomic to enter the protein procapsid shell during viral maturation and to exit during host infection. We recently demonstrated that DNA packaging motor of bacterial virus phi29 exercises a one-way traffic property, and uses a revolution mechanism without rotation for dsDNA packaging using a left-handed connector channel to gear the right-handed DNA. This raises a question of how dsDNA is ejected during infection using this one way valve. Previously, we reported the finding of three step gating in the channel of phi29 DNA packaging motor, and proposed a conformational changes of motor channel during DNA packaging process to prepare for the reversal of dsDNA. To determine whether the finding and proposed mechanism in phi29DNA packaging motor is universal, we cloned the gene gp-6 coding for SPP1 connector and, studied the conformational change of SPP1 connector inserted into the lipid bilayer. We found reengineered SPP1 connector also exhibited conformational changes during DNA packaging process and three step gating. We investigated and linked the gating and conformational change phenomenal to the quantized packaging studies of DNA in phi29 and T3 reported previously. It was found that the three step gating coincide with the three major steps of quantized DNA packaging intermediates. These finding lead to the conclusion that three step gating, is due to three step of motor conformational change that was revealed in three major step of quanlized packaging of DNA intermediate. This supports the speculation that the one way inbound channel were transformed into an outbound channel during the DNA packaging process and this finding will lead to the slight twisting of the dsDNA by a motor with revolution mechanism without rotation.

1. Introduction

Tailed bacterial viruses are widely distributed in nature and they shared many similarities, from structure, shape, to life cycle, packaging and infection mechanism. Among the complex system of many different phages, viral connector protein is one of the key components with turbine-like shape, shared by many bacteriophages and other viral system. It was inserted into the prohead as major part of portal complex and responsible for genome packaging and ejection. Linear dsDNA viruses package their genome into a preformed protein shell referred as procapsid[155]. This DNA encapsulation process is completed by a nanomotor using ATP as energy[156-160]. During this process, connector acts as a docking point for ATPase which powers the DNA genome translocation. SPP1 is a virulent dsDNA phage which infects *Bacillus subtilis* bacteriophages and the connector consists of portal protein gp6, and two head completion protein gp15 and gp16.[161-162] The molecular motor of SPP1, composed of gp1, gp2 and gp6, powers encapsulation of the 45.9 kbp genome.[163] The ingenious design of viral DNA packaging motors and the novel mechanism of action has irritated a wide range of interest among scientists in virology, molecular biology, structure biology, nanotechnology and other areas. Although various connectors share little homology in primary sequence and varies in size[164-166], they exhibit significant morphological similarity[167]. Portal protein of SPP1 and phi29 share similar secondary structure and 3-D structure. Our recent research also found that they even share similar role in packaging genome[168-170]. The structure of the SPP1 connector has been previously solved by X-ray crystallography,[171, 172] showing SPP1 portal protein have 13-subunit form and the pseudoatomic structure with 12-subunits. The overall diameter of 13-subunit form is ~1.65 nm, and the height is ~1.10 nm. The narrow part is 2.77 nm in 13 subunit form and 1.81 in 12 subunit form. Gating is very common in various ion channels or protein pores[173] and plays a critical role in regulating ion transportation through a membrane and DNA translocation direction. By the nature of gating, ion channels could be classified[174] as ligand-gated[175], stretch-gated[176], voltage-gated[177], or other gating[174]. Voltage-gated ion channels are sensitive to potential change near the channel, whereas the ligand-gated ion channels are activated by the binding of a chemical messenger (i.e., a ligand).

Previous studies, the connector channel from bacteriophages phi29 has been inserted into lipid bilayers to serve as a membrane-embedded nanopore with robust properties.[178, 179] A one-way traffic property for dsDNA translocation with a valve mechanism for DNA packaging has also been observed.[180] The reengineered connector channel is capable to discriminate single-strand DNA or RNA from double strand. By selectively engineering a probe on the connector, single chemicals and antibody can be identified based on their distinct fingerprints.[181]

Based on previous study, we further want to verify whether this phenomenon is universal. Here, we first time expressed reengineered SPP1 connector and found this connector also exercises 3-step gating which is similar to phi29 connector. We also further investigate the effect of voltage polarity, pH, ion concentration, and type on the gating. This finding may indicate the phenomenon of connector conformation change is common in most of the bacteriophages and share similar role in genome packaging and ejection.

2. Materials and Methods 2.1 Materials

The phospholipid, 1,2-diphytanoyl-sn glycerol-3-phosphocholine (DPhPC) (Avanti Polar Lipids, Alabaster, Ala.), n-Decane (Fisher), chloroform (TEDIA) were used as instructed by the vendor. All other reagents were from Sigma, if not specified.

2.2 Expression and Purification of Reengineered SPP1 Connector

Gene gp6 encoding SPP1 connector on the C-terminus was syntheses by Genescript company and then cloned into PET3 vector between NhdeI and BamHI. A His-tag was inserted into the C-terminal for purification. Then the plasmid was transformed into BL 21 (DE3) for expression and purification. The transformed bacteria were cultured in 10 ml Luria-Bertani medium overnight at 37° C. Then the cultured bacteria were transferred to 1 L of fresh LB medium. 0.5 mM IPTG was added to the medium to induce protein expression when $OD_{600}$ reached 0.5~0.6. The bacteria were collected by centrifugation after 3 hours continue culture. Bacteria was lysed by passing through French press. Cells were resuspended with His Binding Buffer (15% glycerol, 0.5 M NaCl, 5 mM Imidazole, 10 mM ATP, 50 mM Tris-Cl, pH 8.0), and the cleared lysate was loaded onto a His•Bind® Resin Column and washed with His Washing Buffer (15% glycerol, 0.5 M NaCl, 50 mM Imidazole, 10 mM ATP, 50 mM Tris-Cl, pH 8.0). The His-tagged connector was eluted by His Elution Buffer (15% glycerol, 0.5 M NaCl, 0.5M Imidazole, 50 mM ATP, 50 mM Tris-Cl, pH 8.0).

2.3 Electrophysiological Measurements

A bilayer was formed on a thin Teflon film partition with aperture 200 μm in diameter. This partition separates the bilayer lipid membrane (BLM) chamber into two compartments: a cis- and trans-chamber. The connector reconstituted liposome was added to the cis-chamber referred as grounded compartment. Phi29 connector channel insertion into the lipid bilayer has been reported previously using vesicle fusion[178]. Here we used the same procedure for reengineered SPP1 connector. Briefly, connector reconstituted liposomes were prepared using a dehydration-rehydration method and further extruded to form unilamellar liposomes. The reconstituted liposomes were further diluted by 10-fold using the conducting buffer before applying to BLM chambers. For electrophysiological measurements, both compartments of BLM chamber were filled with a conducting buffer. A pair of Ag/AgCl electrodes inserted to both compartments was used to measure the current traces across the bilayer lipid membrane. The current trace was recorded using an Axopatch 200B patch clamp amplifier coupled with the BLM workstation (Warner Instruments). or the Axon Digi- Data 1322A analog-digital converter (Axon Instruments) All voltages reported were those of the trans-compartment from 100 mv, 75 mV, 50 mV. Data was low band-pass filtered at a frequency of 5 kHz or 1 KHz and acquired at a sampling frequency of 10 KHz. The PClamp 9.1 software (Axon Instruments) was used to collect the data, and the software Origin Pro 8.0 was used for data analysis.

3. Results 3.1 The Lipid Membrane-Embedded C-his SPP1 Connector Display Uniform Conductance.

To facilitate connector purification, a C-terminal His tag was inserted downstream of the gp-6 gene. The reengineered connectors were purified to homogeneity and run on SDS-PAGE gel with C-His phi29 connector as controls. The molecular weights of C-His tagged SPP1 and phi29 connector channel are 56 kDa and 35 kDa, respectively. After purification, the connector channels was first incorporated into liposome and then fused into lipid bilayer. The connector channel embedded into the lipid bilayer was stable and displayed a uniform conductance. The conductance of reengineered SPP1 connector channel is 2.06 nS under 1M NaCL 5 mM HEPES pH 8.0.

3.2 C-his SPP1 Connector Exercise Discrete and Uniform Three Step Conformational Change At a low constant holding potential (±50 mV), the channel conductance is stable and there is no gating observed under both voltage in a long time recording. However, when a higher potential voltage is applied, a 3-step channel size reduction is often observed immediately thereafter, which is very similar to phi29 connector channel and other membrane gating behaviors. In the given experiment conduction (1 M KCl with 5 mM HEPES, pH 8), to induce gating, the positive voltage applied across the membrane need to be over 100 mV. Under this voltage, single channel current jump is around 380 pA, and each reduction step size was 120 pA accounting for 32% of the entire channel. Whereas to induce gating under negative potential, the threshold value just need to be over 75 mV and each reduction step size was about 90 pA still accounting for the 32% of the open channel. This 3-step channel gating can be induced by the high voltage regardless the buffer conditions. It is also interesting to note that after the 3-step reduction, there was still a residual current of 20 pA opening, which is about ~5.3% of one channel. Similar results were observed at phi29 connector channel. However, this closed channel can open immediately if an opposite potential is applied or a lower voltage applied.

3.3 Polarity Dependence Gating of C-his SPP1 Gating

When multiple channels inserted into lipid bilayer and reach a steady stage, the polarity was switched from positive potential to negative potential and it is interestingly found that the gating showed polarity dependence. A trace current of multiple channels at ±50, ±75 and ±100 mv. Under 50 mV, 1M NaCl, 5 mM Hepes pH 6, multiple channels have been continually incorporated into lipid bilayer until reaching a steady stage without any gating. When varies the voltage to +75 mV under the same buffer condition, there was still no gating observed for several minutes recording. However, when switching to −75 mV, gating occurred immediately and continuously until the channels closing completely. Each reduction size is in agreement of the data in single channel study. When applied 100 mV voltage across the membrane under the same buffer condition, gating occurred immediately when switch to −100 mV. The gating step is still one third of one channel current jump which is the same as observed under single channel study. The data clearly shows that gating of C-his SPP1 channel is polarity dependence and gating occurs much often under negative voltage than that under positive voltage.

It was also observed that the gating of the connector channel was reversible. When a transmembrane voltage of 0 pA applied for 10 to 30 seconds, the gated channel was observed to re-open. After the channel shutting down was triggered by higher voltage (−100 mV and −150 mV), a lower voltage was applied to allow the connector protein to recover. It was found that the conductance of the channels restored to their original state within 10 seconds.

3.3 pH Effect on Gating Property

In order to further characterize the factors that affect the gating property of C-his SPP1 channel, a series of pH has been tested. When pH increase to 10 and 12 under 1M NaCL 5 mM Hepes, 75 mV applied across the membrane, similar gating trend has been observed as it under pH 6 that gating occurred immediately when switching from positive voltage to negative voltage. When applied scanning voltage from −100 to 100 mV, similar phenomenon has been observed. However, the, the noise level change.

When pH decrease from 6 to below 3, incorporation channels under 75 mV is very difficult. So to increase the incorporation chance, the voltage has been decreased to ±25 mV. Under this voltage, it's interesting observing the voltage polarity dependence become opposite that the channel become very unstable under positive voltage but when switch to negative voltage, the channels became stable. This phenomenon has also been confirmed under scanning voltage.

3.4 Salt Concentration Effect on Gating Property

Salt concentration effect on the gating has also been investigated. In this study, we have investigated the gating property under 1 M, 0.5M, 0.2 M and 50 mM NaCl. As the concentration decrease to 0.5 M, the channels are stable under positive voltage but gating occurs immediately under −75 mV. However, when the concentration decreases to 0.2M, the channels are stable under both positive and negative 75 mV voltage. Similar phenomenon has also been observed under 50 mM NaCl.

4. Discussion

Viral DNA packaging has been extensively studied in many viral systems, but the actual mechanism remains elusive. Many models have been proposed to interpret the mechanism of packaging process during the last several decades, including: 1) Ratchet mechanism[182] 2) Gyrase-driven supercoiled and relaxation[159, 183, 184]; 3) Brownian motion[185]; 4) Force of osmotic pressure[186] 5) Five-fold/six-fold mismatch connector rotating thread[187]; 6) Supercoiled DNA wrapping[188]; 7) Electro-dipole within central channel[164]; 8) Sequential action of motor components[189, 190] and, 9) Connector contraction hypothesis[191]. All these models are intriguing, but none of them have been supported by conclusive experimental data; or in other cases, validated in one viral system but disproved in another. The five-fold/six-fold mismatch connector rotating thread model[187] has been popular for several decades, because this model could introduce a new mechanical motor prototype. Numerous laboratories, including our own, have persevered to search, interpret, even design a five-fold ring to fit findings to this fascinating model[190, 192-194]. Unfortunately, recent studies in many viral DNA packaging motors reveal that the stoichiometry of motor components is an even number rather than an odd number[195-198]. In 1998, Guo and his colleagues first proposed a DNA packaging mechanism which is similar to the process of the translocation of dsDNA in hexameric AAA+ ATPase during DNA replication and repair. The finding of even-number subunits agree with the mechanism of many other well-studied DNA tracking motors[199-202] and the AAA+ ATPase family. More recent publications[194, 203-205] also support our findings[197, 198, 206] that hexameric structure is built by pRNA dimer[206]. X-ray crystallography study also confirmed that pRNA forms a dimer in solution which forms a tetramer without the procapsid[194, 206], supporting the theory that the dimer is the building unit of the hexamer and the sequential action in hexamer assembly is 2→4→6. It would be desirable if the mechanism of the sequential action among the channel subunits is elucidated in the future Recently, Guo and his colleagues discovered a third type of biomotor with revolution mechanism without rotation in bacteriophages phi29. Later, they found this mechanism is very common in DNA translocation motors of viruses and bacteria, including HK97, SPP1, P22, T4, T7, cellular DNA translocase FtsK. By employing revolution mechanism the motor can translocate dsDAN free of coiling and torque which has solved many puzzles and debates occurred throughout the history of viral DNA packaging motor studies.

Revolution involves the left-handed connector channel to facilitate the entry of the dsDNA during packaging[170, 180]. It would be reasonable to believe that, after DNA packaging is completed, a conformational changes will occur in order to convert the left-handed connector into the right-handed configuration to facilitate DNA exit to infect host cells. Indeed, three steps of conformational changes of phi29 connector have been reported (Jia). In addition, previous studies have found that isolation of particles derived from DNA intermediates has shown three distinct peak, indicating that three step conformational change of connector may play an important role in the DNA packing process [Mary-Ann Bjornsti, 1983; Philip Serwer, 2014]. It is expected that a small right-handed twisting of the dsDNA will be observed since the dsDNA is aligned with the wall of the connector channel and the left- to right-handed conformational change. Biophysical studies to distinguish the very small angle right-handed twisting from the 3600/10.5 base pairs left-handed rotation would be very interesting.

In addition, many studies have shown the expansion of procapsid during DNA packaging of bacteriophages.[207-214.] Connector is a crucial 1 component in the regulation of procapsid shape and size[215]. Therefore, it is reasonable to assume that procapsid expansion is related to the connector conformational change.

Our results support the proposal that these three steps of conformational change are responsible for packaging dsDNA and this is common in many viral DNA packaging motor. We demonstrated that the binding or contact of components to the C-terminal would result in the similar discrete steps of conformational change. Conductance assay using mutant connector conjugated with a Strep-tag to its C-terminal and inculcated with anti-strep tag antibody or nanogold coated with streptavidin revealed a three discrete steps of channel change with blockade of about 32%. It is reasonable to believe that the translocation of DNA into the procapsid or the internal pressure of the fully packaged DNA within the procapsid might lead to the contact of DNA with the C-terminal flexible domain, inducing a conformation changes with two subsequent functions: 1) to prevent the dsDNA from exit; and 2) to prepare a new channel configuration to facilitate the injection of DNA during the host cell infection process. The proposed second step of action has also been evidence in the P22 system[213]. To further support this, a connector mutant with the removal of a 25 amino acid segment at each C-terminus of the 12 subunits were constructed with a strep-tag conjugated to the C-terminus. With this mutant, the discrete steps of 32% conductance change were not observed in the presence of streptavidin. However, conductance assay of the mutant connector by electrical ramping revealed that three-discrete steps of conformational changes were also observed. The finding suggests that conformational change was a result of the transition of the entire connector structure, and the C-terminal only served as a trigger. This conclusion agrees with the finding in the connector structure of bacteriophage P22 12. A unique topology of the C-terminal domain was reported to be a ~200-Å-long α-helical barrel that inserts deeply into the virion and is highly conserved in the Podoviridae family. They proposed that the barrel domain would facilitates genome spooling into the interior of the procapsid during DNA packaging, and in analogy to a rifle barrel to increases the accuracy of DNA ejection during infection. During the course of our investigation, we also found that the batch of the polyclonal antibody made a difference, suggesting that not all binding to any location of the C-terminus would induce conformational changes and certain epitope at the C-terminus was important for triggering the conformation change.

The mechanism of ion channel gating has been extensively studied[174]. The ligand-gated ion channels are regulated by a ligand and are usually very selective to one or more ions such as $Na^+$, $K^+$, $Ca^{2+}$, or $Cl^-$. Such receptors located at synapses convert the chemical signal of a presynaptically released neurotransmitter directly and very quickly into a postsynaptic electrical signal. Conformational changes of α helices in voltage-gated sodium channels and calcium channels have been proposed to explain the gating mechanism. From crystallographic structural studies of the SPP1 connector protein, it is possible to surmise that when a potential difference is introduced over the membrane, the associated electromagnetic field induces a conformational change in the protein channel. From the structural viewpoint of a single chain in the connector protein, certain areas of the chain are flexible enough to induce a conformational change in response to an environmental stimuli. The interaction of dsDNA or SPP1 terminal protein gp3 induces a conformational change that distorts the shape of the channel proteins sufficiently such that the cavity, or channel, opens to admit ion influx or efflux across the membrane, down its electrochemical gradient. This conformational change leads to the opening or closing of the channel, which will help to control the packaging or release of the viral genome.

The controllable opening and closing of the connector protein has been achieved with different polarity, which also resembles the voltage-gated ion channels. However, they have different functions in the biological environment. The ion channels may have to open and close multiple times in their life cycle, whereas the SPP1 DNA connector protein might require less. The significantly different gating behavior of the internal flexible loop-cleaved connector suggests that the flexible loops may play a key role in the voltage gating. Results described above show that after the removal of these loops, both the occurrence and extent of gating reduced tremendously. These loops can induce conformational changes to adjust the channel size in response to an applied potential. Further studies are necessary to investigate if other domains of the connector protein also contribute to its gating and conformational changes.

5. Conclusions

Three step gating and a conformational changes of motor channel in the channel of SPP1 connector has been found in this study, a phenomenal identical to the finding in phi29. We propose the gating and conformational change phenomenal may link to the quantized packaging studies of DNA in phi29 and T3 reported previously. It was found that the three step gating coincide with the three major steps of quantized DNA packaging intermediates. These finding lead to the conclusion that three step gating, is due to three step of motor conformational change resulting in three major step of quanlized packaging or DNA intermediate, and support the speculation that the one way inbound channel were transformed into an outbound channel during the DNA packaging process and this finding will lead to the slight twisting of the dsDNA by a motor with revolution mechanism without rotation.

The SPP1 connector protein used in this example comprises the sequence of SEQ ID NO: 4.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Shu, D. et al., Thermodynamically stable RNA three-way junctions for constructing multifuntional nanoparticles for delivery of therapeutics. *Nature Nanotechnology* 6, 658-667 (2011).
2. Li, H. et al., RNA as a stable polymer to build controllable and defined nanostructures for material and biomedical applications. *Nano Today* In press. (2015).
3. Pi, F. et al., Discovery of a new method for potent drug development using power function of stoichiometry of homomeric biocomplexes or biological nanomotors. *Expert Opin. Drug Deliv.* 1-14 (2015).
4. Guo, P. et al., Common Mechanisms of DNA translocation motors in Bacteria and Viruses Using One-way Revolution Mechanism without Rotation. *Biotechnology Advances* 32, 853-872 (2014).
5. Kim, J. W., Kim, J. H. & Deaton, R., DNA-Linked Nanoparticle Building Blocks for Programmable Matter. *Angewandte Chemie*-International Edition 50, 9185-9190 (2011).
6. Cuervo, A. & Carrascosa, J. L., Viral connectors for DNA encapsulation. *Curr. Opin. Biotechnol.* (2011).
7. Hu, B., Margolin, W., Molineux, I. J. & Liu, J., Structural remodeling of bacteriophage T4 and host membranes during infection initiation. *Proc. Natl. Acad. Sci. USA* 112, E4919-E4928 (2015).
8. Orlova, E. V. et al., Structure of a viral DNA gatekeeper at 10 A resolution by cryo-electron microscopy. *EMBO J.* 22, 1255-1262 (2003).
9. Lurz, R. et al., Structural organisation of the head-to-tail interface of a bacterial virus 1. *J Mol Biol* 310, 1027-1037 (2001).
10. Camacho, A. G. et al., *Bacillus subtilis* bacteriophage SPP1 DNA packaging motor requires terminase and portal proteins. *J. Biol. Chem.* 278, 23251-23259 (2003).
11. Kinouchi, N. et al., Atelocollagen-mediated local and systemic applications of myostatin-targeting siRNA increase skeletal muscle mass. *Gene Ther.*, (2008).
12. Lebedev, A. A. et al., Structural framework for DNA translocation via the viral portal protein. *EMBO J.* 26, 1984-1994 (2007).
13. Lhuillier, S. et al., Structure of bacteriophage SPP1 head-to-tail connection reveals mechanism for viral DNA gating. *Proc. Natl. Acad. Sci. U.S.A* 106, 8507-8512 (2009).
14. Haque, F. et al., Solid-state and biological nanopore for real-time sensing of single chemical and sequencing of DNA. *Nano Today* 8, 56-74 (2013).
15. Branton, D. et al., The potential and challenges of nanopore sequencing. *Nat. Biotechnol.* 26, 1146-1153 (2008).
16. Venkatesan, B. M. & Bashir, R., Nanopore sensors for nucleic acid analysis. *Nature Nanotechnology* 6, 615-624 (2011).
17. Healy, K., Nanopore-based single-molecule DNA analysis. *Nanomedicine* 2, 459-481 (2007).
18. Majd, S. et al., Applications of biological pores in nanomedicine, sensing, and nanoelectronics. *Current Opinion in Biotechnology* 21, 439-476 (2010).
19. Kasianowicz, J. J. et al., Nanoscopic porous sensors. *Annu. Rev. Anal. Chem.* (Palo. Alto. Calif.) 1, 737-766 (2008).
20. Howorka, S. & Siwy, Z., Nanopore analytics: sensing of single molecules. *Chem. Soc. Rev.* 38, 2360-2384 (2009).
21. Reiner, J. E. et al., Disease detection and management via single nanopore-based sensors. *Chem. Rev.* 112, 6431-6451 (2012).
22. Geng, J. et al., Stochastic transport through carbon nanotubes in lipid bilayers and live cell membranes. *Nature* 514, 612-615 (2014).
23. Chang, H. et al., DNA counterion current and saturation examined by a MEMS-based solid state nanopore sensor. *Biomed. Microdevices.* 8, 263-269 (2006).
24. Manrao, E. A. et al., Reading DNA at single-nucleotide resolution with a mutant MspA nanopore and phi29 DNA polymerase. *Nat Biotechnol.* 30, 349-353 (2012).
25. Stoddart, D. et al., Single-nucleotide discrimination in immobilized DNA oligonucleotides with a biological nanopore. *Proc. Natl. Acad. Sci. U.S.A.* 106, 7702-7707 (2009).
26. Pastoriza-Gallego, M. et al., Dynamics of unfolded protein transport through an aerolysin pore. *J. Am. Chem. Soc.* 133, 2923-2931 (2011).
27. Chen, M., Khalid, S., Sansom, M. S. & Bayley, H., Outer membrane protein G: Engineering a quiet pore for biosensing. *Proc. Natl. Acad. Sci. U.S.A* 105, 6272-6277 (2008).
28. Wendell, D. et al., Translocation of double-stranded DNA through membrane-adapted phi29 motor protein nanopores. *Nat. Nanotechnol.* 4, 765-772 (2009).
29. Jing, P. et al., Robust Properties of Membrane-Embedded Connector Channel of Bacterial Virus Phi29 DNA Packaging Motor. *Mol. Biosyst.* 6, 1844-1852 (2010).
30. Haque, F., Geng, J., Montemagno, C. & Guo, P., Incorporation of Viral DNA Packaging Motor Channel in Lipid Bilayers for Real-Time, Single-Molecule Sensing of Chemicals and Double-Stranded DNA. *Nat. Protoc.* 8, 373-392 (2013).
31. Jing, P. et al., One-Way Traffic of a Viral Motor Channel for Double-Stranded DNA Translocation. *Nano Lett.* 10, 3620-3627 (2010).
32. Fang, H., Jing, P., Haque, F. & Guo, P., Role of channel Lysines and "Push Through a One-way Valve" Mechanism of Viral DNA packaging Motor. *Biophysical Journal* 102, 127-135 (2012).
33. Geng, J., Wang, S., Fang, H. & Guo, P., Channel size conversion of Phi29 DNA-packaging nanomotor for discrimination of single- and double-stranded nucleic acids. *ACS Nano* 7, 3315-3323 (2013).

34. Haque, F. et al., Single pore translocation of folded, double-stranded, and tetra-stranded DNA through channel of bacteriophage Phi29 DNA packaging motor. *Biomaterials* 53, 744-752 (2015).
35. Haque, F. et al., Real-Time Sensing and Discrimination of Single Chemicals Using the Channel of Phi29 DNA Packaging Nanomotor. *ACS Nano* 6, 3251-3261 (2012).
36. Wang, S. et al., Engineered Nanopore of Phi29 DNA-Packaging Motor for Real-Time Detection of Single Colon Cancer Specific Antibody in Serum. *ACS Nano* 7, 9814-9822 (2013).
37. Wen, S. et al., Highly sensitive and selective DNA-based detection of mercury(II) with alpha-hemolysin nanopore. *J. Am. Chem. Soc.* 133, 18312-18317 (2011).
38. Uhlen, M. & Ponten, F., Antibody-based proteomics for human tissue profiling. *Mol Cell Proteomics* 4, 384-393 (2005).
39. Barnham, K. J. et al., Platinum-based inhibitors of amyloid-beta as therapeutic agents for Alzheimer's disease. *Proc. Natl. Acad. Sci. USA* 105, 6813-6818 (2008).
40. Steuerwald, D. et al., Nanoshuttles propelled by motor proteins sequentially assemble molecular cargo in a microfluidic device. *Lab Chip* 14, 3729-3738 (2014).
41. Wang, H. Y. et al., Nanopore analysis of beta-amyloid peptide aggregation transition induced by small molecules. *Anal. Chem.* 83, 1746-1752 (2011).
42. Stefureac, R. et al., Transport of alpha-helical peptides through alpha-hemolysin and aerolysin pores. *Biochemistry* 45, 9172-9179 (2006).
43. Movileanu, L., Squeezing a single polypeptide through a nanopore. *Soft Matter* 4, 925-931 (2008).
44. Wang, Y. et al., Nanopore sensing of botulinum toxin type B by discriminating an enzymatically cleaved Peptide from a synaptic protein synaptobrevin 2 derivative. *ACS Appl. Mater. Interfaces* 7, 184-192 (2015).
45. Pastoriza-Gallego, M. et al., Dynamics of unfolded protein transport through an aerolysin pore. *J Am. Chem. Soc* 133, 2923-2931 (2011).
46. Biswas, S. et al., Click Addition of a DNA Thread to the N-Termini of Peptides for Their Translocation through Solid-State Nanopores. *ACS Nano.* 9, 9652-9664 (2015).
47. Schiopu, I., Iftemi, S. & Luchian, T., Nanopore investigation of the stereoselective interactions between Cu(2+) and D,L-histidine amino acids engineered into an amyloidic fragment analogue. *Langmuir* 31, 387-396 (2015).
48. Archakov, A. I., Ivanov, Y. D., Lisitsa, A. V. & Zgoda, V. G., AFM fishing nanotechnology is the way to reverse the Avogadro number in proteomics. *Proteomics* 7, 4-9 (2007).
49. Maupetit, J., Derreumaux, P. & Tuffery, P., PEP-FOLD: an online resource for de novo peptide structure prediction. *Nucleic Acids Res* 37, W498-W503 (2009).
50. David, C., Foley, S. & Enescu, M., Protein S-S bridge reduction: a Raman and computational study of lysozyme interaction with TCEP. *Phys Chem. Chem. Phys* 11, 2532-2542 (2009).
51. Kasianowicz, J. J., Brandin, E., Branton, D. & Deamer, D. W., Characterization of individual polynucleotide molecules using a membrane channel. *Proc. Natl. Acad. Sci. USA* 93, 13770-13773 (1996).
52. Pastoriza-Gallego, M. et al., Evidence of unfolded protein translocation through a protein nanopore. *ACS Nano* 8, 11350-11360 (2014).
53. Fologea, D., Ledden, B., McNabb, D. S. & Li, J., Electrical characterization of protein molecules by a solid-state nanopore. *Appl. Phys Lett.* 91, 539011-539013 (2007).
54. Kukwikila, M. & Howorka, S., Nanopore-Based Electrical and Label-Free Sensing of Enzyme Activity in Blood Serum. *Anal. Chem.* 87, 9149-9154 (2015).
55. Harrington, L., Alexander, L. T., Knapp, S. & Bayley, H., Pim Kinase Inhibitors Evaluated with a Single-Molecule Engineered Nanopore Sensor. *Angew. Chem. Int. Ed Engl.* 54, 8154-8159 (2015).
56. Wang, Y. et al., Nanopore sensing of botulinum toxin type B by discriminating an enzymatically cleaved Peptide from a synaptic protein synaptobrevin 2 derivative. *ACS Appl. Mater. Interfaces.* 7, 184-192 (2015).
57. Qiu, W. & Skafidas, E., Detection of protein conformational changes with multilayer graphene nanopore sensors. *ACS Appl. Mater. Interfaces.* 6, 16777-16781 (2014).
58. Wang, L., Han, Y., Zhou, S. & Guan, X., Real-time label-free measurement of HIV-1 protease activity by nanopore analysis. *Biosens. Bioelectron.* 62, 158-162 (2014).
59. Asandei, A. et al., Probing of various physiologically relevant metals-amyloid-beta peptide interactions with a lipid membrane-immobilized protein nanopore [corrected]. *J. Membr. Biol.* 247, 523-530 (2014).
60. Fan, J. et al., Nanopore film based enrichment and quantification of low abundance hepcidin from human bodily fluids. *Nanomedicine.* 10, 879-888 (2014).
61. Mereuta, L. et al., Slowing down single-molecule trafficking through a protein nanopore reveals intermediates for peptide translocation. *Sci. Rep.* 4, 3885 (2014).
62. Robinson, M. A. et al., Affinity of molecular interactions in the bacteriophage phi29 DNA packaging motor. *Nucleic Acids Res.* 34, 2698-2709 (2006).
63. Geng, J. et al., Three reversible and controllable discrete steps of channel gating of a viral DNA packaging motor. *Biomaterials* 32, 8234-8242 (2011).
64. Preus, S. et al., iSMS: single-molecule FRET microscopy software. *Nature Methods* 12, 593-594 (2015).
65. Guo, P., Peterson, C. & Anderson, D. Prohead and DNA-gp3 dependent ATPase activity of the DNA packaging protein gp16 of bacteriophage f29. J. Mol. Biol. 197, 229-236 (1987).
66. Chemla, Y. R. et al. Mechanism of force generation of a viral DNA packaging motor. Cell 122, 683-692 (2005).
67. Hwang, Y., Catalano, C. E. & Feiss, M. Kinetic and mutational dissection of the two ATPase activities of terminase, the DNA packaging enzyme of bacteriophage lambda. Biochemistry 35, 2796-2803 (1996).
68. Sabanayagam, C. R., Oram, M., Lakowicz, J. R. & Black, L. W. Viral DNA packaging studied by fluorescence correlation spectroscopy. Biophys. J. 93, L17-L19 (2007).
69. Trus B L, Cheng N, Newcomb W W, Homa F L, Brown J C, Steven A C (2004) Structure and polymorphism of the UL6 portal protein of herpes simplex virus type 1. J Virol 78: 12668-12671
70. Dube P, Tavares P, Lurz R, van Heel M (1993) The portal protein of bacteriophage SPP1: a DNA pump with 13-fold symmetry. EMBO J 12: 1303-1309
71. Simpson A A, Leiman P G, Tao Y, He Y, Badasso M O, Jardine P J, Anderson D L, Rossmann M G (2001) Structure determination of the head-tail connector of bacteriophage phi29. Acta Crystallogr D57: 1260-1269
72. Orlova E V, Gowen B, Droge A, Stiege A, Weise F, Lurz R, van Heel M, Tavares P (2003) Structure of a viral DNA gatekeeper at 10 A° resolution by cryo-electron microscopy. EMBO J 22: 1255-1262
73. Andrey A Lebedev, Margret H Krause, Anabela L Isidro, Structural framework for DNA translocation via the viral portal protein.
74. Venigalla B. Rao, A virus DNA gate: zipping and unzipping the packed viral genome. PNAS, 2009 106: 8403-8404
75. Thieffry, M., Chich, J. F., Goldschmidt, D. & Henry, J. P. Incorporation in lipid bilayers of a large conductance cationic channel from mitochondrial membranes. EMBO J. 7, 1449-1454 (1988).
76. Hinnah, S. C. et al. The chloroplast protein import channel Toc75: Pore properties and interaction with transit peptides. Biophys. J. 83, 899-911 (2002).
77. Alcayaga, C., Venegas, R., Carrasco, A. & Wolff, D. Ion channels from the *Bacillus subtilis* plasma-membrane incorporated into planar lipid bilayers. FEBS Lett. 311, 246-250 (1992).
78. Benz, R., Schmid, A., Nakae, T. & Vosscherperkeuter, G. H. Pore formation by LamB of *Escherichia coli* in lipid bilayer membranes. J. Bacteriol. 165, 978-986 (1986).
79. Movileanu, L., Howorka, S., Braha, O. & Bayley, H. Detecting protein analytes that modulate transmembrane movement of a polymer chain within a single protein pore. Nature Biotechnol. 18, 1091-1095 (2000).
80. Wendell, D.; Jing, P.; Geng, J.; Subramaniam, V.; Lee, T. J.; Montemagno, C.; Guo, P. Translocation of Double-Stranded DNA through Membrane-Adapted Phi29 Motor Protein Nanopores. Nat. Nanotechnol. 2009, 4, 765-772.
81. Jing, P.; Haque, F.; Vonderheide, A.; Montemagno, C.; Guo, P. Robust Properties of Membrane-Embedded Connector Channel of Bacterial Virus Phi29 DNA Packaging Motor. Mol. BioSyst. 2010, 6, 1844-1852.
82. Jing, P.; Haque, F.; Shu, D.; Montemagno, C.; Guo, P. One-Way Traffic of a Viral Motor Channel for Double-Stranded DNA Translocation. Nano Lett. 2010, 10, 3620-3627.
83. Geng, J.; Fang, H.; Haque, F.; Zhang, L.; Guo, P. Three Reversible and Controllable Discrete Steps of Channel Gating of a Viral DNA Packaging Motor. Biomaterials 2011, 32, 8234-8242.
84. Orlova, E. V.; Gowen, B.; Droge, A.; Stiege, A.; Weise, F.; Lurz, R.; van, H. M.; Tavares, P. Structure of a Viral DNA Gatekeeper at 10 A Resolution by Cryo-Electron Microscopy. EMBO J. 2003, 22, 1255-1262.
85. Lurz, R.; Orlova, E. V.; Gunther, D.; Dube, P.; Droge, A.; Weise, F.; van Heel, M.; Tavares, P. Structural Organisation of the Head-to-Tail Interface of a Bacterial Virus 1. J. Mol Biol 2001, 310, 1027-1037.
86. Camacho, A. G.; Gual, A.; Lurz, R.; Tavares, P.; Alonso, J. C. *Bacillus Subtilis* Bacteriophage SPP1 DNA Packaging Motor Requires Terminase and Portal Proteins. J. Biol. Chem. 2003, 278, 23251-23259.
87. Guasch, A.; Pous, J.; Ibarra, B.; Gomis-Ruth, F. X.; Valpuesta, J. M.; Sousa, N.; Carrascosa, J. L.; Coll, M. Detailed Architecture of a DNA Translocating Machine: the High-Resolution Structure of the Bacteriophage Phi29 Connector Particle. J. Mol. Biol. 2002, 315, 663-676.
88. Valpuesta, J. M.; Fujisawa, H.; Marco, S.; Carazo, J. M.; Carrascosa, J. Three-Dimensional Structure of T3 Connector Purified From Overexpressing Bacteria. *J Mol Biol* 1992, 224, 103-112.
89. Olia, A. S.; Prevelige, P. E.; Johnson, J. E.; Cingolani, G. Three-Dimensional Structure of a Viral Genome-Delivery Portal Vertex. *Nat Struct Mol Biol* 2011, 18, 597-603.
90. Bazinet, C.; King, J. The DNA Translocation Vertex of DsDNA Bacteriophages. *Ann. Rev. Microbiol.* 1985, 39, 109-129.
91. De-Donatis, G.; Zhao, Z.; Wang, S.; Huang, P. L.; Schwartz, C.; Tsodikov, V. O.; Zhang, H.; Haque, F.; Guo, P. Finding of Widespread Viral and Bacterial Revolution DsDNA Translocation Motors Distinct From Rotation Motors by Channel Chirality and Size. *Cell Biosci* 2014, 4, 30.
92. Guo, P.; Zhao, Z.; Haak, J.; Wang, S.; Wu, D.; Meng, B.; Weitao, T. Common Mechanisms of DNA Translocation Motors in Bacteria and Viruses Using One-Way Revolution Mechanism Without Rotation. *Biotechnology Advances* 2014, 32, 853-872.
93. Zhao, Z.; Khisamutdinov, E.; Schwartz, C.; Guo, P. Mechanism of One-Way Traffic of Hexameric Phi29 DNA Packaging Motor With Four Electropositive Relaying Layers Facilitating Anti-Parallel Revolution. *ACS Nano* 2013, 7, 4082-4092.
94. Lebedev, A. A.; Krause, M. H.; Isidro, A. L.; Vagin, A. A.; Orlova, E. V.; Turner, J.; Dodson, E. J.; Tavares, P.; Antson, A. A. Structural Framework for DNA Translocation Via the Viral Portal Protein. *EMBO J.* 2007, 26, 1984-1994.
95. Lhuillier, S.; Gallopin, M.; Gilquin, B.; Brasiles, S.; Lancelot, N.; Letellier, G.; Gilles, M.; Dethan, G.; Orlova, E. V.; Couprie, J.; Tavares, P.; Zinn-Justin, S. Structure of Bacteriophage SPP1 Head-to-Tail Connection Reveals Mechanism for Viral DNA Gating. *Proc. Natl. Acad. Sci. U.S.A* 2009, 106, 8507-8512.
96. Astier, Y.; Braha, O.; Bayley, H. Toward Single Molecule DNA Sequencing: Direct Identification of Ribonucleoside and Deoxyribonucleoside 5'-Monophosphates by Using an Engineered Protein Nanopore Equipped With a Molecular Adapter. *J. Am. Chem. Soc.* 2006, 128, 1705-1710.
97. Clarke, J.; Wu, H. C.; Jayasinghe, L.; Patel, A.; Reid, S.; Bayley, H. Continuous Base Identification for Single-Molecule Nanopore DNA Sequencing. *Nat. Nanotechnol.* 2009, 4, 265-270.
98. Butler, T. Z.; Pavlenok, M.; Derrington, I. M.; Niederweis, M.; Gundlach, J. H. Single-Molecule DNA Detection With an Engineered MspA Protein Nanopore. *Proc. Natl. Acad. Sci. U.S.A* 2008, 105, 20647-20652.
99. Manrao, E. A.; Derrington, I. M.; Laszlo, A. H.; Langford, K. W.; Hopper, M. K.; Gillgren, N.; Pavlenok, M.; Niederweis, M.; Gundlach, J. H. Reading DNA at Single-Nucleotide Resolution With a Mutant MspA Nanopore and Phi29 DNA Polymerase. *Nat Biotechnol.* 2012, 30, 349-353.
100. Wendell, D.; Jing, P.; Geng, J.; Subramaniam, V.; Lee, T. J.; Montemagno, C.; Guo, P. Translocation of Double-Stranded DNA Through Membrane-Adapted Phi29 Motor Protein Nanopores. *Nat. Nanotechnol.* 2009, 4, 765-772.
101. Jing, P.; Haque, F.; Vonderheide, A.; Montemagno, C.; Guo, P. Robust Properties of Membrane-Embedded Connector Channel of Bacterial Virus Phi29 DNA Packaging Motor. *Mol. Biosyst.* 2010, 6, 1844-1852.
102. Jing, P.; Haque, F.; Shu, D.; Montemagno, C.; Guo, P. One-Way Traffic of a Viral Motor Channel for Double-Stranded DNA Translocation. *Nano Lett.* 2010, 10, 3620-3627.
103. Haque, F.; Lunn, J.; Fang, H.; Smithrud, D.; Guo, P. Real-Time Sensing and Discrimination of Single Chemicals Using the Channel of Phi29 DNA Packaging Nanomotor. *ACS Nano* 2012, 6, 3251-3261.

104. Geng, J.; Fang, H.; Haque, F.; Zhang, L.; Guo, P. Three Reversible and Controllable Discrete Steps of Channel Gating of a Viral DNA Packaging Motor. *Biomaterials* 2011, 32, 8234-8242.

105. Tobkes, N.; Wallace, B. A.; Bayley, H. Secondary Structure and Assembly Mechanism of an Oligomeric Channel Protein. *Biochemistry* 1985, 24, 1915-1920.

106. Uhlen, M.; Ponten, F. Antibody-Based Proteomics for Human Tissue Profiling. *Mol Cell Proteomics* 2005, 4, 384-393.

107. Barnham, K. J.; Kenche, V. B.; Ciccotosto, G. D.; Smith, D. P.; Tew, D. J.; Liu, X.; Perez, K.; Cranston, G. A.; Johanssen, T. J.; Volitakis, I.; Bush, A. I.; Masters, C. L.; White, A. R.; Smith, J. P.; Cherny, R. A.; Cappai, R. Platinum-Based Inhibitors of Amyloid-Beta As Therapeutic Agents for Alzheimer's Disease. *Proc. Natl. Acad. Sci. USA* 2008, 105, 6813-6818.

108. Archakov, A. I.; Ivanov, Y. D.; Lisitsa, A. V.; Zgoda, V. G. AFM Fishing Nanotechnology Is the Way to Reverse the Avogadro Number in Proteomics. *Proteomics* 2007, 7, 4-9.

109. Hendrix, R. W. Symmetry Mismatch and DNA Packaging in Large Bacteriophages. *Proc. Natl. Acad. Sci. USA* 1978, 75, 4779-4783.

110. Venkatesan, B. M.; Bashir, R. Nanopore Sensors for Nucleic Acid Analysis. *Nature Nanotechnology* 2011, 6, 615-624.

111. Haque, F.; Li, J.; Wu, H.-C.; Liang, X.-J.; Guo, P. Solid-State and Biological Nanopore for Real-Time Sensing of Single Chemical and Sequencing of DNA. *Nano Today* 2013, 8, 56-74.

112. Fang, H.; Jing, P.; Haque, F.; Guo, P. Role of Channel Lysines and "Push Through a One-Way Valve" Mechanism of Viral DNA Packaging Motor. *Biophysical Journal* 2012, 102, 127-135.

113. Braha, O.; Walker, B.; Cheley, S.; Kasianowicz, J. J.; Song, L.; Gouaux, J. E.; Bayley, H. Designed Protein Pores as Components for Biosensors. Chemistry & Biology 4, 497-505. 7-1-1997.
Ref Type: Abstract 114. Agirrezabala, X.; Martin-Benito, J.; Valle, M.; Gonzalez, J. M.; Valencia, A.; Valpuesta, J. M.; Carrascosa, J. L. Structure of the Connector of Bacteriophage T7 at 8A Resolution: Structural Homologies of a Basic Component of a DNA Translocating Machinery. *J. Mol Biol.* 2005, 347, 895-902.

115. Cingolani, G.; Moore, S. D.; Prevelige, J.; Johnson, J. E. Preliminary Crystallographic Analysis of the Bacteriophage P22 Portal Protein. *J Struct Biol* 2002, 139, 46-54.

116. Oliveira, L.; Henriques, A. O.; Tavares, P. Modulation of the Viral ATPase Activity by the Portal Protein Correlates With DNA Packaging Efficiency. *J Biol Chem* 2006, 281, 21914-21923.

117. Kowalczyk, S. W.; Tuijtel, M. W.; Donkers, S. P.; Dekker, C. Unraveling Single-Stranded DNA in a Solid-State Nanopore. *Nano Lett.* 2010, 10, 1414-1420.

118. Mathe, J.; Aksimentiev, A.; Nelson, D. R.; Schulten, K.; Meller, A. Orientation Discrimination of Single-Stranded DNA Inside the Alpha-Hemolysin Membrane Channel. *Proc. Natl. Acad. Sci. U.S.A* 2005, 102, 12377-12382.

119. Kawano, R.; Schibel, A. E. P.; Cauley, C.; White, H. S. Controlling the Translocation of Single-Stranded DNA Through +?Hemolysin Ion Channels Using Viscosity. *Langmuir* 2008, 25, 1233-1237.

120. Robinson, M. A.; Wood, J. P.; Capaldi, S. A.; Baron, A. J.; Gell, C.; Smith, D. A.; Stonehouse, N. J. Affinity of Molecular Interactions in the Bacteriophage Phi29 DNA Packaging Motor. *Nucleic Acids Res.* 2006, 34, 2698-2709.

121. Haque, F.; Geng, J.; Montemagno, C.; Guo, P. Incorporation of Viral DNA Packaging Motor Channel in Lipid Bilayers for Real-Time, Single-Molecule Sensing of Chemicals and Double-Stranded DNA. *Nat. Protoc.* 2013, 8, 373-392.

122. Earnshaw, W. C.; Casjens, S. R. DNA Packaging by the Double-Stranded DNA Bacteriophages. *Cell* 1980, 21, 319-331.

123. Guo, P.; Peterson, C.; Anderson, D. Prohead and DNA-Gp3-Dependent ATPase Activity of the DNA Packaging Protein Gp16 of Bacteriophage Phi29. *J Mol Biol* 1987, 197, 229-236.

124. Chemla, Y. R.; Aathavan, K.; Michaelis, J.; Grimes, S.; Jardine, P. J.; Anderson, D. L.; Bustamante, C. Mechanism of Force Generation of a Viral DNA Packaging Motor. *Cell.* 2005, 122, 683-692.

125. Hwang, Y.; Catalano, C. E.; Feiss, M. Kinetic and Mutational Dissection of the Two ATPase Activities of Terminase, the DNA Packaging Enzyme of Bacteriophage Lambda. *Biochemistry* 1996, 35, 2796-2803.

126. Sabanayagam, C. R.; Oram, M.; Lakowicz, J. R.; Black, L. W. Viral DNA Packaging Studied by Fluorescence Correlation Spectroscopy. *Biophys. J* 2007, 93, L17-L19.

127. Sun, S. Y.; Kondabagil, K.; Gentz, P. M.; Rossmann, M. G.; Rao, V. B. The Structure of the ATPase That Powers DNA Packaging into Bacteriophage T4 Procapsids. *Mol. Cell.* 2007, 25, 943-949.

128. Camacho, A. G.; Gual, A.; Lurz, R.; Tavares, P.; Alonso, J. C. *Bacillus Subtilis* Bacteriophage SPP1 DNA Packaging Motor Requires Terminase and Portal Proteins. *J. Biol. Chem.* 2003, 278, 23251-23259.

129. Guasch, A.; Pous, J.; Ibarra, B.; Gomis-Ruth, F. X.; Valpuesta, J. M.; Sousa, N.; Carrascosa, J. L.; Coll, M. Detailed Architecture of a DNA Translocating Machine: the High-Resolution Structure of the Bacteriophage Phi29 Connector Particle. *J. Mol. Biol.* 2002, 315, 663-676.

130. Valpuesta, J. M.; Fujisawa, H.; Marco, S.; Carazo, J. M.; Carrascosa, J. Three-Dimensional Structure of T3 Connector Purified From Overexpressing Bacteria. *J Mol Biol* 1992, 224, 103-112.

131. Olia, A. S.; Prevelige, P. E.; Johnson, J. E.; Cingolani, G. Three-Dimensional Structure of a Viral Genome-Delivery Portal Vertex. *Nat Struct Mol Biol* 2011, 18, 597-603.

132. Bazinet, C.; King, J. The DNA Translocation Vertex of DsDNA Bacteriophages. *Ann. Rev. Microbiol.* 1985, 39, 109-129.

133. De-Donatis, G.; Zhao, Z.; Wang, S.; Huang, P. L.; Schwartz, C.; Tsodikov, V. O.; Zhang, H.; Haque, F.; Guo, P. Finding of Widespread Viral and Bacterial Revolution DsDNA Translocation Motors Distinct From Rotation Motors by Channel Chirality and Size. *Cell Biosci* 2014, 4, 30.

134. Guo, P.; Zhao, Z.; Haak, J.; Wang, S.; Wu, D.; Meng, B.; Weitao, T. Common Mechanisms of DNA Translocation Motors in Bacteria and Viruses Using One-Way Revolution Mechanism Without Rotation. *Biotechnology Advances* 2014, 32, 853-872.

135. Zhao, Z.; Khisamutdinov, E.; Schwartz, C.; Guo, P. Mechanism of One-Way Traffic of Hexameric Phi29 DNA Packaging Motor With Four Electropositive Relaying Layers Facilitating Anti-Parallel Revolution. *ACS Nano* 2013, 7, 4082-4092.

136. Lebedev, A. A.; Krause, M. H.; Isidro, A. L.; Vagin, A. A.; Orlova, E. V.; Turner, J.; Dodson, E. J.; Tavares, P.; Antson, A. A. Structural Framework for DNA Translocation Via the Viral Portal Protein. *EMBO J.* 2007, 26, 1984-1994.

137. Lhuillier, S.; Gallopin, M.; Gilquin, B.; Brasiles, S.; Lancelot, N.; Letellier, G.; Gilles, M.; Dethan, G.; Orlova, E. V.; Couprie, J.; Tavares, P.; Zinn-Justin, S. Structure of Bacteriophage SPP1 Head-to-Tail Connection Reveals Mechanism for Viral DNA Gating. *Proc. Natl. Acad. Sci. U.S.A* 2009, 106, 8507-8512.

138. Hess, H.; Vogel, V. Molecular Shuttles Based on Motor Proteins: Active Transport in Synthetic Environments. *J Biotechnol.* 2001, 82, 67-85.

139. Soong, R. K.; Bachand, G. D.; Neves, H. P.; Olkhovets, A. G.; Craighead, H. G.; Montemagno, C. D. Powering an Inorganic Nanodevice With a Biomolecular Motor. *Science* 2000, 290, 1555-1558.

140. Wendell, D.; Jing, P.; Geng, J.; Subramaniam, V.; Lee, T. J.; Montemagno, C.; Guo, P. Translocation of Double-Stranded DNA Through Membrane-Adapted Phi29 Motor Protein Nanopores. *Nat. Nanotechnol.* 2009, 4, 765-772.

141. Jing, P.; Haque, F.; Vonderheide, A.; Montemagno, C.; Guo, P. Robust Properties of Membrane-Embedded Connector Channel of Bacterial Virus Phi29 DNA Packaging Motor. *Mol. Biosyst.* 2010, 6, 1844-1852.

142. Ali, M.; Ramirez, P.; Mafe, S.; Neumann, R.; Ensinger, W. A PH-Tunable Nanofluidic Diode With a Broad Range of Rectifying Properties. *ACS Nano* 2009, 3, 603-608.

143. Gracheva, M. E.; Vidal, J.; Leburton, J. P. P-n Semiconductor Membrane for Electrically Tunable Ion Current Rectification and Filtering. *Nano Lett.* 2007, 7, 1717-1722.

144. Yan, R.; Liang, W.; Fan, R.; Yang, P. Nanofluidic Diodes Based on Nanotube Heterojunctions. *Nano Lett.* 2009, 9, 3820-3825.

145. Maglia, G.; Heron, A. J.; Hwang, W. L.; Holden, M. A.; Mikhailova, E.; Li, Q.; Cheley, S.; Bayley, H. Droplet Networks With Incorporated Protein Diodes Show Collective Properties. *Nat. Nanotechnol.* 2009, 4, 437-440.

146. Aguilella, V. M.; Alcaraz, A. Nanobiotechnology: A Fluid Approach to Simple Circuits. *Nat. Nanotechnol.* 2009, 4, 403-404.

147. Miedema, H.; Vrouenraets, M.; Wierenga, J.; Meijberg, W.; Robillard, G.; Eisenberg, B. A Biological Porin Engineered into a Molecular, Nanofluidic Diode. *Nano Lett.* 2007, 7, 2886-2891.

148. Karnik, R.; Duan, C.; Castelino, K.; Daiguji, H.; Majumdar, A. Rectification of Ionic Current in a Nanofluidic Diode. *Nano Lett.* 2007, 7, 547-551.

149. Sparreboom, W.; van den, B. A.; Eijkel, J. C. Principles and Applications of Nanofluidic Transport. *Nat. Nanotechnol.* 2009, 4, 713-720.

150. Guo, P. X.; Lee, T. J. Viral Nanomotors for Packaging of DsDNA and DsRNA. *Mol. Microbiol.* 2007, 64, 886-903.

151. Tang, J. H.; Olson, N.; Jardine, P. J.; Girimes, S.; Anderson, D. L.; Baker, T. S. DNA Poised for Release in Bacteriophage Phi29. *Structure* 2008, 16, 935-943.

152. Tao, Y.; Olson, N. H.; Xu, W.; Anderson, D. L.; Rossmann, M. G.; Baker, T. S. Assembly of a Tailed Bacterial Virus and Its Genome Release Studied in Three Dimensions. *Cell* 1998, 95, 431-437.

153. Kemp, P.; Gupta, M.; Molineux, I. J. Bacteriophage T7 DNA Ejection into Cells Is Initiated by an Enzyme-Like Mechanism. *Mol. Microbiol.* 2004, 53, 1251-1265.

154. Cai, Y.; Xiao, F.; Guo, P. The Effect of N- or C-Terminal Alterations of the Connector of Bacteriophage Phi29 DNA Packaging Motor on Procapsid Assembly, PRNA Binding, and DNA Packaging. *Nanomedicine* 2008, 4, 8-18.

155. Guo, P. Introduction: Principles, Perspectives, and Potential Applications in Viral Assembly. *Seminars in Virology* (Editor's Introduction) 1994, 5(1), 1-3.

156. Guo, P.; Peterson, C.; Anderson, D. Prohead and DNA-Gp3-Dependent ATPase Activity of the DNA Packaging Protein Gp16 of Bacteriophage Phi29. *J Mol Biol* 1987, 197, 229-236.

157. Chemla, Y. R.; Aathavan, K.; Michaelis, J.; Grimes, S.; Jardine, P. J.; Anderson, D. L.; Bustamante, C. Mechanism of Force Generation of a Viral DNA Packaging Motor. *Cell.* 2005, 122, 683-692.

158. Hwang, Y.; Catalano, C. E.; Feiss, M. Kinetic and Mutational Dissection of the Two ATPase Activities of Terminase, the DNA Packaging Enzyme of Bacteriophage Lambda. *Biochemistry* 1996, 35, 2796-2803.

159. Sabanayagam, C. R.; Oram, M.; Lakowicz, J. R.; Black, L. W. Viral DNA Packaging Studied by Fluorescence Correlation Spectroscopy. *Biophys. J* 2007, 93, L17-L19.

160. Meifer, W. J. J.; Horcajadas, J. A.; Salas, M. Phi29 Family of Phages. *Microbiol. Mol. Biol Rev.* 2001, 65(2), 261-287.

161. Orlova, E. V.; Gowen, B.; Droge, A.; Stiege, A.; Weise, F.; Lurz, R.; van, H. M.; Tavares, P. Structure of a Viral DNA Gatekeeper at 10 A Resolution by Cryo-Electron Microscopy. *EMBO J.* 2003, 22, 1255-1262.

162. Lurz, R.; Orlova, E. V.; Gunther, D.; Dube, P.; Droge, A.; Weise, F.; van Heel, M.; Tavares, P. Structural Organisation of the Head-to-Tail Interface of a Bacterial Virus 1. *J Mol Biol* 2001, 310, 1027-1037.

163. Camacho, A. G.; Gual, A.; Lurz, R.; Tavares, P.; Alonso, J. C. *Bacillus Subtilis* Bacteriophage SPP1 DNA Packaging Motor Requires Terminase and Portal Proteins. *J. Biol. Chem.* 2003, 278, 23251-23259.

164. Guasch, A.; Pous, J.; Ibarra, B.; Gomis-Ruth, F. X.; Valpuesta, J. M.; Sousa, N.; Carrascosa, J. L.; Coll, M. Detailed Architecture of a DNA Translocating Machine: the High-Resolution Structure of the Bacteriophage Phi29 Connector Particle. *J. Mol. Biol.* 2002, 315, 663-676.

165. Valpuesta, J. M.; Fujisawa, H.; Marco, S.; Carazo, J. M.; Carrascosa, J. Three-Dimensional Structure of T3 Connector Purified From Overexpressing Bacteria. *J Mol Biol* 1992, 224, 103-112.

166. Olia, A. S.; Prevelige, P. E.; Johnson, J. E.; Cingolani, G. Three-Dimensional Structure of a Viral Genome-Delivery Portal Vertex. *Nat Struct Mol Biol* 2011, 18, 597-603.

167. Bazinet, C.; King, J. The DNA Translocation Vertex of DsDNA Bacteriophages. *Ann. Rev. Microbiol.* 1985, 39, 109-129.

168. De-Donatis, G.; Zhao, Z.; Wang, S.; Huang, P. L.; Schwartz, C.; Tsodikov, V. O.; Zhang, H.; Haque, F.; Guo, P. Finding of Widespread Viral and Bacterial Revolution DsDNA Translocation Motors Distinct From Rotation Motors by Channel Chirality and Size. *Cell Biosci* 2014, 4, 30.

169. Guo, P.; Zhao, Z.; Haak, J.; Wang, S.; Wu, D.; Meng, B.; Weitao, T. Common Mechanisms of DNA Translocation Motors in Bacteria and Viruses Using One-Way Revolution Mechanism Without Rotation. *Biotechnology Advances* 2014, 32, 853-872.

170. Zhao, Z.; Khisamutdinov, E.; Schwartz, C.; Guo, P. Mechanism of One-Way Traffic of Hexameric Phi29 DNA Packaging Motor With Four Electropositive Relaying Layers Facilitating Anti-Parallel Revolution. *ACS Nano* 2013, 7, 4082-4092.

171. Lebedev, A. A.; Krause, M. H.; Isidro, A. L.; Vagin, A. A.; Orlova, E. V.; Turner, J.; Dodson, E. J.; Tavares, P.; Antson, A. A. Structural Framework for DNA Translocation Via the Viral Portal Protein. *EMBO J.* 2007, 26, 1984-1994.

172. Lhuillier, S.; Gallopin, M.; Gilquin, B.; Brasiles, S.; Lancelot, N.; Letellier, G.; Gilles, M.; Dethan, G.; Orlova, E. V.; Couprie, J.; Tavares, P.; Zinn-Justin, S. Structure of Bacteriophage SPP1 Head-to-Tail Connection Reveals Mechanism for Viral DNA Gating. *Proc. Natl. Acad. Sci. U.S.A* 2009, 106, 8507-8512.

173. Alberts, B. *Molecular biology of the cell*; Garland Science: 2008.

174. Bertil Hille *Ion Channels of Excitable Membranes*; Sinauer Associates, Inc.: 2001.

175. Dorogi, P. L.; Neumann, E. Theoretical Implication of Liganding Reactions in Axonal Sodium Channel Gating. *Neurochemistry International* 1980, 2, 45-51.

176. Sokabe, M.; Sachs, F.; Jing, Z. Q. Quantitative Video Microscopy of Patch Clamped Membranes Stress, Strain, Capacitance, and Stretch Channel Activation. *Biophysical Journal* 1991, 59, 722-728.

177. Agnew, W. S.; Simon, R. L.; Brabson, J. S.; Raftery, M. A. Purification of the Tetrodotoxin-Binding Component Associated With the Voltage-Sensitive Sodium Channel From Electrophorus Electricus Electroplax Membranes. *Proceedings of the National Academy of Sciences of the United States of America* 1978, 75, 2606-2610.

178. Wendell, D.; Jing, P.; Geng, J.; Subramaniam, V.; Lee, T. J.; Montemagno, C.; Guo, P. Translocation of Double-Stranded DNA Through Membrane-Adapted Phi29 Motor Protein Nanopores. *Nat. Nanotechnol.* 2009, 4, 765-772.

179. Jing, P.; Haque, F.; Vonderheide, A.; Montemagno, C.; Guo, P. Robust Properties of Membrane-Embedded Connector Channel of Bacterial Virus Phi29 DNA Packaging Motor. *Mol. Biosyst.* 2010, 6, 1844-1852.

180. Jing, P.; Haque, F.; Shu, D.; Montemagno, C.; Guo, P. One-Way Traffic of a Viral Motor Channel for Double-Stranded DNA Translocation. *Nano Lett.* 2010, 10, 3620-3627.

181. Haque, F.; Lunn, J.; Fang, H.; Smithrud, D.; Guo, P. Real-Time Sensing and Discrimination of Single Chemicals Using the Channel of Phi29 DNA Packaging Nanomotor. *ACS Nano* 2012, 6, 3251-3261.

182. Fujisawa, H.; Morita, M. Phage DNA Packaging. *Genes Cells* 1997, 2, 537-545.

183. Khan, S. A.; Hayes, S. J.; Wright, E. T.; Watson, R. H.; Serwer, P. Specific Single-Stranded Breaks in Mature Bacteriophage T7 DNA. *Virology* 1995, 211, 329-331.

184. Oram, M.; Sabanayagam, C.; Black, L. W. Modulation of the Packaging Reaction of Bacteriophage T4 Terminase by DNA Structure. *J Mol Biol* 2008, 381, 61-72.

185. Astumian, R. D. Thermodynamics and Kinetics of a Brownian Motor. *Science* 1997, 276, 917-922.

186. Serwer, P. The Source of Energy for Bacteriophage DNA Packaging: an Osmotic Pump Explains the Data. *Biopolymers* 1988, 27, 165-169.

187. Hendrix, R. W. Symmetry Mismatch and DNA Packaging in Large Bacteriophages. *Proc. Natl. Acad. Sci. USA* 1978, 75, 4779-4783.

188. Grimes, S.; Anderson, D. The Bacteriophage Phi29 Packaging Proteins Supercoil the DNA Ends. *J Mol Biol* 1997, 266, 901-914.

189. Chen, C.; Guo, P. Sequential Action of Six Virus-Encoded DNA-Packaging RNAs During Phage Phi29 Genomic DNA Translocation. *J. Virol.* 1997, 71, 3864-3871.

190. Moffitt, J. R.; Chemla, Y. R.; Aathavan, K.; Grimes, S.; Jardine, P. J.; Anderson, D. L.; Bustamante, C. Intersubunit Coordination in a Homomeric Ring ATPase. *Nature* 2009, 457, 446-450.

191. Morita, M.; Tasaka, M.; Fujisawa, H. Structural and Functional Domains of the Large Subunit of the Bacteriophage T3 DNA Packaging Enzyme: Importance of the C-Terminal Region in Prohead Binding. *J. Mol. Biol.* 1995, 245, 635-644.

192. Yu, J.; Moffitt, J.; Hetherington, C. L.; Bustamante, C.; Oster, G. Mechanochemistry of a Viral DNA Packaging Motor. *J. Mol. Biol.* 2010, 400, 186-203.

193. Xiang, Y.; Morais, M. C.; Battisti, A. J.; Grimes, S.; Jardine, P. J.; Anderson, D. L.; Rossmann, M. G. Structural Changes of Bacteriophage Phi29 Upon DNA Packaging and Release. *EMBO J.* 2006, 25, 5229-5239.

194. Ding, F.; Lu, C.; Zhao, W.; Rajashankar, K. R.; Anderson, D. L.; Jardine, P. J.; Grimes, S.; Ke, A. Structure and Assembly of the Essential RNA Ring Component of a Viral DNA Packaging Motor. *Proc. Natl. Acad. Sci. U.S.A* 2011, 108, 7357-7362.

195. Zhao, H.; Finch, C. J.; Sequeira, R. D.; Johnson, B. A.; Johnson, J. E.; Casjens, S. R.; Tang, L. Crystal Structure of the DNA-Recognition Component of the Bacterial Virus Sf6 Genome-Packaging Machine. *Proc. Natl. Acad. Sci. U.S.A* 2010, 107, 1971-1976.

196. Maluf, N. K.; Gaussier, H.; Bogner, E.; Feiss, M.; Catalano, C. E. Assembly of Bacteriophage Lambda Terminase into a Viral DNA Maturation and Packaging Machine. *Biochemistry.* 2006, 45, 15259-15268.

197. Shu, D.; Zhang, H.; Jin, J.; Guo, P. Counting of Six PRNAs of Phi29 DNA-Packaging Motor With Customized Single Molecule Dual-View System. *EMBO J.* 2007, 26, 527-537.

198. Xiao, F.; Zhang, H.; Guo, P. Novel Mechanism of Hexamer Ring Assembly in Protein/RNA Interactions Revealed by Single Molecule Imaging. *Nucleic Acids Res* 2008, 36, 6620-6632.

199. Lowe, J.; Ellonen, A.; Allen, M. D.; Atkinson, C.; Sherratt, D. J.; Grainge, I. Molecular Mechanism of Sequence-Directed DNA Loading and Translocation by FtsK. *Mol. Cell* 2008, 31, 498-509.

200. Skordalakes, E.; Berger, J. M. Structural Insights into RNA-Dependent Ring Closure and ATPase Activation by the Rho Termination Factor. *Cell* 2006, 127, 553-564.

201. Matias, P. M.; Gorynia, S.; Donner, P.; Carrondo, M. A. Crystal Structure of the Human AAA+ Protein RuvBL1. *J. Biol. Chem.* 2006, 281, 38918-38929.

202. McGeoch, A. T.; Trakselis, M. A.; Laskey, R. A.; Bell, S. D. Organization of the Archaeal MCM Complex on DNA and Implications for the Helicase Mechanism. *Nat. Struct. Mol. Biol.* 2005, 12, 756-762.

203. Robinson, M. A.; Wood, J. P.; Capaldi, S. A.; Baron, A. J.; Gell, C.; Smith, D. A.; Stonehouse, N. J. Affinity of Molecular Interactions in the Bacteriophage Phi29 DNA Packaging Motor. *Nucleic Acids Res.* 2006, 34, 2698-2709.

204. Fang, Y.; Cai, Q.; Qin, P. Z. The Procapsid Binding Domain of Phi29 Packaging RNA Has a Modular Archi- 205. Fang, Y.; Shu, D.; Xiao, F.; Guo, P.; Qin, P. Z. Modular Assembly of Chimeric Phi29 Packaging RNAs That Support DNA Packaging. *Biochemical and Biophysical Research Communications* 2008, 372, 589-594.
206. Chen, C.; Sheng, S.; Shao, Z.; Guo, P. A Dimer As a Building Block in Assembling RNA: A Hexamer That Gears Bacterial Virus Phi29 DNA-Translocating Machinery. *J Biol Chem* 2000, 275(23), 17510-17516.
207. Dryden, K.; Wang, G.; Yeager, M.; Nibert, M.; Coombs, K.; Furlong, D.; Fields, B.; Baker, T. Early Steps in Reovirus Infection Are Associated With Dramatic Changes in Supramolecular Structure and Protein Conformation: Analysis of Virions and Subviral Particles by Cryoelectron Microscopy and Image Reconstruction. *J Cell Biol* 1993, 122, 1023-1041.
208. Jardine, P.; Coombs, D. H. Capsid Expansion Follows the Initiation of DNA Packaging in Bacteriophage T4. *J Mol. Biol* 1998, Dec. 4; 284(3), 661-672.
209. Tang, J. H.; Olson, N.; Jardine, P. J.; Girimes, S.; Anderson, D. L.; Baker, T. S. DNA Poised for Release in Bacteriophage Phi29. *Structure* 2008, 16, 935-943.
210. Ray, K.; Oram, M.; Ma, J.; Black, L. W. Portal Control of Viral Prohead Expansion and DNA Packaging. *Virology* 2009, 391, 44-50.
211. Serwer, P.; Wright, E. T.; Hakala, K.; Weintraub, S. T.; Su, M.; Jiang, W. DNA Packaging-Associated Hyper-Capsid Expansion of Bacteriophage T3. *J. Mol. Biol.* 2010, 397, 361-374.
212. Ionel, A.; Velazquez-Muriel, J. A.; Luque, D.; Cuervo, A.; Caston, J. R.; Valpuesta, J. M.; Martin-Benito, J.; Carrascosa, J. L. Molecular Rearrangements Involved in the Capsid Shell Maturation of Bacteriophage T7. *J. Biol. Chem.* 2011, 286, 234-242.
213. Zheng, H.; Olia, A. S.; Gonen, M.; Andrews, S.; Cingolani, G.; Gonen, T. A Conformational Switch in Bacteriophage P22 Portal Protein Primes Genome Injection. *Mol. Cell.* 2008, 29, 376-383.
214. Kemp, P.; Garcia, L. R.; Molineux, I. J. Changes in Bacteriophage T7 Virion Structure at the Initiation of Infection. *Virology* 2005, 340, 307-317.
215. Guo, P.; Erickson, S.; Xu, W.; Olson, N.; Baker, T. S.; Anderson, D. Regulation of the Phage Φ29 Prohead Shape and Size by the Portal Vertex. *Virology* 1991, 183, 366-373.

It will be understood that various details of the presently disclosed subject matter can be changed without departing from the scope of the subject matter disclosed herein. Furthermore, the foregoing description is for the purpose of illustration only, and not for the purpose of limitation.

SEQUENCE LISTING

Wild type SPP1 connector channel:
DNA sequence:

SEQ ID NO: 1

```
ATGGCTGATATCTACCCACTAGGGAAAACACACACAGAGGAACTGAATGAAATCATCGTAGAGAGCGC

GAAGGAGATCGCAGAACCGGACACAACCATGATCCAGAAGCTTATTGACGAACATAACCCGGAGCCGC

TATTGAAGGGCGTCCGGTACTACATGTGCGAGAACGACATTGAGAAGAAGCGGCGCACATACTACGAT

GCCGCAGGACAGCAATTAGTGGACGACACAAAGACCAATAACCGTACTAGCCACGCATGGCACAAGCT

GTTTGTGGATCAGAAAACACAGTACCTAGTGGGTGAGCCTGTTACATTCACATCAGACAATAAGACGT

TATTAGAGTACGTCAATGAGCTTGCAGACGACGACTTTGACGACATTTTGAACGAGACAGTCAAGAAT

ATGTCAAACAAGGGTATTGAATACTGGCATCCGTTCGTTGATGAAGAAGGGGAATTTGATTATGTTAT

TTTCCCGGCTGAGGAAATGATTGTTGTATACAAAGACAACACCCGCCGCGACATCCTTTTTGCCCTCC

GCTACTACTCATACAAGGGCATCATGGGTGAAGAGACACAGAAAGCAGAGCTGTACACAGACACACAC

GTTTACTACTACGAAAAAATTGACGGCGTTTATCAGATGGACTATTCATATGGCGAAAATAACCCCCG

GCCGCATATGACAAAGGGTGGACAAGCCATAGGATGGGGAAGAGTACCGATCATCCCGTTCAAAAACA

ATGAGGAAATGGTGTCCGATCTTAAATTCTACAAGGATTTAATCGACAATTACGACAGCATCACATCC

AGCACAATGGACTCATTCAGCGACTTCCAACAAATTGTGTACGTGCTCAAAAACTATGACGGGGAGAA

CCCGAAAGAATTCACGGCGAATTTAAGGTACCACAGTGTAATTAAGGTATCGGGCGATGGTGGTGTTG

ACACTTTACGGGCTGAAATACCTGTGGATAGTGCCGCAAAAGAGCTTGAAAGAATACAAGATGAGCTG

TATAAATCCGCTCAGGCTGTGGATAATTCACCAGAAACAATCGGAGGAGGGGCTACAGGCCCAGCACT

GGAAAACCTTTATGCGCTACTCGACTTGAAAGCGAACATGGCTGAACGGAAAATACGGGCTGGATTGC

GCTTGTTCTTTTGGTTCTTCGCTGAATACCTACGCAACACAGGGAAGGGCGATTTTAACCCGGATAAA

GAGCTTACAATGACGTTCACACGCACTAGGATTCAGAATGACAGCGAGATTGTTCAGAGTCTTGTACA

AGGCGTTACAGGTGGCATCATGAGTAAAGAGACGGCCGTCGCACGCAATCCATTTGTCCAAGACCCAG

AGGAAGAATTGGCCCGCATAGAAGAGGAAATGAACCAATACGCTGAAATGCAGGGCAACCTACTCGAC

GATGAGGGCGGGGATGATGATTTAGAGGAGGATGATCCAAATGCCGGAGCCGCAGAATCAGGAGGAGC
```

SEQUENCE LISTING

```
TGGACAAGTATCTTGA

Protein sequence:
                                                       SEQ ID NO: 2
MADIYPLGKTHTEELNEIIVESAKEIAEPDTTMIQKLIDEHNPEPLLKGVRYYMCENDIEKKRRTYYD

AAGQQLVDDTKTNNRTSHAWHKLFVDQKTQYLVGEPVTFTSDNKTLLEYVNELADDDFDDILNETVKN

MSNKGIEYWHPFVDEEGEFDYVIFPAEEMIVVYKDNTRRDILFALRYYSYKGIMGEETQKAELYTDTH

VYYYEKIDGVYQMDYSYGENNPRPHMTKGGQAIGWGRVPIIPFKNNEEMVSDLKFYKDLIDNYDSITS

STMDSFSDFQQIVYVLKNYDGENPKEFTANLRYHSVIKVSGDGGVDTLRAEIPVDSAAKELERIQDEL

YKSAQAVDNSPETIGGGATGPALENLYALLDLKANMAERDIRAGLRLFFWFFAEYLRNTGKGDFNPDK

ELTMTFTRTRIQNDSEIVQSLVQGVTGGIMSKETAVARNPFVQDPEEELARIEEEMNQYAEMQGNLLD

DEGGDDDLEEDDPNAGAAESGGAGQVS
```

1. Mutant 1 with added Gly-Gly-His-His-His-His-His-His
(SEQ ID NO: 14) on C-terminal (Gray labels indicate distinctions
relative to wild type)
DNA sequence:

```
                                                       SEQ ID NO: 3
ATGGCTGATATCTACCCACTAGGGAAAACACACAGAGGAACTGAATGAAATCATCGTAGAGAGCGC

GAAGGAGATCGCAGAACCGGACACAACCATGATCCAGAAGCTTATTGACGAACATAACCCGGAGCCGC

TATTGAAGGGCGTCCGGTACTACATGTGCGAGAACGACATTGAGAAGAAGCGGCGCACATACTACGAT

GCCGCAGGACAGCAATTAGTGGACGACACAAAGACCAATAACCGTACTAGCCACGCATGGCACAAGCT

GTTTGTGGATCAGAAAACACAGTACCTAGTGGGTGAGCCTGTTACATTCACATCAGACAATAAGACGT

TATTAGAGTACGTCAATGAGCTTGCAGACGACGACTTTGACGACATTTTGAACGAGACAGTCAAGAAT

ATGTCAAACAAGGGTATTGAATACTGGCATCCGTTCGTTGATGAAGAAGGGGAATTTGATTATGTTAT

TTTCCCGGCTGAGGAAATGATTGTTGTATACAAAGACAACACCCGCCGCGACATCCTTTTTGCCCTCC

GCTACTACTCATACAAGGGCATCATGGGTGAAGAGACACAGAAAGCAGAGCTGTACACAGACACACAC

GTTTACTACTACGAAAAAATTGACGGCGTTTATCAGATGGACTATTCGTATGGCGAAAATAACCCCCG

GCCGCACATGACAAAGGGTGGACAAGCCATAGGATGGGGAAGAGTACCGATCATCCCGTTCAAAAACA

ATGAGGAAATGGTGTCCGATCTTAAATTCTACAAGGATTTAATCGACAATTACGACAGCATCACATCC

AGCACAATGGACTCATTCAGCGACTTCCAACAAATTGTGTACGTGCTCAAAAACTATGACGGGGAGAA

CCCGAAAGAATTCACGGCGAATTTAAGGTACCACAGTGTAATTAAGGTATCGGGCGATGGTGGTGTTG

ACACTTTACGGGCTGAAATACCTGTGGATAGTGCCGCAAAAGAGCTTGAAAGAATACAAGATGAGCTG

TATAAATCCGCTCAGGCTGTGGATAATTCACCAGAAACAATCGGAGGAGGGCTACAGGCCCAGCACT

GGAAAACCTTTATGCGCTACTCGACTTGAAAGCGAACATGGCTGAACGGAAAATACGGGCTGGATTGC

GCTTGTTCTTTTGGTTCTTCGCTGAATACCTACGCAACACAGGGAAGGGCGATTTTAACCCGGATAAA

GAGCTTACAATGACGTTCACACGCACTAGGATTCAGAATGACAGCGAGATTGTTCAGAGTCTTGTACA

AGGCGTTACAGGTGGCATCATGAGTAAAGAGACGGCCGTCGCACGCAATCCATTTGTCCAAGACCCAG

AGGAAGAATTGGCCCGCATAGAAGAGGAAATGAACCAATACGCTGAAATGCAGGGCAACCTACTCGAC

GATGAGGGCGGGGATGATGATTTAGAGGAGGATGATCCAAATGCCGGAGCCGCAGAATCAGGAGGAGC

TGGACAAGTATCTGGTGGCCACCATCACCATCACCATTAG
```

Protein sequence:
                                                       SEQ ID NO: 4
MADIYPLGKTHTEELNEIIVESAKEIAEPDTTMIQKLIDEHNPEPLLKGVRYYMCENDIEKKRRTYYD

SEQUENCE LISTING

```
AAGQQLVDDTKTNNRTSHAWHKLFVDQKTQYLVGEPVTFTSDNKTLLEYVNELADDDFDDILNETVKN

MSNKGIEYWHPFVDEEGEFDYVIFPAEEMIVVYKDNTRRDILFALRYYSYKGIMGEETQKAELYTDTH

VYYYEKIDGVYQMDYSYGENNPRPHMTKGGQAIGWGRVPIIPFKNNEEMVSDLKFYKDLIDNYDSITS

STMDSFSDFQQIVYVLKNYDGENPKEFTANLRYHSVIKVSGDGGVDTLRAEIPVDSAAKELERIQDEL

YKSAQAVDNSPETIGGGATGPALENLYALLDLKANMAERKIRAGLRLFFWFFAEYLRNTGKGDFNPDK

ELTMTFTRTRIQNDSEIVQSLVQGVTGGIMSKETAVARNPFVQDPEEELARIEEEMNQYAEMQGNLLD

DEGGDDDLEEDDPNAGAAESGGAGQVSGGHHHHHH
```

2. Mutant 2 loop deletion.
DNA sequence:
SEQ ID NO: 5

```
ATGGCTGATATCTACCCACTAGGGAAAACACACACAGAGGAACTGAATGAAATCATCGTAGAGAGCGC

GAAGGAGATCGCAGAACCGGACACAACCATGATCCAGAAGCTTATTGACGAACATAACCCGGAGCCGC

TATTGAAGGCGTCCGGTACTACATGTGCGAGAACGACATTGAGAAGAAGCGGCGCACATACTACGAT

GCCGCAGGACAGCAATTAGTGGACGACACAAAGACCAATAACCGTACTAGCCACGCATGGCACAAGCT

GTTTGTGGATCAGAAAACACAGTACCTAGTGGGTGAGCCTGTTACATTCACATCAGACAATAAGACGT

TATTAGAGTACGTCAATGAGCTTGCAGACGACGACTTTGACGACATTTTGAACGAGACAGTCAAGAAT

ATGTCAAACAAGGGTATTGAATACTGGCATCCGTTCGTTGATGAAGAAGGGGAATTTGATTATGTTAT

TTTCCCGGCTGAGGAAATGATTGTTGTATACAAAGACAACACCCGCCGCGACATCCTTTTTGCCCTCC

GCTACTACTCATACAAGGGCATCATGGGTGAAGAGACACAGAAAGCAGAGCTGTACACAGACACACAC

GTTTACTACTACGAAAAAATTGACGGCGTTTATCAGATGGACTATTCGTATGGCGAAAATAACCCCCG

GCCGCAGATGACAAAGGGTGGACAAGCCATAGGATGGGGAAGAGTACCGATCATCCCGTTCAAAAACA

ATGAGGAAATGGTGTCCGATCTTAAATTCTACAAGGATTTAATCGACAATTACGACAGCATCACATCC

AGCACAATGGACTCATTCAGCGACTTCCAACAAATTGTGTACGTGCTCAAAAACTATGACGGGGAGAA

CCCGAAAGAATTCACGGCGAATTTAAGGTACCACAGTGTAATTAAGGTATCGGGCGATGGTGGTGTTG

ACACTTTACGGGCTGAAATACCTGTGGATAGTGCCGCAAAAGAGCTTGAAAGAATACAAGATGAGCTG

TATAAATCCGCT

GGCCCAGCACTGGAAAACCTTTATGCGCTACTCGACTTGAA

AGCGAACATGGCTGAACGGAAAATACGGGCTGGATTGCGCTTGTTCTTTTGGTTCTTCGCTGAATACC

TACGCAACACAGGGAAGGGCGATTTTAACCCGGATAAAGAGCTTACAATGACGTTCACACGCACTAGG

ATTCAGAATGACAGCGAGATTGTTCAGAGTCTTGTACAAGGCGTTACAGGTGGCATCATGAGTAAAGA

GACGGCCGTCGCACGCAATCCATTTGTCCAAGACCCAGAGGAAGAATTGGCCCCGCATAGAAGAGGAA

TGAACCAATACGCTGAAATGCAGGGCAACCTACTCGACGATGAGGGCGGGGATGATGATTTAGAGGAG

GATGATCCAAATGCCGGAGCCGCAGAATCAGGAGGAGCTGGACAAGTATCTGGTGGCCACCATCACCA

TCACCATTAG
```

Protein sequence:
SEQ ID NO: 6

```
MADIYPLGKTHTEELNEIIVESAKEIAEPDTTMIQKLIDEHNPEPLLKGVRYYMCENDIEKKRRTYYD

AAGQQLVDDTKTNNRTSHAWHKLFVDQKTQYLVGEPVTFTSDNKTLLEYVNELADDDFDDILNETVKN

MSNKGIEYWHPFVDEEGEFDYVIFPAEEMIVVYKDNTRRDILFALRYYSYKGIMGEETQKAELYTDTH

VYYYEKIDGVYQMDYSYGENNPRPHMTKGGQAIGWGRVPIIPFKNNEEMVSDLKFYKDLIDNYDSITS
```

STMDSFSDFQQIVYVLKNYDGENPKEFTANLRYHSVIKVSGDGGVDTLRAEIPVDSAAKELERIQDEL
YKSA
        GPALENLYALLDLKANMAERKIRAGLRLFFWFFAEYLRNTGKGDFNPDKELTMTFTRTR
IQNDSEIVQSLVQGVTGGIMSKETAVARNPFVQDPEEELARIEEEMNQYAEMQGNLLDDEGGDDDLEE
DDPNAGAAESGGAGQVSGGHHHHHH

3. Mutant 3-grey labeled is position of mutation(s)
E461G/E462G/E463G
DNA sequence:
SEQ ID NO: 7
ATGGCTGATATCTACCCACTAGGGAAAACACACACAGAGGAACTGAATGAAATCATCGTAGAGAGCGC
GAAGGAGATCGCAGAACCGGACACAACCATGATCCAGAAGCTTATTGACGAACATAACCCGGAGCCGC
TATTGAAGGGCGTCCGGTACTACATGTGCGAGAACGACATTGAGAAGAAGCGGCGCACATACTACGAT
GCCGCAGGACAGCAATTAGTGGACGACACAAAGACCAATAACCGTACTAGCCACGCATGGCACAAGCT
GTTTGTGGATCAGAAAACACAGTACCTAGTGGGTGAGCCTGTTACATTCACATCAGACAATAAGACGT
TATTAGAGTACGTCAATGAGCTTGCAGACGACGACTTTGACGACATTTTGAACGAGACAGTCAAGAAT
ATGTCAAACAAGGGTATTGAATACTGGCATCCGTTCGTTGATGAAGAAGGGGAATTTGATTATGTTAT
TTTCCCGGCTGAGGAAATGATTGTTGTATACAAAGACAACACCCGCCGCGACATCCTTTTTGCCCTCC
GCTACTACTCATACAAGGGCATCATGGGTGAAGAGACACAGAAAGCAGAGCTGTACACAGACACACAC
GTTTACTACTACGAAAAAATTGACGGCGTTTATCAGATGGACTATTCGTATGGCGAAAATAACCCCCG
GCCGCAGATGACAAAGGGTGGACAAGCCATAGGATGGGAAGAGTACCGATCATCCCGTTCAAAAACA
ATGAGGAAATGGTGTCCGATCTTAAATTCTACAAGGATTTAATCGACAATTACGACAGCATCACATCC
AGCACAATGGACTCATTCAGCGACTTCCAACAAATTGTGTACGTGCTCAAAAACTATGACGGGGAGAA
CCCGAAAGAATTCACGGCGAATTTAAGGTACCACAGTGTAATTAAGGTATCGGGCGATGGTGGTGTTG
ACACTTTACGGGCTGAAATACCTGTGGATAGTGCCGCAAAAGAGCTTGAAAGAATACAAGATGAGCTG
TATAAATCCGCTCAGGCTGTGGATAATTCACCAGAAACAATCGGAGGAGGGGCTACAGGCCCAGCACT
GGAAAACCTTTATGCGCTACTCGACTTGAAAGCGAACATGGCTGAACGGAAAATACGGGCTGGATTGC
GCTTGTTCTTTTGGTTCTTCGCTGAATACCTACGCAACACAGGGAAGGGCGATTTTAACCCGGATAAA
GAGCTTACAATGACGTTCACACGCACTAGGATTCAGAATGACAGCGAGATTGTTCAGAGTCTTGTACA
AGGCGTTACAGGTGGCATCATGAGTAAAGAGACGGCCGTCGCACGCAATCCATTTGTCCAAGACCCAG
AGGAAGAATTGGCCCGCATAGGAGGGGGAATGAACCAATACGCTGAAATGCAGGGCAACCTACTCGAC
GATGAGGGCGGGGATGATGATTTAGAGGAGGATGATCCAAATGCCGGAGCCGCAGAATCAGGAGGAGC
TGGACAAGTATCTGGTGGCCACCATCACCATCACCATTAC Protein sequence:
SEQ ID NO: 8
MADIYPLGKTHTEELNEIIVESAKEIAEPDTTMIQKLIDEHNPEPLLKGVRYYMCENDIEKKRRTYYD
AAGQQLVDDTKTNNRTSHAWHKLFVDQKTQYLVGEPVTFTSDNKTLLEYVNELADDDFDDILNETVKN
MSNKGIEYWHPFVDEEGEFDYVIFPAEEMIVVYKDNTRRDILFALRYYSYKGIMGEETQKAELYTDTH
VYYYEKIDGVYQMDYSYGENNPRPHMTKGGAQIGWGRVPIIPFKNNEEMVSDLKFYKDLIDNYDSITS
STMDSFSDFQQIVYVLKNYDGENPKEFTANLRYHSVIKVSGDGGVDTLRAEIPVDSAAKELERIQDEL

YKSAQAVDNSPETIGGGATGPALENLYALLDLKANMAERKIRAGLRLFFWFFAEYLRNTGKGDFNPDK

ELTMTFTRTRIQNDSEIVQSLVQGVTGGIMSKETAVARNPFVQDPEEELARIGGGMNQYAEMQGNLLD

DEGGDDDLEEDDPNAGAAESGGAGQVSGGHHHHHH

4. Mutant 4-grey labeled is position of mutation(s) D314N/D318N

SEQ ID NO: 9

ATGGCTGATATCTACCCACTAGGGAAAACACACACAGAGGAACTGAATGAAATCATCGTAGAGAGCGC

GAAGGAGATCGCAGAACCGGACACAACCATGATCCAGAAGCTTATTGACGAACATAACCCGGAGCCGC

TATTGAAGGCGTCCGGTACTACATGTGCGAGAACGACATTGAGAAGAAGCGGCGCACATACTACGAT

GCCGCAGGACAGCAATTAGTGGACGACACAAAGACCAATAACCGTACTAGCCACGCATGGCACAAGCT

GTTTGTGGATCAGAAAACACAGTACCTAGTGGGTGAGCCTGTTACATTCACATCAGACAATAAGACGT

TATTAGAGTACGTCAATGAGCTTGCAGACGACGACTTTGACGACATTTTGAACGAGACAGTCAAGAAT

ATGTCAAACAAGGGTATTGAATACTGGCATCCGTTCGTTGATGAAGAAGGGGAATTTGATTATGTTAT

TTTCCCGGCTGAGGAAATGATTGTTGTATACAAAGACAACACCCGCCGCGACATCCTTTTTGCCCTCC

GCTACTACTCATACAAGGGCATCATGGGTGAAGAGACACAGAAAGCAGAGCTGTACACAGACACACAC

GTTTACTACTACGAAAAAATTGACGGCGTTTATCAGATGGACTATTCGTATGGCGAAAATAACCCCCG

GCCGCAGATGACAAAGGGTGGACAAGCCATAGGATGGGAAGAGTACCGATCATCCCGTTCAAAAACA

ATGAGGAAATGGTGTCCGATCTTAAATTCTACAAGGATTTAATCGACAATTACGACAGCATCACATCC

AGCACAATGGACTCATTCAGCGACTTCCAACAAATTGTGTACGTGCTCAAAAACTATGACGGGGAGAA

CCCGAAAGAATTCACGGCGAATTTAAGGTACCACAGTGTAATTAAGGTATCGGGCAAUGGTGGTGTTA

ACACTTTACGGGCTGAAATACCTGTGGATAGTGCCGCAAAAGAGCTTGAAAGAATACAAGATGAGCTG

TATAAATCCGCTCAGGCTGTGGATAATTCACCAGAAACAATCGGAGGAGGGGCTACAGGCCCAGCACT

GGAAAACCTTTATGCGCTACTCGACTTGAAAGCGAACATGGCTGAACGGAAAATACGGGCTGGATTGC

GCTTGTTCTTTTGGTTCTTCGCTGAATACCTACGCAACACAGGGAAGGGCGATTTTAACCCGGATAAA

GAGCTTACAATGACGTTCACACGCACTAGGATTCAGAATGACAGCGAGATTGTTCAGAGTCTTGTACA

AGGCGTTACAGGTGGCATCATGAGTAAAGAGACGGCCGTCGCACGCAATCCATTTGTCCAAGACCCAG

AGGAAGAATTGGCCCGCATAGAAGAGGAAATGAACCAATACGCTGAAATGCAGGGCAACCTACTCGAC

GATGAGGGCGGGGATGATGATTTAGAGGAGGATGATCCAAATGCCGGAGCCGCAGAATCAGGAGGAGC

TGGACAAGTATCTGGTGGCCACCATCACCATCACCATTAG

Protein sequence:

SEQ ID NO: 10

MADIYPLGKTHTEELNEIIVESAKEIAEPDTTMIQKLIDEHNPEPLLKGVRYYMCENDIEKK

RRTYYDAAGQQLVDDTKTNNRTSHAWHKLFVDQKTQYLVGEPVTFTSDNKTLLEYVNELADDDFDDIL

NETVKNMSNKGIEYWHPFVDEEGEFDYVIFPAEEMIVVYKDNTRRDILFALRYYSYKGIMGEETQKAE

LYTDTHVYYYEKIDGVYQMDYSYGENNPRPHMTKGGQAIGWGRVPIIPFKNNEEMVSDLKFYKDLIDN

YDSITSSTMDSFSDFQQIVYVLKNYDGENPKEFTANLRYHSVIKVSGNGGVNTLRAEIPVDSAAKELE

RIQDELYKSAQAVDNSPETIGGGATGPALENLYALLDLKANMAERKIRAGLRLFFWFFAEYLRNTGKG

DFNPDKELTMTFTRTRIQNDSEIVQSLVQGVTGGIMSKETAVARNPFVQDPEEELARIEEEMNQYAEM

QGNLLDDEGGDDDLEEDDPNAGAAESGGAGQVSGGHHHHHH

What is claimed is:

1. A nucleic acid molecule encoding a SPP1 connector polypeptide variant, wherein the polypeptide comprises the amino acid sequence of SEQ ID NO:6, SEQ ID NO:8, or SEQ ID NO:10.

2. The nucleic acid molecule of claim 1, having the sequence of SEQ ID NO:5, SEQ ID NO:7, or SEQ ID NO:9.

3. A SPP1 connector polypeptide variant, wherein the polypeptide comprises the amino acid sequence of SEQ ID NO:6, SEQ ID NO:8, or SEQ ID NO:10.

4. A SPP1 connector polypeptide variant, wherein the polypeptide comprises an amino acid sequence encoded by a nucleic acid molecule having the sequence of SEQ ID NO:5, SEQ ID NO:7, or SEQ ID NO:9.

5. A conductive channel-containing membrane, comprising:
   (a) a membrane layer; and
   (b) a SPP1 connector polypeptide variant that is incorporated into the membrane layer to form an aperture through which conductance can occur when an electrical potential is applied across the membrane, wherein the SPP1 connector polypeptide variant is selected from:
      a polypeptide comprising the amino acid sequence of SEQ ID NO:6, SEQ ID NO:8, or SEQ ID NO:10; and
      a polypeptide comprising an amino acid sequence encoded by a nucleic acid molecule having the sequence of SEQ ID NO:5, SEQ ID NO:7, or SEQ ID NO:9.

6. The conductive channel-containing membrane of claim 5, wherein SPP1 connector polypeptide variant comprises a detectable label.

7. The conductive channel-containing membrane of claim 6, wherein the detectable label is selected from the group consisting of a colorimetric indicator, a GCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label.

8. The conductive channel-containing membrane of claim 5, wherein the membrane layer comprises a lipid layer.

9. The conductive channel-containing membrane of claim 8, wherein the lipid layer comprises amphipathic lipids.

10. The conductive channel-containing membrane of claim 9, wherein the amphipathic lipids comprise phospholipids and the lipid layer comprises a lipid bilayer.

11. The conductive channel-containing membrane of claim 8, wherein the lipid layer is selected from the group consisting of a planar membrane layer and a liposome.

12. The conductive channel-containing membrane of claim 11, wherein the liposome is selected from the group consisting of a multilamellar liposome and a unilamellar liposome.

13. The conductive channel-containing membrane of claim 5, wherein the incorporated SPP1 connector polypeptide variant is mobile in the membrane layer.

14. The conductive channel-containing membrane of claim 5, which is capable of translocating a single stranded nucleic acid molecule, a double-stranded nucleic acid molecule, and/or a polypeptide through the aperture when the electrical potential is applied, wherein said conductive channel-containing membrane is capable of polypeptide detection, identification, sequencing, and discrimination.

* * * * *

SEQUENCE LISTING

<160> NUMBER OF SEQ ID NOS: 14

<210> SEQ ID NO 1
<211> LENGTH: 1512
<212> TYPE: DNA
<213> ORGANISM: Unknown
<220> FEATURE:
<223> OTHER INFORMATION: Description of Unknown:
      Wild type SPP1 connector channel sequence

<400> SEQUENCE: 1

```
atggctgata tctacccact agggaaaaca cacacagagg aactgaatga aatcatcgta      60
gagagcgcga aggagatcgc agaaccggac acaaccatga tccagaagct tattgacgaa     120
cataaccccgg agccgctatt gaagggcgtc cggtactaca tgtgcgagaa cgacattgag    180
aagaagcggc gcacatacta cgatgccgca ggacagcaat tagtggacga cacaaagacc    240
aataaccgta ctagccacgc atggcacaag ctgtttgtgg atcagaaaac acagtaccta    300
gtgggtgagc ctgttacatt cacatcagac aataagacgt tattagagta cgtcaatgag    360
cttgcagacg acgactttga cgacattttg aacgagacag tcaagaatat gtcaaacaag    420
ggtattgaat actggcatcc gttcgttgat gaagaagggg aatttgatta tgttattttc    480
ccggctgagg aaatgattgt tgtatacaaa gacaacaccc gccgcgacat ccttttttgcc   540
ctccgctact actcatacaa gggcatcatg ggtgaagaga cacagaaagc agagctgtac    600
acagacacac acgtttacta ctacgaaaaa attgacggcg tttatcagat ggactattca    660
tatggcgaaa ataaccccccg gccgcatatg acaaagggtg acaagccat aggatgggga    720
agtaccga tcatcccgtt caaaaacaat gaggaaatgg tgtccgatct taaattctac     780
aaggatttaa tcgacaatta cgacagcatc acatccagca aatggactc attcagcgac    840
ttccaacaaa ttgtgtacgt gctcaaaaac tatgacgggg agaacccgaa agaattcacg    900
gcgaatttaa ggtaccacag tgtaattaag gtatcgggcg atggtggtgt tgacactta     960
cgggctgaaa tacctgtgga tagtgccgca aaagagcttg aaagaataca agatgagctg   1020
tataaatccg ctcaggctgt ggataattca ccagaaacaa tcggaggagg ggctacaggc   1080
ccagcactgg aaaaccttta tgcgctactc gacttgaaag cgaacatggc tgaacggaaa   1140
atacgggctg gattgcgctt gttcttttgg ttcttcgctg aatacctacg caacacaggg   1200
aagggcgatt ttaacccgga taagagctt acaatgacgt tcacacgcac taggattcag   1260
aatgacagcg agattgttca gagtcttgta caaggcgtta caggtggcat catgagtaaa   1320
gagacggccg tcgcacgcaa tccatttgtc caagacccag aggaagaatt ggcccgcata   1380
gaagaggaaa tgaaccaata cgctgaaatg cagggcaacc tactcgacga tgagggcggg   1440
gatgatgatt tagaggagga tgatccaaat gccggagccg cagaatcagg aggagctgga   1500
caagtatctt ga                                                       1512
```

<210> SEQ ID NO 2
<211> LENGTH: 503
<212> TYPE: PRT
<213> ORGANISM: Unknown
<220> FEATURE:
<223> OTHER INFORMATION: Description of Unknown:
    Wild type SPP1 connector channel sequence

<400> SEQUENCE: 2

Met Ala Asp Ile Tyr Pro Leu Gly Lys Thr His Thr Glu Glu Leu Asn
1               5                   10                  15

Glu Ile Ile Val Glu Ser Ala Lys Glu Ile Ala Glu Pro Asp Thr Thr
            20                  25                  30

Met Ile Gln Lys Leu Ile Asp Glu His Asn Pro Glu Pro Leu Leu Lys
        35                  40                  45

Gly Val Arg Tyr Tyr Met Cys Glu Asn Asp Ile Glu Lys Lys Arg Arg
    50                  55                  60

Thr Tyr Tyr Asp Ala Ala Gly Gln Gln Leu Val Asp Asp Thr Lys Thr
65                  70                  75                  80

Asn Asn Arg Thr Ser His Ala Trp His Lys Leu Phe Val Asp Gln Lys
                85                  90                  95

Thr Gln Tyr Leu Val Gly Glu Pro Val Thr Phe Thr Ser Asp Asn Lys
            100                 105                 110

Thr Leu Leu Glu Tyr Val Asn Glu Leu Ala Asp Asp Phe Asp Asp
        115                 120                 125

Ile Leu Asn Glu Thr Val Lys Asn Met Ser Asn Lys Gly Ile Glu Tyr
    130                 135                 140

Trp His Pro Phe Val Asp Glu Gly Glu Phe Asp Tyr Val Ile Phe
145                 150                 155                 160

Pro Ala Glu Glu Met Ile Val Val Tyr Lys Asp Asn Thr Arg Arg Asp
                165                 170                 175

Ile Leu Phe Ala Leu Arg Tyr Tyr Ser Tyr Lys Gly Ile Met Gly Glu
            180                 185                 190

Glu Thr Gln Lys Ala Glu Leu Tyr Thr Asp Thr His Val Tyr Tyr Tyr
        195                 200                 205

Glu Lys Ile Asp Gly Val Tyr Gln Met Asp Tyr Ser Tyr Gly Glu Asn
    210                 215                 220

Asn Pro Arg Pro His Met Thr Lys Gly Gly Gln Ala Ile Gly Trp Gly
225                 230                 235                 240

Arg Val Pro Ile Ile Pro Phe Lys Asn Asn Glu Glu Met Val Ser Asp
                245                 250                 255

Leu Lys Phe Tyr Lys Asp Leu Ile Asp Asn Tyr Asp Ser Ile Thr Ser
            260                 265                 270

Ser Thr Met Asp Ser Phe Ser Asp Phe Gln Gln Ile Val Tyr Val Leu
        275                 280                 285

Lys Asn Tyr Asp Gly Glu Asn Pro Lys Glu Phe Thr Ala Asn Leu Arg
    290                 295                 300

Tyr His Ser Val Ile Lys Val Ser Gly Asp Gly Val Asp Thr Leu
305                 310                 315                 320

Arg Ala Glu Ile Pro Val Asp Ser Ala Ala Lys Glu Leu Glu Arg Ile
                325                 330                 335

Gln Asp Glu Leu Tyr Lys Ser Ala Gln Ala Val Asp Asn Ser Pro Glu
            340                 345                 350

Thr Ile Gly Gly Gly Ala Thr Gly Pro Ala Leu Glu Asn Leu Tyr Ala
        355                 360                 365

Leu Leu Asp Leu Lys Ala Asn Met Ala Glu Arg Lys Ile Arg Ala Gly
        370                 375                 380

Leu Arg Leu Phe Phe Trp Phe Phe Ala Glu Tyr Leu Arg Asn Thr Gly
385                 390                 395                 400

Lys Gly Asp Phe Asn Pro Asp Lys Glu Leu Thr Met Thr Phe Thr Arg
                405                 410                 415

Thr Arg Ile Gln Asn Asp Ser Glu Ile Val Gln Ser Leu Val Gln Gly
            420                 425                 430

Val Thr Gly Gly Ile Met Ser Lys Glu Thr Ala Val Ala Arg Asn Pro
                435                 440                 445

Phe Val Gln Asp Pro Glu Glu Leu Ala Arg Ile Glu Glu Glu Met
450                 455                 460

Asn Gln Tyr Ala Glu Met Gln Gly Asn Leu Leu Asp Asp Glu Gly Gly
465                 470                 475                 480

Asp Asp Asp Leu Glu Glu Asp Asp Pro Asn Ala Gly Ala Ala Glu Ser
                485                 490                 495

Gly Gly Ala Gly Gln Val Ser
            500

<210> SEQ ID NO 3
<211> LENGTH: 1536
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggctgata tctacccact agggaaaaca cacacagagg aactgaatga aatcatcgta      60
gagagcgcga aggagatcgc agaaccggac acaaccatga tccagaagct tattgacgaa    120
cataacccgg agccgctatt gaagggcgtc cggtactaca tgtgcgagaa cgacattgag    180
aagaagcggc gcacatacta cgatgccgca ggacagcaat tagtggacga cacaaagacc    240
aataaccgta ctagccacgc atggcacaag ctgtttgtgg atcagaaaac acagtaccta    300
gtgggtgagc tgttacatt cacatcagac aataagacgt tattgagta cgtcaatgag    360 cttgcagacg acgactttga cgacattttg aacgagacag tcaagaatat gtcaaacaag    420
ggtattgaat actggcatcc gttcgttgat gaagaagggg aatttgatta tgttattttc    480
ccggctgagg aaatgattgt tgtatacaaa gacaacaccc gccgcgacat cctttttgcc    540
ctccgctact actcatacaa gggcatcatg ggtgaagaga cacagaaagc agagctgtac    600
acagacacac acgtttacta ctacgaaaaa attgacggcg tttatcagat ggactattcg    660
tatggcgaaa ataacccccg gccgcacatg acaaagggtg acaagccat aggatgggga    720 agagtaccga tcatcccgtt caaaaacaat gaggaaatgg tgtccgatct aaattctac    780 aaggatttaa tcgacaatta cgacagcatc acatccagca caatggactc attcagcgac    840
ttccaacaaa ttgtgtacgt gctcaaaaac tatgacgggg agaacccgaa agaattcacg    900
gcgaatttaa ggtaccacag tgtaattaag gtatcgggcg atggtggtgt tgacactta    960 cgggctgaaa tacctgtgga tagtgccgca aaagagcttg aaagaataca agatgagctg   1020
tataaatccg ctcaggctgt ggataattca ccagaaacaa tcggaggagg ggctacaggc   1080
ccagcactgg aaaaccttta tgcgctactc gacttgaaag cgaacatggc tgaacggaaa   1140
atacgggctg gattgcgctt gttctttttgg ttcttcgctg aatacctacg caacacaggg   1200
aagggcgatt ttaacccgga taagagctt acaatgacgt tcacacgcac taggattcag   1260

-continued

```
aatgacagcg agattgttca gagtcttgta caaggcgtta caggtggcat catgagtaaa    1320
gagacggccg tcgcacgcaa tccatttgtc caagacccag aggaagaatt ggcccgcata    1380
gaagaggaaa tgaaccaata cgctgaaatg cagggcaacc tactcgacga tgagggcggg    1440
gatgatgatt tagaggagga tgatccaaat gccggagccg cagaatcagg aggagctgga    1500
caagtatctg gtggccacca tcaccatcac cattag                             1536
```

<210> SEQ ID NO 4
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Ala Asp Ile Tyr Pro Leu Gly Lys Thr His Thr Glu Glu Leu Asn
1               5                   10                  15

Glu Ile Ile Val Glu Ser Ala Lys Glu Ile Ala Glu Pro Asp Thr Thr
            20                  25                  30

Met Ile Gln Lys Leu Ile Asp Glu His Asn Pro Glu Pro Leu Leu Lys
        35                  40                  45

Gly Val Arg Tyr Tyr Met Cys Glu Asn Asp Ile Glu Lys Lys Arg Arg
    50                  55                  60

Thr Tyr Tyr Asp Ala Ala Gly Gln Gln Leu Val Asp Thr Lys Thr
65                  70                  75                  80

Asn Asn Arg Thr Ser His Ala Trp His Lys Leu Phe Val Asp Gln Lys
                85                  90                  95

Thr Gln Tyr Leu Val Gly Glu Pro Val Thr Phe Thr Ser Asp Asn Lys
            100                 105                 110

Thr Leu Leu Glu Tyr Val Asn Glu Leu Ala Asp Asp Phe Asp Asp
        115                 120                 125

Ile Leu Asn Glu Thr Val Lys Asn Met Ser Asn Lys Gly Ile Glu Tyr
    130                 135                 140

Trp His Pro Phe Val Asp Glu Glu Gly Glu Phe Asp Tyr Val Ile Phe
145                 150                 155                 160

Pro Ala Glu Glu Met Ile Val Val Tyr Lys Asp Asn Thr Arg Arg Asp
                165                 170                 175

Ile Leu Phe Ala Leu Arg Tyr Tyr Ser Tyr Lys Gly Ile Met Gly Glu
            180                 185                 190

Glu Thr Gln Lys Ala Glu Leu Tyr Thr Asp Thr His Val Tyr Tyr Tyr
        195                 200                 205

Glu Lys Ile Asp Gly Val Tyr Gln Met Asp Tyr Ser Tyr Gly Glu Asn
    210                 215                 220

Asn Pro Arg Pro His Met Thr Lys Gly Gly Gln Ala Ile Gly Trp Gly
225                 230                 235                 240

Arg Val Pro Ile Ile Pro Phe Lys Asn Asn Glu Glu Met Val Ser Asp
                245                 250                 255

Leu Lys Phe Tyr Lys Asp Leu Ile Asp Asn Tyr Asp Ser Ile Thr Ser
            260                 265                 270

Ser Thr Met Asp Ser Phe Ser Asp Phe Gln Gln Ile Val Tyr Val Leu
        275                 280                 285

Lys Asn Tyr Asp Gly Glu Asn Pro Lys Glu Phe Thr Ala Asn Leu Arg
    290                 295                 300
```

```
Tyr His Ser Val Ile Lys Val Ser Gly Asp Gly Val Asp Thr Leu
305                 310                 315                 320

Arg Ala Glu Ile Pro Val Asp Ser Ala Ala Lys Glu Leu Glu Arg Ile
            325                 330                 335

Gln Asp Glu Leu Tyr Lys Ser Ala Gln Ala Val Asp Asn Ser Pro Glu
            340                 345                 350

Thr Ile Gly Gly Gly Ala Thr Gly Pro Ala Leu Glu Asn Leu Tyr Ala
            355                 360                 365

Leu Leu Asp Leu Lys Ala Asn Met Ala Glu Arg Lys Ile Arg Ala Gly
            370                 375                 380

Leu Arg Leu Phe Phe Trp Phe Phe Ala Glu Tyr Leu Arg Asn Thr Gly
385                 390                 395                 400

Lys Gly Asp Phe Asn Pro Asp Lys Glu Leu Thr Met Thr Phe Thr Arg
                405                 410                 415

Thr Arg Ile Gln Asn Asp Ser Glu Ile Val Gln Ser Leu Val Gln Gly
            420                 425                 430

Val Thr Gly Gly Ile Met Ser Lys Glu Thr Ala Val Ala Arg Asn Pro
            435                 440                 445

Phe Val Gln Asp Pro Glu Glu Glu Leu Ala Arg Ile Glu Glu Glu Met
450                 455                 460

Asn Gln Tyr Ala Glu Met Gln Gly Asn Leu Leu Asp Asp Glu Gly Gly
465                 470                 475                 480

Asp Asp Asp Leu Glu Glu Asp Asp Pro Asn Ala Gly Ala Ala Glu Ser
                485                 490                 495

Gly Gly Ala Gly Gln Val Ser Gly Gly His His His His His His
            500                 505                 510

<210> SEQ ID NO 5
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggctgata tctacccact agggaaaaca cacacagagg aactgaatga aatcatcgta      60
gagagcgcga aggagatcgc agaaccggac acaaccatga tccagaagct tattgacgaa     120
cataacccgg agccgctatt gaagggcgtc cggtactaca tgtgcgagaa cgacattgag     180
aagaagcggc gcacatacta cgatgccgca ggacagcaat tagtggacga cacaaagacc     240
aataaccgta ctagccacgc atggcacaag ctgtttgtgg atcagaaaac acagtaccta     300
gtgggtgagc ctgttacatt cacatcagac aataagacgt tattagagta cgtcaatgag     360
cttgcagacg acgactttga cgacattttg aacgagacag tcaagaatat gtcaaacaag     420
ggtattgaat actggcatcc gttcgttgat gaagaagggg aatttgatta tgttattttc     480
ccggctgagg aaatgattgt tgtatacaaa gacaacaccc gccgcgacat ccttttttgcc     540 ctccgctact actcatacaa gggcatcatg ggtgaagaga cacagaaagc agagctgtac     600
acagacacac acgtttacta ctacgaaaaa attgacggcg tttatcagat ggactattcg     660
tatggcgaaa ataaccccg gccgcacatg acaaagggtg acaagccat aggatgggga     720 agagtaccga tcatcccgtt caaaaacaat gaggaaatgg tgtccgatct taaattctac     780
aaggatttaa tcgacaatta cgacagcatc acatccagca aatggactc attcagcgac     840 ttccaacaaa ttgtgtacgt gctcaaaaac tatgacgggg agaacccgaa agaattcacg     900
```

```
gcgaatttaa ggtaccacag tgtaattaag gtatcgggcg atggtggtgt tgacacttta    960
cgggctgaaa tacctgtgga tagtgccgca aaagagcttg aaagaataca agatgagctg   1020
tataaatccg ctggcccagc actggaaaac ctttatgcgc tactcgactt gaaagcgaac   1080
atggctgaac ggaaaatacg ggctggattg cgcttgttct tttggttctt cgctgaatac   1140
ctacgcaaca cagggaaggg cgattttaac ccggataaag agcttacaat gacgttcaca   1200
cgcactagga ttcagaatga cagcgagatt gttcagagtc ttgtacaagg cgttacaggt   1260
ggcatcatga gtaaagagac ggccgtcgca cgcaatccat ttgtccaaga cccagaggaa   1320
gaattggccc gcatagaaga ggaaatgaac caatacgctg aaatgcaggg caacctactc   1380
gacgatgagg gcggggatga tgatttagag gaggatgatc caaatgccgg agccgcagaa   1440
tcaggaggag ctggacaagt atctggtggc caccatcacc atcaccatta g            1491
```

<210> SEQ ID NO 6
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ala Asp Ile Tyr Pro Leu Gly Lys Thr His Thr Glu Glu Leu Asn
1               5                   10                  15

Glu Ile Ile Val Glu Ser Ala Lys Glu Ile Ala Glu Pro Asp Thr Thr
            20                  25                  30

Met Ile Gln Lys Leu Ile Asp Glu His Asn Pro Glu Pro Leu Leu Lys
        35                  40                  45

Gly Val Arg Tyr Tyr Met Cys Glu Asn Asp Ile Glu Lys Lys Arg Arg
    50                  55                  60

Thr Tyr Tyr Asp Ala Ala Gly Gln Gln Leu Val Asp Asp Thr Lys Thr
65                  70                  75                  80

Asn Asn Arg Thr Ser His Ala Trp His Lys Leu Phe Val Asp Gln Lys
                85                  90                  95

Thr Gln Tyr Leu Val Gly Glu Pro Val Thr Phe Thr Ser Asp Asn Lys
            100                 105                 110

Thr Leu Leu Glu Tyr Val Asn Glu Leu Ala Asp Asp Phe Asp Asp
        115                 120                 125

Ile Leu Asn Glu Thr Val Lys Asn Met Ser Asn Lys Gly Ile Glu Tyr
    130                 135                 140

Trp His Pro Phe Val Asp Glu Glu Gly Glu Phe Asp Tyr Val Ile Phe
145                 150                 155                 160

Pro Ala Glu Glu Met Ile Val Val Tyr Lys Asp Asn Thr Arg Arg Asp
                165                 170                 175

Ile Leu Phe Ala Leu Arg Tyr Tyr Ser Tyr Lys Gly Ile Met Gly Glu
            180                 185                 190

Glu Thr Gln Lys Ala Glu Leu Tyr Thr Asp Thr His Val Tyr Tyr Tyr
        195                 200                 205

Glu Lys Ile Asp Gly Val Tyr Gln Met Asp Tyr Ser Tyr Gly Glu Asn
    210                 215                 220

Asn Pro Arg Pro His Met Thr Lys Gly Gly Gln Ala Ile Gly Trp Gly
225                 230                 235                 240

Arg Val Pro Ile Ile Pro Phe Lys Asn Asn Glu Glu Met Val Ser Asp
                245                 250                 255
```

Leu Lys Phe Tyr Lys Asp Leu Ile Asp Asn Tyr Asp Ser Ile Thr Ser
            260                 265                 270

Ser Thr Met Asp Ser Phe Ser Asp Phe Gln Gln Ile Val Tyr Val Leu
            275                 280                 285

Lys Asn Tyr Asp Gly Glu Asn Pro Lys Glu Phe Thr Ala Asn Leu Arg
            290                 295                 300

Tyr His Ser Val Ile Lys Val Ser Gly Asp Gly Val Asp Thr Leu
305                 310                 315                 320

Arg Ala Glu Ile Pro Val Asp Ser Ala Ala Lys Glu Leu Glu Arg Ile
            325                 330                 335

Gln Asp Glu Leu Tyr Lys Ser Ala Gly Pro Ala Leu Glu Asn Leu Tyr
            340                 345                 350

Ala Leu Leu Asp Leu Lys Ala Asn Met Ala Glu Arg Lys Ile Arg Ala
            355                 360                 365

Gly Leu Arg Leu Phe Phe Trp Phe Ala Glu Tyr Leu Arg Asn Thr
370                 375                 380

Gly Lys Gly Asp Phe Asn Pro Asp Lys Glu Leu Thr Met Thr Phe Thr
385                 390                 395                 400

Arg Thr Arg Ile Gln Asn Asp Ser Glu Ile Val Gln Ser Leu Val Gln
            405                 410                 415

Gly Val Thr Gly Gly Ile Met Ser Lys Glu Thr Ala Val Ala Arg Asn
            420                 425                 430

Pro Phe Val Gln Asp Pro Glu Glu Glu Leu Ala Arg Ile Glu Glu Glu
            435                 440                 445

Met Asn Gln Tyr Ala Glu Met Gln Gly Asn Leu Leu Asp Asp Glu Gly
            450                 455                 460

Gly Asp Asp Asp Leu Glu Glu Asp Asp Pro Asn Ala Gly Ala Ala Glu
465                 470                 475                 480

Ser Gly Gly Ala Gly Gln Val Ser Gly Gly His His His His His His
            485                 490                 495

<210> SEQ ID NO 7
<211> LENGTH: 1536
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atggctgata tctacccact agggaaaaca cacacagagg aactgaatga aatcatcgta      60
gagagcgcga aggagatcgc agaaccggac acaaccatga tccagaagct tattgacgaa     120 cataaccccgg agccgctatt gaagggcgtc cggtactaca tgtgcgagaa cgacattgag    180
aagaagcggc gcacatacta cgatgccgca ggacagcaat tagtggacga cacaaagacc    240
aataaccgta ctagccacgc atggcacaag ctgtttgtgg atcagaaaac acagtaccta    300
gtgggtgagc tgttacatt cacatcagac aataagacgt tattagagta cgtcaatgag    360
cttgcagacg acgactttga cgacattttg aacgagacag tcaagaatat gtcaaacaag    420
ggtattgaat actggcatcc gttcgttgat gaagaagggg aatttgatta tgttattttc    480
ccggctgagg aaatgattgt tgtatacaaa gacaacaccc gccgcgacat ccttttttgcc    540 ctccgctact actcatacaa gggcatcatg ggtgaagaga cacagaaagc agagctgtac    600
acagacacac acgtttacta ctacgaaaaa attgacggcg tttatcagat ggactattcg    660
```

```
tatggcgaaa ataaccccg gccgcacatg acaaagggtg gacaagccat aggatgggga      720
agagtaccga tcatcccgtt caaaaacaat gaggaaatgg tgtccgatct taaattctac     780
aaggatttaa tcgacaatta cgacagcatc acatccagca caatggactc attcagcgac    840
ttccaacaaa ttgtgtacgt gctcaaaaac tatgacgggg agaacccgaa agaattcacg    900
gcgaatttaa ggtaccacag tgtaattaag gtatcgggcg atggtggtgt tgacacttta   960
cgggctgaaa tacctgtgga tagtgccgca aaagagcttg aaagaataca agatgagctg   1020
tataaatccg ctcaggctgt ggataattca ccagaaacaa tcggaggagg ggctacaggc   1080
ccagcactgg aaaacctttta tgcgctactc gacttgaaag cgaacatggc tgaacggaaa  1140
atacgggctg gattgcgctt gttcttttgg ttcttcgctg aatacctacg caacacaggg   1200
aagggcgatt ttaacccgga taagagcttt acaatgacgt tcacacgcac taggattcag   1260
aatgacagcg agattgttca gagtcttgta caaggcgtta caggtggcat catgagtaaa   1320
gagacggccg tcgcacgcaa tccatttgtc caagacccag aggaagaatt ggcccgcata  1380
ggagggggaa tgaaccaata cgctgaaatg cagggcaacc tactcgacga tgagggcggg  1440
gatgatgatt tagaggagga tgatccaaat gccggagccg cagaatcagg aggagctgga  1500
caagtatctg gtggccacca tcaccatcac cattag                              1536
```

<210> SEQ ID NO 8
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Asp Ile Tyr Pro Leu Gly Lys Thr His Thr Glu Glu Leu Asn
1               5                   10                  15

Glu Ile Ile Val Glu Ser Ala Lys Glu Ile Ala Glu Pro Asp Thr Thr
            20                  25                  30

Met Ile Gln Lys Leu Ile Asp Glu His Asn Pro Glu Pro Leu Leu Lys
        35                  40                  45

Gly Val Arg Tyr Tyr Met Cys Glu Asn Asp Ile Glu Lys Lys Arg Arg
    50                  55                  60

Thr Tyr Tyr Asp Ala Ala Gly Gln Gln Leu Val Asp Asp Thr Lys Thr
65                  70                  75                  80

Asn Asn Arg Thr Ser His Ala Trp His Lys Leu Phe Val Asp Gln Lys
                85                  90                  95

Thr Gln Tyr Leu Val Gly Glu Pro Val Thr Phe Thr Ser Asp Asn Lys
            100                 105                 110

Thr Leu Leu Glu Tyr Val Asn Glu Leu Ala Asp Asp Phe Asp Asp
        115                 120                 125

Ile Leu Asn Glu Thr Val Lys Asn Met Ser Asn Lys Gly Ile Glu Tyr
    130                 135                 140

Trp His Pro Phe Val Asp Glu Glu Gly Glu Phe Asp Tyr Val Ile Phe
145                 150                 155                 160

Pro Ala Glu Glu Met Ile Val Val Tyr Lys Asp Asn Thr Arg Arg Asp
                165                 170                 175

Ile Leu Phe Ala Leu Arg Tyr Tyr Ser Tyr Lys Gly Ile Met Gly Glu
            180                 185                 190

Glu Thr Gln Lys Ala Glu Leu Tyr Thr Asp Thr His Val Tyr Tyr Tyr
        195                 200                 205

-continued

Glu Lys Ile Asp Gly Val Tyr Gln Met Asp Tyr Ser Tyr Gly Glu Asn
    210                 215                 220

Asn Pro Arg Pro His Met Thr Lys Gly Gly Gln Ala Ile Gly Trp Gly
225                 230                 235                 240

Arg Val Pro Ile Ile Pro Phe Lys Asn Asn Glu Glu Met Val Ser Asp
                245                 250                 255

Leu Lys Phe Tyr Lys Asp Leu Ile Asp Asn Tyr Asp Ser Ile Thr Ser
            260                 265                 270

Ser Thr Met Asp Ser Phe Ser Asp Phe Gln Gln Ile Val Tyr Val Leu
        275                 280                 285

Lys Asn Tyr Asp Gly Glu Asn Pro Lys Glu Phe Thr Ala Asn Leu Arg
    290                 295                 300

Tyr His Ser Val Ile Lys Val Ser Gly Asp Gly Val Asp Thr Leu
305                 310                 315                 320

Arg Ala Glu Ile Pro Val Asp Ser Ala Ala Lys Glu Leu Glu Arg Ile
                325                 330                 335

Gln Asp Glu Leu Tyr Lys Ser Ala Gln Ala Val Asp Asn Ser Pro Glu
            340                 345                 350

Thr Ile Gly Gly Ala Thr Gly Pro Ala Leu Glu Asn Leu Tyr Ala
        355                 360                 365

Leu Leu Asp Leu Lys Ala Asn Met Ala Glu Arg Lys Ile Arg Ala Gly
    370                 375                 380

Leu Arg Leu Phe Phe Trp Phe Phe Ala Glu Tyr Leu Arg Asn Thr Gly
385                 390                 395                 400

Lys Gly Asp Phe Asn Pro Asp Lys Glu Leu Thr Met Thr Phe Thr Arg
                405                 410                 415

Thr Arg Ile Gln Asn Asp Ser Glu Ile Val Gln Ser Leu Val Gln Gly
            420                 425                 430

Val Thr Gly Gly Ile Met Ser Lys Glu Thr Ala Val Ala Arg Asn Pro
        435                 440                 445

Phe Val Gln Asp Pro Glu Glu Glu Leu Ala Arg Ile Gly Gly Gly Met
    450                 455                 460

Asn Gln Tyr Ala Glu Met Gln Gly Asn Leu Leu Asp Asp Glu Gly Gly
465                 470                 475                 480

Asp Asp Asp Leu Glu Glu Asp Pro Asn Ala Gly Ala Ala Glu Ser
                485                 490                 495

Gly Gly Ala Gly Gln Val Ser Gly Gly His His His His His His
            500                 505                 510

<210> SEQ ID NO 9
<211> LENGTH: 1536
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 9
atggctgata tctacccact agggaaaaca cacacagagg aactgaatga aatcatcgta      60
gagagcgcga aggagatcgc agaaccggac acaaccatga tccagaagct tattgacgaa    120
cataacccgg agccgctatt gaagggcgtc cggtactaca tgtgcgagaa cgacattgag    180
aagaagcggc gcacatacta cgatgccgca ggacagcaat tagtggacga cacaaagacc    240

```
aataaccgta ctagccacgc atggcacaag ctgtttgtgg atcagaaaac acagtaccta    300
gtgggtgagc ctgttacatt cacatcagac aataagacgt tattagagta cgtcaatgag    360
cttgcagacg acgactttga cgacattttg aacgagacag tcaagaatat gtcaaacaag    420
ggtattgaat actggcatcc gttcgttgat gaagaagggg aatttgatta tgttattttc    480
ccggctgagg aaatgattgt tgtatacaaa gacaacaccc gccgcgacat cctttttgcc    540
ctccgctact actcatacaa gggcatcatg ggtgaagaga cacagaaagc agagctgtac    600
acagacacac acgtttacta ctacgaaaaa attgacggcg tttatcagat ggactattcg    660
tatggcgaaa ataccccccg gccgcacatg acaaagggtg acaagccat aggatgggga    720 agagtaccga tcatcccgtt caaaaacaat gaggaaatgg tgtccgatct aaattctac    780 aaggatttaa tcgacaatta cgacagcatc acatccagca caatggactc attcagcgac    840
ttccaacaaa ttgtgtacgt gctcaaaaac tatgacgggg agaacccgaa agaattcacg    900
gcgaatttaa ggtaccacag tgtaattaag gtatcgggca atggtggtgt taacacttta    960
cgggctgaaa tacctgtgga tagtgccgca aaagagcttg aaagaataca agatgagctg    1020
tataaatccg ctcaggctgt ggataattca ccagaaacaa tcggaggagg ggctacaggc    1080
ccagcactgg aaaaccttta tgcgctactc gacttgaaag cgaacatggc tgaacggaaa    1140
atacgggctg gattgcgctt gttcttttgg ttcttcgctg aatacctacg caacacaggg    1200
aagggcgatt ttaacccgga taaagagctt acaatgacgt tcacacgcac taggattcag    1260
aatgacagcg agattgttca gagtcttgta caaggcgtta caggtggcat catgagtaaa    1320
gagacggccg tcgcacgcaa tccatttgtc caagacccag aggaagaatt ggcccgcata    1380
gaagaggaaa tgaaccaata cgctgaaatg cagggcaacc tactcgacga tgagggcggg    1440
gatgatgatt tagaggagga tgatccaaat gccggagccg cagaatcagg aggagctgga    1500
caagtatctg gtggccacca tcaccatcac cattag    1536
```

<210> SEQ ID NO 10
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Ala Asp Ile Tyr Pro Leu Gly Lys Thr His Thr Glu Glu Leu Asn
1               5                   10                  15

Glu Ile Ile Val Glu Ser Ala Lys Glu Ile Ala Glu Pro Asp Thr Thr
            20                  25                  30

Met Ile Gln Lys Leu Ile Asp Glu His Asn Pro Glu Pro Leu Leu Lys
        35                  40                  45

Gly Val Arg Tyr Tyr Met Cys Glu Asn Asp Ile Glu Lys Lys Arg Arg
    50                  55                  60

Thr Tyr Tyr Asp Ala Ala Gly Gln Gln Leu Val Asp Asp Thr Lys Thr
65                  70                  75                  80

Asn Asn Arg Thr Ser His Ala Trp His Lys Leu Phe Val Asp Gln Lys
                85                  90                  95

Thr Gln Tyr Leu Val Gly Glu Pro Val Thr Phe Thr Ser Asp Asn Lys
            100                 105                 110

Thr Leu Leu Glu Tyr Val Asn Glu Leu Ala Asp Asp Phe Asp Asp
        115                 120                 125
```

Ile Leu Asn Glu Thr Val Lys Asn Met Ser Asn Lys Gly Ile Glu Tyr
130                 135                 140

Trp His Pro Phe Val Asp Glu Glu Gly Glu Phe Asp Tyr Val Ile Phe
145                 150                 155                 160

Pro Ala Glu Glu Met Ile Val Val Tyr Lys Asp Asn Thr Arg Arg Asp
                165                 170                 175

Ile Leu Phe Ala Leu Arg Tyr Tyr Ser Tyr Lys Gly Ile Met Gly Glu
                180                 185                 190

Glu Thr Gln Lys Ala Glu Leu Tyr Thr Asp Thr His Val Tyr Tyr Tyr
        195                 200                 205

Glu Lys Ile Asp Gly Val Tyr Gln Met Asp Tyr Ser Tyr Gly Glu Asn
210                 215                 220

Asn Pro Arg Pro His Met Thr Lys Gly Gly Gln Ala Ile Gly Trp Gly
225                 230                 235                 240

Arg Val Pro Ile Ile Pro Phe Lys Asn Asn Glu Glu Met Val Ser Asp
                245                 250                 255

Leu Lys Phe Tyr Lys Asp Leu Ile Asp Asn Tyr Asp Ser Ile Thr Ser
                260                 265                 270

Ser Thr Met Asp Ser Phe Ser Asp Phe Gln Gln Ile Val Tyr Val Leu
        275                 280                 285

Lys Asn Tyr Asp Gly Glu Asn Pro Lys Glu Phe Thr Ala Asn Leu Arg
290                 295                 300

Tyr His Ser Val Ile Lys Val Ser Gly Asn Gly Val Asn Thr Leu
305                 310                 315                 320

Arg Ala Glu Ile Pro Val Asp Ser Ala Ala Lys Glu Leu Glu Arg Ile
                325                 330                 335

Gln Asp Glu Leu Tyr Lys Ser Ala Gln Ala Val Asp Asn Ser Pro Glu
                340                 345                 350

Thr Ile Gly Gly Gly Ala Thr Gly Pro Ala Leu Glu Asn Leu Tyr Ala
        355                 360                 365

Leu Leu Asp Leu Lys Ala Asn Met Ala Glu Arg Lys Ile Arg Ala Gly
370                 375                 380

Leu Arg Leu Phe Phe Trp Phe Phe Ala Glu Tyr Leu Arg Asn Thr Gly
385                 390                 395                 400

Lys Gly Asp Phe Asn Pro Asp Lys Glu Leu Thr Met Thr Phe Thr Arg
                405                 410                 415

Thr Arg Ile Gln Asn Asp Ser Glu Ile Val Gln Ser Leu Val Gln Gly
                420                 425                 430

Val Thr Gly Gly Ile Met Ser Lys Glu Thr Ala Val Ala Arg Asn Pro
        435                 440                 445

Phe Val Gln Asp Pro Glu Glu Glu Leu Ala Arg Ile Glu Glu Glu Met
450                 455                 460

Asn Gln Tyr Ala Glu Met Gln Gly Asn Leu Leu Asp Asp Gly Gly
465                 470                 475                 480

Asp Asp Asp Leu Glu Glu Asp Asp Pro Asn Ala Gly Ala Ala Glu Ser
                485                 490                 495

Gly Gly Ala Gly Gln Val Ser Gly Gly His His His His His
        500                 505                 510

<210> SEQ ID NO 11
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6xHis tag

<400> SEQUENCE: 11

His His His His His His
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      tag

<400> SEQUENCE: 12

Gly Gly Gly Gly Gly Gly
1               5

<210> SEQ ID NO 13
<211> LENGTH: 12
<212> TYPE: PRT
<213> ORGANISM: Human immunodeficiency virus

<400> SEQUENCE: 13

Cys Tyr Gly Arg Lys Lys Arg Arg Gln Arg Arg Arg
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      tag

<400> SEQUENCE: 14

Gly Gly His His His His His His
1               5
```